(12) United States Patent
Feng et al.

(10) Patent No.: US 10,426,799 B2
(45) Date of Patent: Oct. 1, 2019

(54) METHODS FOR PRODUCTION OF PLATELETS FROM PLURIPOTENT STEM CELLS AND COMPOSITIONS THEREOF

(71) Applicant: Ocata Therapeutics, Inc., Marlborough, MA (US)

(72) Inventors: Qiang Feng, Natick, MA (US); Shi-Jiang Lu, Shrewsbury, MA (US); Robert P. Lanza, Clinton, MA (US)

(73) Assignee: Astellas Institute for Regenerative Medicine, Marlborough, MA (US)

( * ) Notice: Subject to any disclaimer, the term of this patent is extended or adjusted under 35 U.S.C. 154(b) by 1 day.

(21) Appl. No.: 14/653,969

(22) PCT Filed: Dec. 21, 2013

(86) PCT No.: PCT/US2013/077334
§ 371 (c)(1),
(2) Date: Jun. 19, 2015

(87) PCT Pub. No.: WO2014/100779
PCT Pub. Date: Jun. 26, 2014

(65) Prior Publication Data
US 2015/0313944 A1    Nov. 5, 2015

Related U.S. Application Data

(60) Provisional application No. 61/740,699, filed on Dec. 21, 2012, provisional application No. 61/787,476, filed on Mar. 15, 2013.

(51) Int. Cl.
*A61K 35/19* (2015.01)
*C12N 5/078* (2010.01)

(52) U.S. Cl.
CPC ............ *A61K 35/19* (2013.01); *C12N 5/0644* (2013.01); *C12N 2501/04* (2013.01); *C12N 2501/20* (2013.01); *C12N 2501/2306* (2013.01); *C12N 2501/2309* (2013.01); *C12N 2501/2311* (2013.01); *C12N 2501/30* (2013.01); *C12N 2501/40* (2013.01); *C12N 2501/727* (2013.01); *C12N 2501/734* (2013.01); *C12N 2501/91* (2013.01); *C12N 2506/11* (2013.01); *Y02A 50/411* (2018.01)

(58) Field of Classification Search
CPC ..................................................... A61K 35/19
See application file for complete search history.

(56) References Cited

U.S. PATENT DOCUMENTS

| | | | |
|---|---|---|---|
| 5,649,903 A | 7/1997 | Deniega | |
| 7,282,201 B2 | 10/2007 | Miura et al. | |
| 7,476,326 B2 | 1/2009 | Ahn et al. | |
| 7,718,420 B2 | 5/2010 | Kim et al. | |
| 7,790,458 B2 | 9/2010 | Xu et al. | |
| 8,017,393 B2 | 9/2011 | Lanza et al. | |
| 8,252,587 B2 | 8/2012 | Fong et al. | |
| 8,263,403 B2 | 9/2012 | Perry et al. | |
| 8,372,642 B2 | 2/2013 | Rajesh et al. | |
| 8,535,943 B2 | 9/2013 | Nakano et al. | |
| 8,546,141 B2 | 10/2013 | Nakauchi et al. | |
| 8,933,071 B2 | 1/2015 | Crispino et al. | |
| 9,012,221 B2 | 4/2015 | Baruch et al. | |
| 9,074,186 B2 | 7/2015 | Murphy et al. | |
| 9,200,254 B2 | 12/2015 | Eto et al. | |
| 9,763,984 B2 | 9/2017 | Feng et al. | |
| 9,993,503 B2 | 6/2018 | Feng et al. | |
| 2003/0153082 A1 | 8/2003 | Bhatia | |
| 2004/0136973 A1 | 7/2004 | Huberman et al. | |
| 2005/0176142 A1 | 8/2005 | Nakorn et al. | |
| 2007/0077654 A1 | 4/2007 | Thomson | |
| 2007/0243608 A1 | 10/2007 | Kyba et al. | |
| 2010/0248361 A1 | 9/2010 | Lasky et al. | |
| 2010/0316613 A1 | 12/2010 | Upton et al. | |
| 2011/0053267 A1 | 3/2011 | Nakauchi et al. | |
| 2011/0086424 A1 | 4/2011 | Lanza et al. | |
| 2011/0280861 A1 | 11/2011 | Scadden et al. | |
| 2012/0238020 A1* | 9/2012 | Mitchell | C12M 23/58 435/377 |
| 2012/0276063 A1 | 11/2012 | Meyer et al. | |
| 2012/0282228 A1 | 11/2012 | Bhasin | |
| 2012/0315338 A1 | 12/2012 | Li et al. | |
| 2013/0210141 A1 | 8/2013 | Rajesh et al. | |
| 2014/0037600 A1 | 2/2014 | Yu et al. | |
| 2014/0086883 A1 | 3/2014 | Poncz et al. | |
| 2014/0127815 A1 | 5/2014 | Eto et al. | |
| 2014/0205582 A1 | 7/2014 | Karsunky et al. | |
| 2014/0227780 A1 | 8/2014 | Nishino et al. | |
| 2014/0271590 A1 | 9/2014 | Feng et al. | |
| 2014/0315760 A1 | 10/2014 | Ratner et al. | |
| 2015/0004694 A1 | 1/2015 | Mayaudon et al. | |

(Continued)

FOREIGN PATENT DOCUMENTS

CN    101052710 A    10/2007
CN    101981181 A    2/2011

(Continued)

OTHER PUBLICATIONS

Brevini et al., 2010, Theriogenology, vol. 74, pp. 544-550.*

(Continued)

*Primary Examiner* — Thaian N Ton
*Assistant Examiner* — David A. Montanari
(74) *Attorney, Agent, or Firm* — Wolf, Greenfield & Sacks, P.C.

(57) ABSTRACT

Methods for production of platelets from pluripotent stem cells, such as human embryonic stem cells (hESCs) and induced pluripotent stem cells (iPSCs) are provided. These methods may be performed without forming embryoid bodies or clusters of pluripotent stem cells, and may be performed without the use of stromal inducer cells. Additionally, the yield and/or purity can be greater than has been reported for prior methods of producing platelets from pluripotent stem cells. Also provided are compositions and pharmaceutical preparations comprising platelets, preferably produced from pluripotent stem cells.

32 Claims, 27 Drawing Sheets

Specification includes a Sequence Listing.

(56) References Cited

U.S. PATENT DOCUMENTS

| | | |
|---|---|---|
| 2015/0079030 A1 | 3/2015 | Moore |
| 2015/0087065 A1 | 3/2015 | Haecker |
| 2015/0111296 A1 | 4/2015 | Pedersen et al. |
| 2015/0203819 A1 | 7/2015 | Murphy et al. |
| 2015/0275176 A1 | 10/2015 | Kobayashi et al. |
| 2015/0335682 A1 | 11/2015 | Murphy et al. |
| 2015/0361398 A1 | 12/2015 | Sandler et al. |
| 2016/0002586 A1 | 1/2016 | Mitchell |
| 2016/0002599 A1 | 1/2016 | Eto |
| 2016/0022736 A1 | 1/2016 | Feng et al. |
| 2016/0139124 A1 | 5/2016 | Newman et al. |
| 2016/0145573 A1 | 5/2016 | Liu |
| 2016/0168540 A1 | 6/2016 | Hirata et al. |
| 2016/0177265 A1 | 6/2016 | Matsubara et al. |
| 2016/0206783 A1 | 7/2016 | Dietz et al. |
| 2016/0235889 A1 | 8/2016 | Pallotta et al. |
| 2016/0272941 A1 | 9/2016 | Baruch et al. |
| 2018/0008640 A1 | 1/2018 | Feng et al. |
| 2018/0318353 A1 | 11/2018 | Feng et al. |

FOREIGN PATENT DOCUMENTS

| | | |
|---|---|---|
| JP | 2004-535389 A | 11/2004 |
| WO | WO 02/089730 A2 | 11/2002 |
| WO | WO 2006/001954 A2 | 1/2006 |
| WO | WO 2006/050330 A2 | 5/2006 |
| WO | WO 2008/151386 A1 | 12/2008 |
| WO | WO 2008/151390 A1 | 12/2008 |
| WO | WO 2009/122747 A1 | 8/2009 |
| WO | WO 2009/119105 A1 | 10/2009 |
| WO | WO 2011/069127 A1 | 6/2011 |
| WO | WO 2014/138485 A1 | 9/2014 |
| WO | WO 2015/179301 A1 | 11/2015 |
| WO | WO 2015/191632 A1 | 12/2015 |
| WO | WO 2016/160860 A1 | 10/2016 |

OTHER PUBLICATIONS

Paris et al. (2010, Theriogenology, vol. 74, pp. 516-524).*
Munoz et al. (2008, Theriogenology, vol. 69, pp. 1159-1164).*
Gomez et al. (2010, Theriogenology, vol. 74, pp. 498-515).*
Jean et al. (2013, Develop. Growth Differ., vol. 55, pp. 41-51).*
Buta et al. (2013, Stem Cell Res., vol. 11, pp. 552-562).*
Seiler et al. (2011, J. Biomedicine and Biotechnology, pp. 1-7).*
Vo et al. (2015, Blood, vol. 125(17), pp. 2641-2648).*
2004, Qi et al., PNAS, vol. 101(16), pp. 6027-6032.*
2016, Morikawa et al. (Stem Cell Reports, vol. 6, pp. 64-73).*
Tanaka et al. (1994, Blood, vol. 80(7), pp. 1743-1749) (Year: 1994).*
Karsunky et al. (2003, J. Exp. Med., vol. 198(2), pp. 305-313) (Year: 2003).*
Kimura et al., 1990, Eur. J. Immunol., vol. 20, pp. 1927-1931 (Year: 1990).*
Xie et al., 2003, Blood, vol. 101, pp. 1329-1335 (Year: 2003).*
Encabo et al., 2003, J. Hematology, vol. 88(4), pp. 388-395 (Year: 2003).*
Chadwick et al., Cytokines and BMP-4 promote hematopoietic differentiation of human embryonic stem cells. Blood. Aug. 1, 2003;102(3):906-15. Epub Apr. 17, 2003.
Chang et al., Proplatelet formation is regulated by the Rho/ROCK pathway. Blood. May 15, 2007;109(10):4229-36. Epub Jan. 23, 2007.
Chang et al., Definitive-like erythroid cells derived from human embryonic stem cells coexpress high levels of embryonic and fetal globins with little or no. adult globin. Blood. Sep. 1, 2006;108(5):1515-23. Epub Apr. 27, 2006.
Chen et al., A point mutation in the integrin beta 3 cytoplasmic domain (5752-->P) impairs bidirectional signaling through alpha IIb beta 3 (platelet glycoprotein IIb-IIIa). Blood. Sep. 15, 1994;84(6):1857-65.
Cho et al., A critical role for extracellular protein disulfide isomerase during thrombus formation in mice. J Clin Invest. Mar. 2008;118(3):1123-31. doi: 10.1172/JCI34134.
Cho et al., Enhancement of thrombogenesis by plasma fibronectin cross-linked to fibrin and assembled in platelet thrombi. Blood. May 1, 2006;107(9):3555-63. Epub Jan. 3, 2006.
Chockalingam et al., Management of patients refractory to platelet transfusion. J Infus Nurs. Jul.-Aug. 2007;30(4):220-5. Review. Abstract Only.
Coller, Anti-GPIIb/IIIa drugs: current strategies and future directions. Thromb Haemost. Jul. 2001;86(1):427-43. Review. Abstract Only.
Day et al., Murine thrombosis models. Thromb Haemost. Sep. 2004;92(3):486-94.
Doe et al., Novel Rho kinase inhibitors with anti-inflammatory and vasodilatory activities. J Pharmacol Exp Ther. Jan. 2007;320(1):89-98. Epub Oct. 3, 2006.
Falati et al., Real-time in vivo imaging of platelets, tissue factor and fibrin during arterial thrombus formation in the mouse. Nat Med. Oct. 2002;8(10):1175-81. Epub Sep. 16, 2002. Abstract only.
Feng et al., Scalable generation of universal platelets from human induced pluripotent stem cells. Stem Cell Reports. Nov. 11, 20014;3(5):817-31. doi: 10.1016/j.stemcr.2014.09.010. Epub Oct. 16, 2014.
Fujiki et al., Role of human interleukin-9 as a megakaryocyte potentiator in culture. Exp Hematol. Dec. 2002;30(12):1373-80. Abstract only.
Fujimoto et al., Production of functional platelets by differentiated embryonic stem (ES) cells in vitro. Blood. Dec. 1, 2003;102(12):4044-51. Epub Aug. 14, 2003.
Furie et al., In vivo thrombus formation. J Thromb Haemost. Jul. 2007;5Suppl 1:12-7. Review.
Furie et al., Mechanisms of thrombus formation. N Engl J Med. Aug. 28, 2008;359(9):938-49. doi: 10.1056/NEJMra0801082. Review. First 100 words only.
Gaur et al., Megakaryocytes derived from human embryonic stem cells: a genetically tractable system to study megakaryocytopoiesis and integrin function. J Thromb Haemost. Feb. 2006;4(2):436-42.
Giammona et al., Nicotinamide (vitamin B3) increases the polyploidisation and proplatelet formation of cultured primary human megakaryocytes. Br J Haematol. Nov. 2006;135(4):554-66.
Ginsberg et al., Inside-out integrin signalling. Curr Opin Cell Biol. Oct. 1992;4(5):766-71. Review. Abstract only.
Guerriero et al., Stromal cell-derived factor 1alpha increases polyploidization of megakaryocytes generated by human hematopoietic progenitor cells. Blood. May 1, 2001;97(9):2587-95.
Hod et al., Platelet transfusion refractoriness. Br J Haematol. Jul. 2008;142(3):348-60. doi: 10.1111/j.1365-2141.2008.07189.x. Epub May 28, 2008. Review.
Hu et al., Full reconstitution of human platelets in humanized mice after macrophage depletion. Blood. Aug. 23, 2012;120(8):1713-6. doi: 10.1182/blood-2012-01-407890. Epub Jul. 6, 2012.
Iacopetti et al., Application of Platelet-Rich Gel to Enhance Wound Healing in the Horse: A Case Report. J Equine Veterinary Sci. Aug. 2011; 1-6.
Ishizaki et al., Pharmacological properties of Y-27632, a specific inhibitor of rho-associated kinases. Mol Pharmacol. May 2000;57(5):976-83.
Jeanpierre et al., BMP4 regulation of human megakaryocytic differentiation is involved in thrombopoietin signaling. Blood. Oct. 15, 2008;112(8):3154-63. doi: 10.1182/blood-2008-03-145326. Epub Jul. 29, 2008.
Junt et al., Dynamic visualization of thrombopoiesis within bone marrow. Science. Sep. 21, 2007;317(5845):1767-70.
Kanaji et al., Megakaryocyte proliferation and ploidy regulated by the cytoplasmic tail of glycoprotein Ibalpha. Blood. Nov. 5, 2004;104(10):3161-8.
Kaufman et al., Hematopoietic colony-forming cells derived from human embryonic stem cells. Proc Natl Acad Sci U S A. Sep. 11, 2001;98(19):10716-21. Epub Sep. 4, 2001.

(56) References Cited

OTHER PUBLICATIONS

Khan et al., New strategies in acute myeloid leukemia: redefining prognostic markers to guide therapy. Clin Cancer Res. Oct. 1, 2012;18(19):5163-71. doi: 10.1158/1078-0432.CCR-12-0313. Epub Aug. 14, 2012.
Klimanskaya et al., Approaches of derivation and maintenance of human ES cells: Detailed procedures and alernatives. vol. 1: *Embryonic Stem Cells*. New York: Elsevier/Academic Press; 2004:437-49.
Klimchenko et al., A common bipotent progenitor generates the erythroid and megakaryocyte lineages in embryonic stem cell-derived primitive hematopoiesis. Blood. Aug. 0, 2009;114(8):1506-17. doi:10.1182/blood-2008-09-178863. Epub May 28, 2009.
Lalezari et al., Ability of thrombocytes to acquire HLA specificity from plasma. Blood. Jan. 1982;59(1):167-70.
Lane et al., Stromal-derived factor 1-induced megakaryocyte migration and platelet production is dependent on matrix metalloproteinases. Blood. Dec. 15, 2000;96(13):4152-9.
Larson et al., Regulation of proplatelet formation and platelet release by integrin alpha IIb beta3. Blood. Sep. 1, 2006;108(5):1509-14. Epub May 2, 2006.
Law et al., Analysis of human megakaryocytic cells using dual-color immunofluorescence labeling. Cytometry. Dec. 1, 2000;41(4):308-15.
Ledran et al., Efficient hematopoietic differentiation of human embryonic stem cells on stromal cells derived from hematopoietic niches. Cell Stem Cell. Jul. 3, 2008;3(1):85-98. doi: 10.1016/j.stem.2008.06.001.
Lordier et al., Megakaryocyte endomitosis is a failure of late cytokinesis related to defects in the contractile ring and Rho/Rock signaling. Blood. Oct. 15, 2008;112(8):3164-74. doi: 10.1182/blood-2008-03-144956. Epub Aug. 6, 2008.
Lu et al., Biologic properties and enucleation of red blood cells from human embryonic stem cells. Blood. Dec. 1, 2008;112(12):4475-84. doi: 10.1182/blood-2008-05-157198. Epub Aug. 19, 2008.
Lu et al., CD34+CD38− hematopoietic precursors derived from human embryonic stem cells exhibit an embryonic gene expression pattern. Blood. Jun. 1, 2004;103(11):4134-41. Epub Feb. 12, 2004.
Lu et al., Generation of functional hemangioblasts from human embryonic stem cells. Nat Methods. Jun. 2007;4(6):501-9. Epub May 7, 2007.
Lu et al., Platelets generated from human embryonic stem cells are functional in vitro and in the microcirculation of living mice. Cell Res. Mar. 2011;21(3):530-45. doi: 10.1038/cr.2011.8. Epub Jan. 11, 2011.
Lu et al., Robust generation of hemangioblastic progenitors from human embryonic stem cells. Regen Med. Sep. 2008;3(5):693-704. doi: 10.2217/17460751.3.5.693.
Matsunaga et al., Ex vivo large-scale generation of human platelets from cord blood CD34+ cells. Stem Cells. Dec. 2006;24(12):2877-87. Epub Sep. 7, 2006.
Nagata et al., Proplatelet formation of megakaryocytes is triggered by autocrine-synthesized estradiol. Genes Dev. Dec. 1, 2003;17(23):2864-9.
Nakajima et al., Effect of Wf-536, a novel ROCK inhibitor, against metastasis of B16 melanoma. Cancer Chemother Pharmacol. Oct. 2003;52(4):319-24. Epub May 29, 2003. Abstract Only.
Nishikii et al., Metalloproteinase regulation improves in vitro generation of efficacious platelets from mouse embryonic stem cells. J Exp Med. Aug. 4, 2008;205(8):1917-27. doi: 10.1084/jem.20071482. Epub Jul. 28, 2008.
Ott et al., BET bromodomain inhibition targets both c-Myc and IL7R in high-risk acute lymphoblastic leukemia. Blood. Oct. 4, 2012;120(14):2843-52. doi: 10.1182/blood-2012-02-413021. Epub Aug. 17, 2012.
Philipp et al., The effects of Mpl-ligand, interleukin-6 and interleukin-11 on megakaryocyte and platelet alpha-granule proteins. Thromb Haemost. Dec. 1998;80(6):968-75. Abstract Only.
Piper et al., In vivo recovery of human platelets in severe combined immunodeficient mice as a measure of platelet damage.Transfusion. Aug. 2007;47(8):1540-9. Abstract Only.
Qiu et al., Differentiation of human embryonic stem cells into hematopoietic cells by coculture with human fetal liver cells recapitulates the globin switch that occurs early in development. Exp Hematol. Dec. 2005;33(12):1450-8. Abstract Only.
Rafii et al., Human ESC-derived hemogenic endothelial cells undergo distinct waves of endothelial to hematopoietic transition. Blood. Jan. 31, 2013;121(5):770-80. doi: 10.1182/blood-2012-07-444208. Epub Nov. 20, 2012.
Reems et al., In vitro megakaryocyte production and platelet biogenesis: state of the art. Transfus Med Rev. Jan. 2010;24(1):33-43. doi: 10.1016/j.tmrv.2009.09.003. Review.
Robert et al., Glycoprotein Ibα receptor instability is associated with loss of quality in platelets produced in culture. Stem Cells Dev. Mar. 2011;20(3):379-90. doi: 10.1089/scd.2010.0041. Epub Sep. 15, 2010. Abstract only.
Robert et al., Megakaryocyte and platelet production from human cord blood stem cells. Methods Mol Biol. 2012;788:219-47. doi: 10.1007/978-1-61779-307-3_16. Abstract Only.
Sachs et al., In vivo thrombus formation in murine models. Circ Res. Apr. 13, 2007;100(7):979-91. Review.
Santoso et al., The presence of messenger RNA for HLA class I in human platelets and its capability for protein biosynthesis. Br J Haematol. Jul. 1993;84(3):451-6. Abstract Only.
Sasaki et al., The novel and specific Rho-kinase inhibitor (S)-(+)-2-methyl-1-[(4-methyl-5-isoquinoline)sulfonyl]-homopiperazine as a probing molecule for Rho-kinase-involved pathway. Pharmacol Ther. Feb.-Mar. 2002;93(2-3):225-32. Review. Abstract Only.
Stasi et al., Thrombopoietic agents. Blood Rev. Jul.-Sep. 2010;24(4-5):179-90. doi: 10.1016/j.blre.2010.04.002. Epub May 20, 2010. Review. Abstract Only.
Sullenbarger et al., Prolonged continuous in vitro human platelet production using three-dimensional scaffolds. Exp Hematol. Jan. 2009;37(1):101-10. doi: 10.1016/j.exphem.2008.09.009. Epub Nov. 13, 2008.
Taguchi et al., Disparate effects of interleukin 11 and thrombopoietin on megakaryocytopoiesis in vitro. Cytokine. Sep. 7, 2001;15(5):241-9. Abstract Only.
Takayama et al., Generation of functional platelets from human embryonic stem cells in vitro via ES-sacs, VEGF-promoted structures that concentrate hematopoietic progenitors. Blood. Jun. 1, 2008;111(11):5298-306. doi: 10.1182/blood-2007-10-117622. Epub Apr. 3, 2008.
Takayama et al., Transient activation of c-MYC expression is critical for efficient platelet generation from human induced pluripotent stem cells. J Exp Med. Dec. 20, 2010;207(13):2817-30. doi: 10.1084/jem.20100844. Epub Nov. 22, 2010.
Tian et al., Cytokine requirements differ for stroma and embryoid body-mediated hematopoiesis from human embryonic stem cells. Exp Hematol. Oct. 2004;32(10):1000-9. Abstract Only.
Tian et al., Differentiation of embryonic stem cells towards hematopoietic cells: progress and pitfalls. Curr Opin Hematol. Jul. 2008;15(4):312-8. doi: 10.1097/MOH.0b013e328302f429. Review. Abstract Only.
Vodyanik et al., Human embryonic stem cell-derived CD34+ cells: efficient production in the coculture with OP9 stromal cells and analysis of lymphohematopoietic potential. Blood. Jan. 15, 2005;105(2):617-26. Epub Sep. 16, 2004.
Wang et al., Generation of hematopoietic repopulating cells from human embryonic stem cells independent of ectopic HOXB4 expression. J Exp Med. May 16, 2005;201(10):1603-14. Epub May 9, 2005.
Watanabe et al., A ROCK inhibitor permits survival of dissociated human embryonic stem cells. Nat Biotechnol. Jun. 2007;25(6):681-6. Epub May 27, 2007.
Woll et al., Human embryonic stem cell-derived NK cells acquire functional receptors and cytolytic activity. J Immunol. Oct. 15, 2005;175(8):5095-103.
Zambidis et al., Hematopoietic differentiation of human embryonic stem cells progresses through sequential hematoendothelial, primitive, and definitive stages resembling human yolk sac development. Blood. Aug. 1, 2005;106(3):860-70. Epub Apr. 14, 2005.
Zhan et al., Functional antigen-presenting leucocytes derived from human embryonic stem cells in vitro. Lancet. Jul. 10-16, 2004;364(9429):163-71. Abstract Only.

(56) References Cited

OTHER PUBLICATIONS

Athanasiou et al., Increased expression of the ETS-related transcription factor FL1-1/ERGB correlates with and can induce the megakaryocytic phenotype. Cell Growth Differ. Nov. 1996;7(11):1525-34.

Feng et al., PU.1 and C/EBPalpha/beta convert fibroblasts into macrophage-like cells. Proc Natl Acad Sci U S A. Apr. 22, 2008;105(16):6057-62. doi: 10.1073/pnas.0711961105.

Figueiredo et al., RNA Interference as a tool to reduce the risk of rejection in cell-based therapies. Intech Open Science. Chapter 15 from *RNA* Interference. Downloaded via http://www.intechopen.com/books/rna-interference. DOI: http://dx.doi.org/10.5772/61829. 2016:311-324.

Guo et al., c-Myc-mediated control of cell fate in megakaryocyte-erythrocyte progenitors. Blood. Sep. 3, 2009;114(10):2097-106. doi:10.1182/blood-2009-01-197947.

Iwasaki et al., GATA-1 converts lymphoid and myelomonocytic progenitors into the megakaryocyte/erythrocyte lineages. Immunity. Sep. 2003;19(3):451-62.

Lagrue-Lak-Hal et al., Expression and function of the collagen receptor GPVI during megakaryocyte maturation. J Biol Chem. May 4, 2001;276(18):15316-25.

Lu et al., Platelets generated from human embryonic stem cells are functional in vitro and in the microcirculation of living mice. Cell Res. Mar. 2011;21(3):530-45. doi: 10.1038/cr.2011.8.

Moreau et al., Large-scale production of megakaryocytes from human pluripotent stem cells by chemically defined forward programming. Nat Commun. Apr. 7, 2016;7:11208. doi: 10.1038/ncomms11208.

Pang et al., Induction of human neuronal cells by defined transcription factors. Nature. May 26, 2011;476(7359):220-3. doi:10.1038/nature10202.

Szabo et al., Direct conversion of human fibroblasts to multilineage blood progenitors. Nature. Nov. 25, 2010;468(7323):521-6. doi: 10.1038/nature09591.

Takayama et al., Pluripotent stem cells reveal the developmental biology of human megakaryocytes and provide a source of platelets for clinical application. Cell Mol Life Sci. Oct. 2012;69(20):3419-28. doi: 10.1007/s00018-012-0995-4.

Takeuchi et al., Directed transdifferentiation of mouse mesoderm to heart tissue by defined factors. Nature. Jun. 4, 2009;459(7247):708-11. doi:10.1038/nature08039.

Thurlow et al., Analysis of human bone marrow with monoclonal antibodies. J Histochem Cytochem. Dec. 1985;33(12):1183-9.

Tijssen et al., Genome-wide analysis of simultaneous GATA1/2, RUNX1, FLI1, and SCL binding in megakaryocytes identifies hematopoietic regulators. Dev Cell. May 17, 2011;20(5):597-609. doi: 10.1016/j.devcel.2011.04.008.

Valtieri et al., Enforced TAL-1 expression stimulates primitive, erythroid and megakaryocytic progenitors but blocks the granulopoietic differentiation program. Cancer Res. Feb. 1, 1998;58(3):562-9.

Kuter et al., New thrombopoietic growth factors. Blood. Jun. 1, 2007;109(11):4607-16. Epub Feb. 8, 2007. Review.

Tsuji et al., Novel approach for formation of platelet-like particles from mouse embryonic stem cells without using feeder cells. Kurume Med J. 2009;56(3-4):61-9.

Cortin et al., Efficient in vitro megakaryocyte maturation using cytokine cocktails optimized by statistical experimental design. Exp Hematol. Oct. 2005;33(10):1182-91.

Li et al., Large scale generation of functional megakaryocytes from human embryonic stem cells (hESCs) under stromal-free conditions. Blood. 2009;114;2540. Abstract 2540. 4 pages.

\* cited by examiner

DIC Microscopy with β1-Tubulin Staining, Human Donor PLT (top) hESC-PLT (bottom)

SEQUENCE LISTING

<160> NUMBER OF SEQ ID NOS: 1

<210> SEQ ID NO 1
<211> LENGTH: 24
<212> TYPE: PRT
<213> ORGANISM: Homo Sapiens

<400> SEQUENCE: 1

Cys Lys Ala Val Leu Glu Glu Asp Glu Glu Val Thr Glu Glu Ala Glu
1               5                   10                  15

Met Glu Pro Glu Asp Lys Gly His
            20

METHODS FOR PRODUCTION OF PLATELETS FROM PLURIPOTENT STEM CELLS AND COMPOSITIONS THEREOF

RELATED APPLICATIONS

This application is a national stage filing under 35 U.S.C. § 371 of International Application No. PCT/US2013/077334, filed Dec. 21, 2013, which was published under PCT Article 21(2) in English, and which claims the benefit of U.S. Provisional Application Ser. No. 61/740,699, filed Dec. 21, 2012 and U.S. Provisional Application Ser. No. 61/787,476, filed Mar. 15, 2013, the contents of both each of which are incorporated by reference herein in their entirety.

BACKGROUND OF INVENTION

Platelets are tiny blood cells that perform the vital and highly specialized function of blood clotting. Almost a trillion platelets circulate in the average person's blood, and the turnover is such that the entire platelet population is replaced every 10 days. This represents a tremendous amount of ongoing platelet production. Platelets have a highly organized cytoskeleton and intracellular stores of over 300 proteins, which they secrete at sites of blood vessel injury. Platelets also play a role in inflammation, blood vessel growth, and tumor metastasis.

After vascular injury, platelets rapidly adhere to damaged blood vessels and trigger a complex cascade of events that result in thrombus formation. The demand for platelet transfusions has continued to increase during the last several decades (51). Using conventional methods, platelets can only be stored for less than a week, creating a continuous challenge for donor-dependent programs. Shortages in the supply of platelets can have potentially life-threatening consequences, especially in patients where multiple transfusions are necessary. Repeated transfusions may also lead to refractory responses that are linked to immunity mediated host reaction and may require costly patient matching (52; 53). The ability to generate platelets in vitro, particularly patient-matched platelets, would provide significant advantages in these clinical scenarios.

Limitations in the supply of platelets can have potentially life-threatening consequences for transfusion-dependent patients with unusual/rare blood types, particularly those who are alloimmunized, and patients with cancer or leukemia who, as often happens, develop platelet alloimmunity. Frequent transfusion of platelets is clinically necessary in these patients because the half-life of transfused human platelets is 4-5 days. Moreover, platelets from volunteer donor programs are at the constant risk of contaminations by various pathogens. Platelets cannot be stored frozen using conventional techniques, thus the ability to generate platelets in vitro would provide significant advances for platelet replacement therapy in clinical settings.

For more than a decade, human hematopoietic stem cells (HSC, CD34+) from bone marrow (BM), cord blood (CB) or peripheral blood (PB) have been studied for megakaryocyte (MK) and platelet generation. Using certain combinations of cytokines, growth factors and/or stromal feeder cells, functional platelets have been produced from HSCs with significant success (1; 2). However, HSCs are still collected from donors and have limited expansion capacity under current culture conditions, which interferes with large-scale production and future clinical applications.

Human embryonic stem cells (hESC) can be propagated and expanded in vitro indefinitely, providing a potentially inexhaustible and donorless source of cells for human therapy. Differentiation of hESCs into hematopoietic cells in vitro has been extensively investigated for the past decade. The directed hematopoietic differentiation of hESCs has been successfully achieved in vitro by means of two different types of culture systems. One of these employs cocultures of hESCs with stromal feeder cells, in serum-containing medium (3; 4). The second type of procedure employs suspension culture conditions in ultra-low cell binding plates, in the presence of cytokines with/without serum (5-7); its endpoint is the formation of cell aggregates or embryoid bodies ("EBs"). Hematopoietic precursors as well as mature, functional progenies representing erythroid, myeloid, macrophage, megakaryocytic and lymphoid lineages have been identified in both of the above differentiating hESC culture systems (3-6:8-14). Previous studies also generated megakaryocytes/platelets from hESCs by co-culturing with stromal cells in the presence of serum (15; 16). However, the yield of megakaryocytes/platelets in the above-described studies was low (15; 16).

SUMMARY OF INVENTION

The present disclosure provides methods for production of platelets from pluripotent stem cells, such as human embryonic stem cells (hESCs) and induced pluripotent stem cells (iPSCs or iPS cells), such as human induced pluripotent stem cells (hiPSCs or hiPS cells). These methods may be performed without forming embryoid bodies, and may be performed without the use of stromal inducer cells. Additionally, the yield and/or purity can be greater than has been reported for prior methods of producing platelets from pluripotent stem cells. Because platelets may be produced with greater efficiency and on a larger scale, the methods and compositions of the present disclosure have great potential for use in medicinal transfusion purposes. Additionally, because platelets do not have a nucleus and contain only minimal genetic material, preparations of the present disclosure may be irradiated before transfusion to effectively eliminate any contaminating nucleated cells, such as an undifferentiated hESC. Therefore, possible presence of nucleated cells should not present a safety issue.

Platelets collected from donors have very limited shelf life and are increasingly needed for prophylactic transfusions in patients. In contrast to donor dependent cord blood or bone marrow CD34+ human hematopoietic stem cells, human embryonic stem cells (hESCs) can be a promising alternative source for continuous in vitro production of platelets under controlled conditions. As further described herein, the disclosure provides systems and methods to generate megakaryocytes (MKs) from pluripotent stem cells under serum- and stromal-free conditions. In exemplary embodiments, pluripotent stem cells are directed towards megakaryocytes through differentiation of hemogenic endothelial cells (PVE-HE, which are further described below). A transient multi-potential cell population expressing CD31, CD144, and CD105 markers has been identified at the end of PVE-HE culture. In the presence of TPO, SCF and other cytokines in feeder-free and serum-free suspension culture, up to 100 fold expansion can be achieved from hESCs or hiPS cells to MKs in 18-20 days. Such methods can provide robust in vitro generation of MKs from pluripotent stem cells. When cultured under feeder-free conditions, pluripotent stem cell-derived MKs may be used to generate platelet-like particles (platelet or platelet-like particle produced from human induced pluripotent stem cells (hiPSC-PLTs) or from human embryonic stem cells (ES PLTs)). These hiPSC-PLTs and ES-PLTs are responsive to thrombin stimulation and able to participate in micro-aggregate formation.

In one aspect, the disclosure provides a pharmaceutical preparation that is suitable for use in a human patient comprising at least $10^8$ platelets.

Additionally, the disclosure provides a pharmaceutical preparation comprising platelets differentiated from human stem cells, e.g., at least $10^8$ platelets. Optionally, the preparation may be substantially free of leukocytes. Optionally, substantially all of the platelets may be functional.

The pharmaceutical preparation may comprise $10^9$-$10^{14}$ platelets, optionally $10^9$, $10^{10}$, $10^{11}$, $10^{12}$, $10^{13}$ or $10^{14}$ platelets.

The platelets may have one or more of the following attributes: a mean platelet volume range of 9.7-12.8 fL; a unimodal distribution of size in the preparation; and/or a lognormal platelet volume distribution wherein one standard deviation is less than 2 $\mu m^3$ (preferably less than 1.5 $\mu m^3$, 1 $\mu m^3$ or even 0.5 $\mu m^3$).

The platelets may be positive for at least one of the following markers: CD41a and CD42b.

The platelets may be human platelets.

At least 50%, 60%, 70%, 80% or 90% of the platelets may be functional, and optionally may be functional for at least 2, 3 or 4 days after storage at room temperature.

In another aspect, the disclosure provides a bioreactor having weakly adherent or non-adherent megakaryocytes that produce functional platelets without feeder cells.

In another aspect, the disclosure provides a composition comprising at least $10^9$ megakaryocyte lineage specific progenitors (MLPs).

In another aspect, the disclosure provides a cryopreserved composition comprising MLPs.

In another aspect, the disclosure provides a bank comprising cryopreserved MLPs.

The MLPs may be of defined HLA types.

The cryopreserved composition may be HLA matched to a patient.

In another aspect, the disclosure provides a cryopreserved composition or bank comprising $10^9$ to $10^{14}$ MLPs, optionally $10^9$, $10^{10}$, $10^{11}$, $10^{12}$, $10^{13}$ or $10^{14}$ MLPs.

In another aspect, the disclosure provides a method for producing platelets from megakaryocytes or MPLs comprising the steps of: (a) providing a non-adherent culture of megakaryocytes; (b) contacting the megakaryocytes or MPLs with TPO or a TPO agonist to cause the formation of proplatelets in culture, wherein the proplatelets release platelets; and (c) isolating the platelets.

In another aspect, the disclosure provides a method for producing platelets from megakaryocytes or MPLs comprising the steps of: (a) providing a non-adherent culture of megakaryocytes or MPLs; (b) contacting the megakaryocytes or MPLs with hematopoietic expansion medium and optionally (1) TPO or a TPO agonist, SCF, IL-6 and IL-9 or (2) TPO or a TPO agonist, SCF, and IL-11, which may cause the formation of pro-platelets in culture, wherein the pro-platelets release platelets. Said method may further comprise (c) isolating the platelets.

The TPO agonist comprises one or more of: ADP, epinephrine, thrombin, collagen, TPO-R agonists, TPO mimetics, second-generation thrombopoietic agents, romiplostim, eltrombopag (SB497115, Promacta), recombinant human thrombopoietin (TPO), pegylated recombinant human megakaryocyte growth and development factor (PEG-rHuMGDF), Fab 59, AMG 531, Peg-TPOmp, TPO nonpeptide mimetics, AKR-501, monoclonal TPO agonist antibodies, polyclonal TPO agonist antibodies, TPO minibodies, VB22B sc(Fv)2, domain subclass-converted TPO agonist antibodies, MA01G4G344, recombinant human thrombopoietins, recombinant TPO fusion proteins, or TPO non-peptide mimetics.

Optionally, substantially all the isolated platelets may be functional.

The non-adherent culture of megakaryocytes or MPLs may be a feeder-free culture.

The culture in step (b) may be in a medium comprising one or more of: Stem Cell Factor (SCF) at 0.5-100 ng/ml, Thrombopoietin (TPO) at 10-100 ng/ml, and Interleukin-11 (IL-11) at 10-100 ng/ml, at least one ROCK inhibitor, and/or Heparin at 2.5-25 Units/ml.

The culture in step (b) may be in a medium comprising one or more of: TPO at 10-100 ng/ml, SCF at 0.5-100 ng/ml, IL-6 at 5-25 ng/ml, IL-9 at 5-25 ng/ml, at least one ROCK inhibitor, and/or Heparin at 2.5-25 units/ml.

The at least one ROCK inhibitor may comprise Y27632, which Y27632 may be in a concentration of 2-20 $\mu M$, about 3-10 $\mu M$, about 4-6 $\mu M$ or about 5 $\mu M$.

The method may further comprise subjecting the megakaryocytes to a shearing force.

At least 2, 3, 4, or 5 platelets per megakaryocyte may be produced.

At least 50 platelets per megakaryocyte may be produced.

At least 100, 500, 1000, 2000, 5000, or 10000 platelets per megakaryocyte may be produced.

At least 50%, at least 60%, at least 70%, at least 80%, at least 90%, or at least 95% of said platelets may be CD41a+ and/or CD42b+, e.g., CD41a+ and CD42b+.

The platelets may be produced in the absence of feeder cells, and/or may be produced in the absence of stromal feeder cells.

The platelets may be produced in the absence of any xenogeneic cells.

The platelets may be human.

The megakaryocytes or MPLs may be cultured in the presence of an exogenously added protease inhibitor. Said megakaryocytes or MPLs may be cultured in the presence of an exogenously added MMP inhibitor. Said megakaryocytes or MPLs may be cultured in the presence of an exogenously added MMP8 inhibitor. Said megakaryocytes or MPLs may be cultured in the presence of an exogenously added MMP8 specific inhibitor and a pan MMP inhibitor.

The megakaryocytes or MPLs may be cultured at a temperature of about 39° C.

The megakaryocytes or MPLs may be generated by steps comprising: (a) culturing pluripotent stem cells to form hemogenic endothelial cells (PVE-HE); (b) culturing the hemogenic endothelial cells to form MLPs; and optionally (c) culturing the MLPs to form megakaryocytes. The pluripotent stem cells may be human.

The hemogenic endothelial cells may be cultured in step (b) in the presence of a BET inhibitor. Said BET inhibitor may be IBET151.

The hemogenic endothelial cells may be derived without embryoid body formation.

The pluripotent stem cells may be induced pluripotent stem cells (iPSC). The iPSC may be human.

The hemogenic endothelial cells may be derived without embryoid body formation.

The hemogenic endothelial cells may be differentiated from the pluripotent stem cells under low oxygen conditions comprising 1% to 10% oxygen, 2% to 8% oxygen, 3% to 7% oxygen, 4% to 6% oxygen, or about 5% oxygen.

The megakaryocytes may be differentiated from the MLPs at a temperature between 38-40 degrees C., or about 39 degrees C.

In another aspect, the disclosure provides a pharmaceutical preparation comprising platelets produced by any of the method described herein, e.g., any of the methods above.

The preparation may be suitable for use in a human patient. For example, the preparation may be suitable for use in a human patient and substantially free of leukocytes. Said preparation may comprise at least $10^8$ platelets.

In a further aspect the disclosure provides the use of a composition comprising platelets (e.g., a composition as described herein, such as in the preceding paragraphs) or a composition comprising platelets produced by a method as described herein (e.g., a method described in the preceding paragraphs) in the manufacture of a medicament for the treatment of a patient in need thereof or suffering from a disease or disorder affecting clotting or a disease or disorder treatable thereby.

The disease or disorder may comprise thrombocytopenia, trauma, a blood-borne parasite, or malaria.

In another aspect, the disclosure provides a method of treating a patient in need of platelet transfusion, comprising administering a composition comprising platelets (e.g., a composition as described herein, such as in the preceding paragraphs) or a composition comprising platelets produced by a method as described herein (e.g., a method described in the preceding paragraphs) to said patient.

The method may be effective to treat a disease or disorder comprising thrombocytopenia, trauma, a blood-borne parasite, or malaria.

In another aspect, the present disclosure provides a composition comprising an isolated PVE-HE cell, which is optionally derived from a pluripotent stem cell, and which is optionally produced according to the methods described herein.

In one aspect, the present disclosure provides a composition comprising an isolated iPS-PVE-HE cell, which is optionally produced according to the methods described herein.

In one aspect, the present disclosure provides a composition comprising an isolated hES-PVE-HE, which is optionally produced according to the methods described herein.

In one aspect, the present disclosure provides a composition comprising an isolated PVE-HE-MLP which is optionally derived from a pluripotent stem cell and which is optionally produced according to the methods described herein.

In one aspect, the present disclosure provides a composition comprising an isolated iPS-PVE-HE-MLP, which is optionally produced according to the methods described herein.

In one aspect, the present disclosure provides a composition comprising an isolated hES-PVE-HE-MLP, which is optionally produced according to the methods described herein.

In one aspect, the present disclosure provides a composition comprising an isolated PVE-HE-MLP-MK which is optionally derived from a pluripotent stem cell, and which is optionally produced according to the methods described herein.

In one aspect, the present disclosure provides a composition comprising an isolated iPS-PVE-HE-MLP-MK, which is optionally produced according to the methods described herein.

In one aspect, the present disclosure provides a composition comprising an isolated hES-PVE-HE-MLP-MK, which is optionally produced according to the methods described herein.

In another aspect, the disclosure provides a pharmaceutical preparation that is suitable for use in a human patient comprising at least $10^8$ platelets, wherein the preparation is substantially free of leukocytes and wherein substantially all of the platelets are functional.

In various embodiments, the pharmaceutical preparations are irradiated in order to remove or inactivate nucleated cells.

In another aspect, the disclosure provides a pharmaceutical preparation that is suitable for use in a human patient comprising at least $10^8$ functional platelets, wherein the mean plasma half-life of the functional platelets in the preparation is at least four days.

The pharmaceutical preparation of may comprise $10^9$-$10^{14}$ platelets, optionally $10^9$, $10^{10}$, $10^{11}$, $10^{12}$, $10^{13}$ or $10^{14}$ platelets.

The pharmaceutical preparation may comprise platelets having one or more of the following attributes: a mean platelet volume range of 9.7-12.8 fL; a unimodal distribution of size in the preparation; and/or a lognormal platelet volume distribution wherein one standard deviation is less than 2 $\mu m^3$ (preferably less than 1.5 $\mu m^3$, 1 $\mu m^3$ or even 0.5 $\mu m^3$).

The pharmaceutical preparation may comprise platelets that are positive for at least one of the following markers: CD41a and CD41b.

At least half of the platelets may be functional for at least two, three, four or five days after storage at room temperature e.g. (22-25° C.). For example, at least 60%, 70%, 80% or 90% may be functional for at least two days. The platelets may be stored at room temperature for at least five days.

In another aspect, the disclosure provides a cryopreserved bank or preparation of MLPs.

MLPs may be collected from the PVE-HE when they start to float up in suspension. Preferably the MLPs are not plated and preferably the MLPs are not allowed to adhere, thereby avoiding differentiation into other cell types and facilitating production of MKs.

The bank or preparation may comprise $10^9$ to $10^{14}$ MLPs, optionally $10^9$, $10^{10}$, $10^{11}$, $10^{12}$, $10^{13}$ or $10^{14}$ MLPs.

One MLP may yield at least 2, 3, 4, 5, or more platelets. In exemplary embodiments, a composition of $6 \times 10^{10}$ to $1.2 \times 10^{11}$ MLPs is provided sufficient to generate a therapeutic dose of 300-600$\times 10^9$ platelets at a yield of 5 platelets per MLP. In exemplary embodiments, a composition of 3-6$\times 10^9$ MLPs is provided sufficient to generate a therapeutic dose at a yield of at least 100 platelets per MLP.

In another aspect, the disclosure provides a bioreactor having weakly adherent or non-adherent megakaryocytes that produce functional platelets without feeder cells. Weakly adherent cells, including said megakaryocytes, can be mechanically separated from each other or from a surface, for example, by washing with mild force using a serological pipette. Preferably the MKs are cultured under non-adherent conditions, which is thought to promote maintenance of MK phenotypes. Shear forces may be applied to the MK culture to improve the efficiency of platelet production. For example, a microfluidic chamber or chip may be used to control shear stress, which may increase the platelet yield per MK. In one aspect, MKs can be seeded into one channel of a microfluidic chip and media can be flowed past the MKs at near physiologic rates.

In another aspect, the disclosure provides a composition comprising at least $10^9$ MLPs In another aspect, the disclosure provides a cryopreserved composition comprising MLPs.

In another aspect, the disclosure provides a method for producing platelets from megakaryocytes comprising the steps of: a) providing a non-adherent culture of megakaryocytes; b) contacting the megakaryocytes with TPO or TPO agonists to cause the formation of proplatelets in culture, wherein the proplatelets release platelets; and c) isolating the platelets.

Thrombopoietin (TPO) is thought to be a key cytokine involved in thrombopoiesis and megakaryopoiesis, and is the endogenous ligand for the thrombopoietin receptor that is expressed on the surface of platelets, megakaryocytes, and megakaryocytic precursors. TPO is a 332-amino acid (95 kDa) glycoprotein that contains 2 domains: a receptor-binding domain (residues 1-153) and a carbohydrate-rich domain (residues 154-332) that is highly glycosylated and is important for protein stability. The TPO receptor, c-Mpl (also known as CD110), is a typical hematopoietic cytokine receptor and contains 2 cytokine receptor homology modules. TPO binds only the distal cytokine receptor homology module and thereby initiates signal transduction. In the absence of the distal cytokine receptor homology module, c-Mpl becomes active, suggesting that the distal cytokine receptor homology module functions as an inhibitor of c-Mpl until it is bound by TPO. Binding by TPO activates Janus kinase 2 (Jak2) signal transducers and activators of transcription (STAT) signaling pathway to drive cell proliferation and differentiation. Megakaryocyte growth and development factor (MGDF) is another thrombopoietic growth factor. Recombinant forms of TPO and MGDF, including human and pegylated forms, may be used to induce megakaryocyte and platelet differentiation and maturation. TPO receptor-activating peptides and fusion proteins (i.e. Fab 59, romiplostim/AMG 531, or pegylated (Peg-TPOmp)) may be used in place of TPO. Nonpeptide mimetics (Eltrombopag (SB497115, Promacta), and AKR-501) bind and activate the TPO receptor by a mechanism different from TPO and may have an additive effect to TPO. TPO agonist antibodies (i.e. MA01G4G344) or minibodies (i.e. VB22B sc(Fv) 2) that activate the TPO receptor may also be used to mimic the effect of TPO. Exemplary TPO agonists are disclosed in Stasi et al., Blood Reviews 24 (2010) 179-190, and Kuter, Blood. 2007; 109:4607-4616 which is each hereby incorporated by reference in its entirety. Exemplary TPO agonists include: ADP, epinephrine, thrombin and collagen, and other compounds identified in the literature as TPO-R agonists or TPO mimetics, second-generation thrombopoietic agents, Romiplostim, Eltrombopag (SB497115, Promacta), first-generation thrombopoietic growth factors, recombinant human thrombopoietin (TPO), pegylated recombinant human megakaryocyte growth and development factor (PEG-rHuMGDF), TPO peptide mimetics, TPO receptor-activating peptides inserted into complementarity-determining regions of Fab (Fab 59), AMG 531 (a "peptibody" composed of 2 disulphide-bonded human IgG1-HC constant regions (an Fc fragment) each of which is covalently bound at residue 228 with 2 identical peptide sequences linked via polyglycine), Peg-TPOmp (a pegylated TPO peptide agonist), orally available TPO agonists, TPO nonpeptide mimetics, AKR-501, monoclonal TPO agonist antibodies, polyclonal TPO agonist antibodies, TPO minibodies such as VB22B sc(Fv)2, domain subclass-converted TPO agonist antibodies such as MA01G4G344, Recombinant human thrombopoietins, or Recombinant TPO fusion proteins, TPO nonpeptide mimetics. Wherever TPO is used as an embodiment of the invention, exemplary TPO agonists can be substituted for TPO in further embodiments of the invention.

In another aspect, the disclosure provides a method for producing platelets from megakaryocytes comprising the steps of a) providing a non-adherent culture of megakaryocytes or megakaryocyte progenitors, b) contacting the megakaryocytes or megakaryocyte progenitors with a composition comprising hematopoietic expansion media to cause the formation of proplatelets in culture, wherein the proplatelets release platelets, and c) isolating the platelets.

In exemplary embodiments, substantially all the isolated platelets are functional. In exemplary embodiments, the non-adherent culture of megakaryocytes or megakaryocyte progenitors is a feeder-free culture and/or is free of xenogeneic cells. Accordingly, the disclosure provides methods for generating platelets without feeder cells.

The culture in step (b) may be performed in a medium comprising one or more of Stem Cell Factor (SCF), Thrombopoietin (TPO), Interleukin-11 (IL-11), a ROCK Inhibitor such as Y27632 and/or Heparin. The culture in step (b) may be in a medium comprising one or more of TPO, SCF, IL-6, IL-9, a ROCK Inhibitor such as Y27632, and/or Heparin.

In one embodiment, the hematopoietic expansion medium comprises StemSpam™ ACF (ACF) (available from StemCell Technologies Inc.), and may further comprise TPO (thrombopoietin) or TPO agonist, SCF (Stem Cell Factor), IL-6 (interleukin 6) and IL-9 (interleukin 9), which may be provided as StemSpam™ CC220 cytokine cocktail (CC220) (available from StemCell Technologies Inc.). It may optionally comprise a ROCK inhibitor and/or Heparin. TPO, SCF, IL-6, IL-9, and IL-11 are known megakaryocyte development and maturation factors (Stasi et al., Blood Reviews 24 (2010) 179-190).

In one embodiment, the hematopoietic expansion medium comprises Stemline-II Hematopoietic Stem Cell Expansion Medium (Stemline-II) (available from Sigma Aldrich), and may further comprise TPO or TPO agonist, SCF, and IL-11. It may optionally comprise a ROCK inhibitor and/or Heparin. The ROCK inhibitor may be but is not limited to Y27632.

In another embodiment, the hematopoietic expansion medium comprises Iscove's Modified Dulbecco's Medium (IMDM) as a basal medium, human serum albumin (recombinant or purified), iron-saturated transferrin, insulin, b-mercaptoethanol, soluble low-density lipoprotein (LDL), and cholesterol (which may be referred to herein as a defined component medium), and may further comprise TPO or TPO agonist, SCF, and IL-11. It may optionally comprise a ROCK inhibitor and/or Heparin. The ROCK inhibitor may be but is not limited to Y27632.

In another embodiment, the hematopoietic expansion medium comprises Iscove's Modified Dulbecco's Medium (IMDM) as a basal medium, human serum albumin (recombinant or purified), iron-saturated transferrin, insulin, b-mercaptoethanol, soluble low-density lipoprotein (LDL), and cholesterol (which may be referred to herein as a defined component medium), and may further comprise TPO (thrombopoietin) or TPO agonist, SCF (Stem Cell Factor), IL-6 (interleukin 6) and IL-9 (interleukin 9). It may optionally comprise a ROCK inhibitor and/or Heparin.

The culture in step (b) may be performed in a medium comprising ACF, Stemline-II or the defined component medium of the preceding paragraph, as well as (1) one or more of SCF (e.g., at 0.5-100 ng/ml), TPO (e.g., at 10-100 ng/ml), IL-6 (e.g., at 5-25 ng/ml), IL-9 (e.g., at 5-25 ng/ml)

and Heparin (e.g., at 2.5-25 Units/ml); (2) one or more of TPO (e.g., at 10-100 ng/ml), SCF (e.g., at 0.5-100 ng/ml), IL-6 (e.g., at 5-25 ng/ml), IL-9 (e.g., at 5-25 ng/ml), Y27632 (e.g., at 5 µM, or optionally 2-20 µM, or optionally an effective concentration of another ROCK inhibitor), and Heparin (e.g., at 0.5-25 units/ml); (3) one or more of TPO (e.g., at 10-100 ng/ml), SCF (e.g., at 0.5-100 ng/ml), IL-11 (e.g., at 5-25 ng/ml), Y27632 (e.g., at 5 µM or optionally 2-20 µM, or optionally an effective concentration of another ROCK inhibitor), and Heparin (e.g., at 2.5-25 Units/ml); or (4) one or more of TPO (e.g., at 10-100 ng/ml), SCF (e.g., at 0.5-100 ng/ml), IL-6 (e.g., at 5-25 ng/ml), IL-9 (e.g., at 5-25 ng/ml), Y27632 (e.g., at 5 µM or optionally 2-20 µM, or optionally an effective concentration of another ROCK inhibitor), and Heparin (e.g., at 2.5-25 Units/ml).

The method may further comprise subjecting the megakaryocytes to a shearing force.

The method may yield at least 2, 3, 4, or 5 platelets per megakaryocyte, at least 20, 30, 40 or 50 platelets per megakaryocyte, or at least 100, 500, 1000, 2000, 5000, or 10000 platelets per megakaryocyte.

At least 50%, at least 60%, at least 70%, at least 80%, at least 90%, or at least 95% of said platelets may be CD41a+ and CD42b+.

The platelets may be produced in the absence of feeder cells or stromal feeder cells.

The platelets may be produced in the absence of any xenogeneic cells.

The platelets may be human.

The platelets may be CD41a+ and/or CD42b+.

In another aspect, the disclosure provides methods of producing megakaryocyte progenitors (also referred to herein as MLPs) (such as those utilized in a method of producing platelets or for another purpose) which may be generated by the steps of (a) culturing pluripotent stem cells to form hemogenic endothelial cells (PVE-HE); and (b) culturing the hemogenic endothelial cells to form megakaryocytes progenitors (MLPs). Step (a) may be carried out in the presence of an animal-component free medium comprised of Iscove's Modified Dulbecco's Medium (IMDM), human serum albumin, iron-saturated transferrin, insulin, b-mercaptoethanol, soluble low-density lipoprotein (LDL), cholesterol, bone morphogenetic protein 4 (BMP4) (e.g., at 50 ng/ml), basic fibroblast growth factor (bFGF) (e.g., at 50 ng/ml), and vascular endothelial growth factor (VEGF) (e.g., at 50 ng/ml). Step (b) may be carried out in Iscove's modified Dulbecco's medium (IMDM), Ham's F-12 nutrient mixture, Albucult (rh Albumin), Polyvinylalcohol (PVA), Linoleic acid, SyntheChol (synthetic cholesterol), Monothioglycerol (a-MTG), rh Insulin-transferrin-selenium-ethanolamine solution, protein-free hybridoma mixture II (PFH-MII), ascorbic acid 2 phosphate, Glutamax I (L-alanyl-L-glutamine), Penicillin/streptomycin, Stem Cell Factor (SCF) at 25 ng/ml, Thrombopoietin (TPO) (e.g., at 25 ng/ml), Fms-related tyrosine kinase 3 ligand (FL) (e.g., at 25 ng/ml), Interleukin-3 (IL-3) (e.g., at 10 ng/ml), Interleukin-6 (IL-6) (e.g., at 10 ng/ml), and Heparin (e.g., at 5 Units/ml).

In another aspect, the disclosure provides methods of producing megakaryocytes (such as those utilized in a method of producing platelets or for another purpose) which may be generated by the steps of (a) culturing pluripotent stem cells to form hemogenic endothelial cells (PVE-HE); (b) culturing the hemogenic endothelial cells to form MLPs; and (c) culturing the MLPs to form megakaryocytes as shown in Examples 1 and 2. Steps (a) and (b) may be carried out as described in the preceding paragraph. Step (c) may be carried out in Iscove's Modified Dulbecco's Medium (IMDM) as basal medium, human serum albumin, iron-saturated transferrin, insulin, b-mercaptoethanol, soluble low-density lipoprotein (LDL), cholesterol, TPO (e.g., at 30 ng/ml), SCF (e.g., at 1 ng/ml), IL-6 (e.g., at 7.5 ng/ml), IL-9 (e.g., at 13.5 ng/ml), and optionally a ROCK inhibitor such as but not limited to Y27632 (e.g., at 5 µM), and/or Heparin (e.g., at 5-25 units/ml).

In another aspect, the disclosure provides a pharmaceutical preparation comprising platelets produced by the methods above. The preparation may be suitable for use in a human patient and/or may comprise at least $10^8$ platelets, and/or may be substantially free of leukocytes.

In another aspect the disclosure provides the use of the platelets of any composition described herein or produced by any method herein described in the manufacture of a medicament for the treatment of a patient in need thereof or suffering from a disease or disorder affecting clotting.

In another aspect the disclosure provides a method of treating a patient in need of platelet transfusion, comprising administering platelets of any composition described herein or produced by any method herein described to said patient, which may be in an amount effective to treat a disease or disorder affecting clotting and/or other platelet function and/or another disorder that may be treated thereby, such as thrombocytopenia or trauma. Thrombocytopenia results from disturbances in platelet production, distribution, or destruction. It is frequently found in a variety of medical conditions, including liver cirrhosis, HIV infection, autoimmune disease, idiopathic thrombocytopenia purpura, chemotherapy-induced myelosuppression and bone marrow disorders. A low platelet count is associated with an increased risk of bleeding. An additional exemplary disease or disorder that may be treated thereby is malaria and other parasitic infections, which while not intending to be limited by theory is thought to be mediated by the ability of the human platelet factor 4 to kill malaria parasites within erythrocytes by selectively lysing the parasite's digestive vacuole (see Love et. al., Cell Host Microbe 12 (6): 815-23, which is hereby incorporated by reference in its entirety).

In another aspect the disclosure provides a method of drug delivery, comprising administering platelets of any composition described herein or produced by any method herein described to said patient, wherein said platelets deliver said drug. For example, it is thought that due to their in vivo life span, lack of engraftment post administration, and homing properties, platelets may be useful as a drug carrier. hESCs, hiPCs and MLPs may be genetically modified and used to produce platelets that express a desired drug for treatment of a disease. In one aspect, hESCs, hiPCs or MLPs could be genetically modified to express an antitumor agent. Platelets produced from such genetically modified hESCs, hiPSCs and MLPs may be used to deliver such antitumor agent to a tumor for the treatment of a neoplastic disease.

The platelets of the present invention can be engineered to include one or more therapeutic agents which are released by the platelets either in a passive manner (diffuse out of the platelet over time) or in an active manner (are released upon activation and degranulation of platelets). A wide range of drugs can be used. The engineered platelets may be prepared so that they include one or more compounds selected from the group consisting of drugs that act at synaptic and neuroeffector junctional sites; drugs that act on the central nervous system; drugs that modulate inflammatory responses; drugs that affect renal and/or cardiovascular function; drugs that affect gastrointestinal function; antibiotics; anti-cancer agents; immunomodulatory agents; drugs acting on the blood and/or the blood-forming organs; hormones; hormone antagonists; agents affecting calcification and bone turnover, vitamins, gene therapy agents; or other agents such as targeting agents, etc.

In certain embodiments, the platelets have been engineered to include one or more therapeutic agents, such as a small molecule drug, aptamer or other nucleic acid agent, or recombinant proteins, e.g., which may be stored in the platelets' granules (α-granules, for example), and preferably released upon activation of the platelets.

In certain embodiments, the platelets include one or more exogenous agents which promote or accelerate normal wound healing, reduce scarring, reduce fibrosis, or a combination thereof.

In certain embodiments, the platelets include one or more exogenous anti-fibrotic agents. Platelets engineered to deliver antithrombotic/antirestenosis agents can be used use during angioplasty and thrombolysis procedures. In certain embodiments, the engineered platelets can used to prevent or reduce the severity of atherosclerosis. In certain embodiments, the engineered platelets can used to prevent or reduce the severity of restenosis. In still other embodiments, the engineered platelets can used as part of a treatment for solid tumors. The engineered platelets may include one or more immunostimulatory agents.

A further aspect of the disclosure provides a method of producing a β2 microglobulin-deficient platelet, e.g., a reduced immunogenicity or "universal" platelet, comprising use of any method as disclosed herein to produce a platelet from a cell engineered to be deficient in β2 microglobulin expression, such as a β2 microglobulin knockout pluripotent cell. The disclosure also provides a β2 microglobulin-deficient platelet, megakaryocyte, or platelet progenitor lacking expression of β2 microglobulin. Aβ2 microglobulin-deficient platelet generally has low or preferably undetectable Class I MHC molecules present in its plasma membrane, thereby reducing immunogenicity of the platelet.

In another aspect, a method is provided for producing platelets from megakaryocytes or MLPs comprising culturing a non-adherent population of megakaryocytes of MLPs under shear force conditions in the presence of a protease inhibitor, and harvesting and optionally isolating platelets from the culture.

The protease inhibitor may be an MMP inhibitor.

The shear force conditions may be constant shear force conditions. The shear force conditions may comprise a shear force of 1-4.1 dynes/cm$^2$.

The megakaryocytes or MLPs may be cultured in a microfluidic device.

The megakaryocytes or MLPs may be derived from iPS cells, ES cells, or naturally occurring CD34$^+$ cells, optionally bone marrow or umbilical cord blood CD34$^+$ cells.

The protease inhibitor may be an MMP inhibitor such as GM6001.

The protease inhibitor may be an MMP8 specific inhibitor such as MMP8-I ((3R)-(+)-[2-(4-Methoxybenzenesulfonyl)-1,2,3,4-tetrahydroisoquinoline-3-hydroxamate]).

The protease inhibitor may be two or more protease inhibitors.

The two protease inhibitors may be an MMP general (pan) inhibitor and an MMP8 specific inhibitor.

The protease inhibitor may be added at a time of peak production of platelets within the culture.

The megakaryocytes or MPLs may be cultured in the presence of TPO or a TPO agonist to cause the formation of proplatelets, wherein the proplatelets release platelets. The megakaryocytes or MPLs are cultured in hematopoietic expansion medium and optionally in (1) TPO or a TPO agonist, SCF, IL-6 and IL-9 or (2) TPO or a TPO agonist, SCF, and IL-11 to cause the formation of pro-platelets in culture, wherein the pro-platelets release platelets.

The megakaryocytes or MPLs may be cultured at a temperature greater than 37° C. and equal to or less than 40° C.

The megakaryocytes or MPLs may be cultured at a temperature of about 39° C.

In another aspect, a method is provided for producing platelets from megakaryocytes or MPLs comprising culturing a non-adherent population of megakaryocytes or MPLs derived from iPS cells or ES cells at a temperature greater than 37° C. and equal to or less than 40° C., and harvesting and optionally isolating platelets from the culture.

The megakaryocytes or MPLs may be cultured at a temperature of about 39° C.

In another aspect, a method is provided for producing MPLs from PVE-HE cells comprising culturing a population of PVE-HE cells derived from iPS cells or ES cells in the presence of an inhibitor of BET, and harvesting and optionally isolating MPLs from the culture.

The inhibitor of BET may be I-BET151.

The inhibitor of BET may be added to the PVE-HE cells in the last 48 hours, last 36 hours, last 24 hours, last 18 hours, last 12 hours, or last 6 hours of culture.

In another aspect, a method is provided for producing MPLs from PVE-HE cells comprising culturing a population of PVE-HE cells derived from iPS cells or ES cells in the presence of a c-myc suppressor or inhibitor, and harvesting and optionally isolating MPLs from the culture.

The c-myc suppressor or inhibitor may be added to the PVE-HE cells in the last 48 hours, last 36 hours, last 24 hours, last 18 hours, last 12 hours, or last 6 hours of culture.

BRIEF DESCRIPTION OF THE FIGURES

FIG. 2A, after 48 hours attached cells show typical pluripotent stem cell morphology under feeder-free condition. FIG. 2B, the almost complete transition from pluripotent stem cell morphology into scattered small cell clusters is shown. FIG. 2C, after 96 to 146 hours post PVE-HE differentiation initiation, advanced differentiation morphology was observed showing small compact cell clusters growing on top of the monolayer.

(FIGS. 5A & 5C, indicated by arrows).

FIGS. 6A-6B show forward scatter ("FSC-A") and side scatter ("SSC-A") for donor-derived human platelets (6A), and hES-derived platelets (hES-PVE-HE-MLP) produced as described in Example 3 (6B). FIGS. 6C-E show expression of CD41a and CD42B by donor-derived human platelets (6C), iPS-derived platelets (iPS-PVE-HE-MLP) (6D), and hES-derived platelets (hES-PVE-HE-MLP) (6E), with the latter two samples having been produced as described in Example 3.

FIG. 12A shows representative images of thrombi formed in a mouse vessel wall injury model. FIG. 12B graphically illustrates the average number of platelets bound to the thrombus in each experiment. Platelet binding was inhibited by treatment with ReoPro, an anti-αIIbβIII antibody fragment, indicating that binding was dependent on αIIbβIII as expected. (FIG. 12B).

DETAILED DESCRIPTION OF INVENTION

Figure 1:
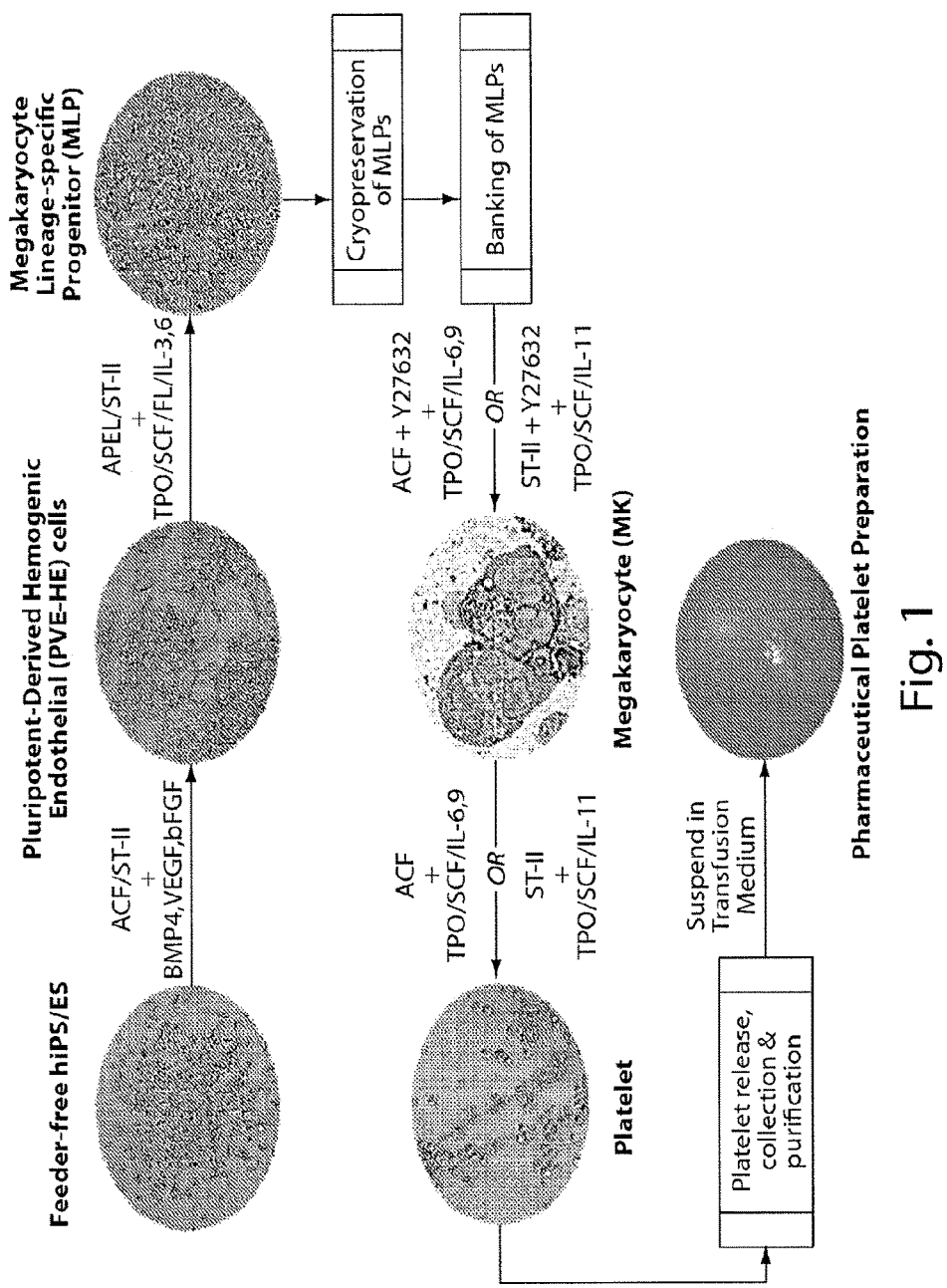
FIG. 1. Stepwise process depicting the generation of platelets from pluripotent stem cells. This Figure shows the progression of differentiation from pluripotent stem cells through pluripotent-derived hemogenic endothelial cells (PVE-HE) through megakaryocyte lineage-specific progenitor cells (MLP) and through megakaryocytes (MK).

Lists of definitions and abbreviations used in this disclosure are provided at the end of the detailed description.

As noted above, limitations in the supply of platelets can have potentially life-threatening consequences for transfusion-dependent patients. Pluripotent cells can be propagated in vitro indefinitely, and represent a potentially inexhaustible and donorless source of platelets for human therapy. The ability to create banks of hESC lines with matched or reduced incompatibility could potentially decrease or eliminate the need for immunosuppressive drugs and/or immunomodulatory protocols. Exemplary embodiments provide a method comprising producing patient-specific iPS cells (for example using methods herein described or any others known in the art), and producing patient-specific platelets from said patient-specific iPS cells, which platelets may be used for treatment of patients, such as patients who have developed or are at risk of developing platelet alloimmunity.

Exemplary embodiments provide an efficient method to generate megakaryocytes (MKs) from pluripotent stem cells under serum-free and feeder-free conditions. Preferably the MKs are produced from megakaryocyte lineage-specific progenitor cells (MLPs, which are further described herein). Preferably the MKs are not produced from hemangioblasts or hemangio-colony forming cells such as those disclosed in U.S. Pat. No. 8,017,393. Using methods disclosed herein, pluripotent stem cells (iPSC and ESCs) were directed towards MK differentiation. The efficiency of differentiation of megakaryocytes from MLPs has been very high (up to 90%). Without further purification, 85% of live cells from the MK suspension cultures were CD41a+CD42b+ and the mature MKs were also CD29+ and CD61+. These in vitro-derived MK cells can undergo endomitosis and become mature, polyploid MKs. Importantly, proplatelet forming cells with elongated pseudopodia were observed at the late stage of MK culture, indicating that MKs generated in this system are able to undergo terminal differentiation and generate functional platelets under feeder-free conditions.

Described herein is an efficient system which is adaptable for large scale and efficient in vitro megakaryocyte production using iPSC or other pluripotent stem cells as source cells under controlled conditions. Additionally, the platelets may be produce in sufficient quantities to supplement or supplant the need for donor-derived platelets. Additionally, the disclosed methods may be utilized to produce platelets and platelet progenitor cells in a predictable manner, such that the cells may be produced "on demand" or in quantities desired to meet anticipated need. The cells expressed CD41a and CD42b, underwent endomitosis, and formed mature polyploid MKs. Upon further maturation, they generated functional or activated platelets that were stimulated by thrombin to become positive for cell adhesion molecules, CD62p and αIIbβIII (thought to occur by exposure of the PAC-1 binding site after conformational change of αIIbβIII upon activation, while CD62p is thought to be exposed on outside membrane due to granule release). Both of these markers are known to be expressed on the surface of activated platelets and were detected on the hiPSC-PLTs using a PAC-1 and CD62p (p-selectin) binding assay. Because no stromal inducer cells are needed for megakaryocyte production, the methods described herein can provide for feeder-free platelet generation, such as platelet generation without any use of xenogeneic cells.

In exemplary embodiments, additional factors including estradiol, vitamin B3, matrix metalloproteinase inhibitors (MMP), inhibitors of c-myc expression, and extracellular matrix proteins may also be used to enhance platelet production, such as by stimulating megakaryocyte maturation and/or stimulating platelet production, which may be carried out in the absence of stromal cells.

The production of megakaryocytes under serum-free and stromal free conditions may allow screening for factors that are critical in regulating megakaryopoiesis and thrombopoiesis under well-defined conditions. Factors so identified may contribute to clinical applications. Advances in this area may also likely provide insights into the cellular and molecular mechanisms regulating different aspects of megakaryopoiesis including lineage commitment, expansion and maturation.

Exemplary embodiments integrate step-wise inductions of megakaryocyte differentiation from pluripotent stem cells. Further optimization and establishment of in-process controls can be performed to improve the consistency and efficiency of this system for clinical applications. The underlying cellular or extra-cellular mechanisms regulating megakaryocyte maturation need not be completely defined in order to practice these methods. Other factors that promote polyploidization and cytoplasmic maturation may be identified and included to facilitate the terminal differentiation of in vitro-derived megakaryocytes. For instance, at least one ROCK kinase inhibitor may be used to induce endomitosis of megakaryocytes at an early stage. However, this effect is thought to be likely due to an artificial blocking of chromosome segregation and cytokinesis rather than an orchestrated cellular and nuclear maturation of a differentiating megakaryocyte. It may be advantageous to reach a balance between the expansion, endomitosis and the cytoplasmic maturation to achieve the highest in vitro megakaryocyte yields, terminal differentiation status and downstream production of functional platelets under defined conditions.

These current results demonstrated that platelets derived from pluripotent stem cells share morphological and functional properties of normal blood platelets. These pluripotent stem cell derived human platelets are able to function in vivo as well.

Additional hemodynamic events may occur during the generation and propagation of platelet thrombi in the living organism which may not be fully mimicked by in vitro systems. The availability of intravital imaging technology provides a means to directly examine and quantify the platelet-dependent thrombotic process that occurs after vascular injury in complex in vivo systems. Using intravital high-speed widefield microscopy, the inventors demonstrated that pluripotent stem cell-derived platelets are incorporated into the developing mouse platelet thrombus at the site of laser-induced arteriolar wall injury in living mice similarly to normal human blood platelets. Pretreatment of the pluripotent cell-derived and control platelets with Reo-Pro markedly reduced the number of both donated and pluripotent stem cell-derived platelets incorporating in the thrombi, confirming the binding was mediated by αIIbβIII integrin. These results indicate that pluripotent stem cell-derived platelets are functional at the site of vascular injury in living animals.

Platelets are anucleate cells that adhere to tissue and to each other in response to vascular injury. This process is primarily mediated by the platelet integrin αIIbβIII, which binds to several adhesive substrates such as von Willebrand Factor (vWF) and fibrinogen to bridge and further activate platelets in a growing thrombus (36). The results herein demonstrate that platelets generated from pluripotent stem cells are functionally similar to normal blood platelets both in vitro and in living animals. The pluripotent stem cell-derived platelets were shown to possess important functions involved in hemostasis, including the ability to aggregate when stimulated with physiological agonists. In addition, immunofluorescence and transmission electron microscopic results further demonstrate that platelets generated from pluripotent stem cells are similar to normal blood platelets.

As further described in the examples below, numerous similarities between pluripotent cell-derived platelets and purified normal human platelets were observed. These similarities include the following.

hiPSC-PLTs are discoid (as demonstrated by transmission electron microscopy)

hiPSC-PLTs are mostly ultrastructurally identical to circulating human PLTs (as demonstrated by transmission electron microscopy).

The size of hiPSC-PLTs is comparable to that of circulating human PLTs (2.38 μm±0.85 μm versus 2.27 μm±0.49 μm) as demonstrated by DIC and β1-tubulin IF microscopy)

hiPSC-PLTs were able to spread on glass and form both filopodia and lamelopodia as demonstrated by DIC live-cell microscopy images).

hiPSC-PLTs are anucleate—comparable to circulating human PLTs (as demonstrated by Hoechst labeling).

hiPSC-PLTs have a normal tubulin cytoskeleton relative to circulating human PLTs (as demonstrated by β-tubulin labeling).

hiPSC-PLTs have normal filamentous actin relative to circulating human PLTs (as demonstrated by phalloidin labeling).

hiPSC-PLTs have normal alpha-granule expression relative to circulating human PLTs (as demonstrated by TSP4 and PF4 labeling).

Another scientific and clinical issue is whether pluripotent stem cell-derived platelets are functional in the complex in vivo setting. A large number of experimental models were established in the past decade to investigate thrombus formation in mice, including the laser-injury thrombosis model recently used by several groups (37:38:39). The laser-induced thrombosis model initiates platelet thrombus formation as fast as 5-30 seconds following injury. Therefore, this model allows the monitoring of the real-time incorporation of rapidly cleared human platelets and hESC-PLTs into the developing mouse platelet thrombus, which involves a large number of signaling pathways, enzymatic cascades, as well as the interplay of a myriad of cellular and protein components. This model also mirrors the inflammatory reactions associated with thrombin-induced thrombosis.

Figure 12A:
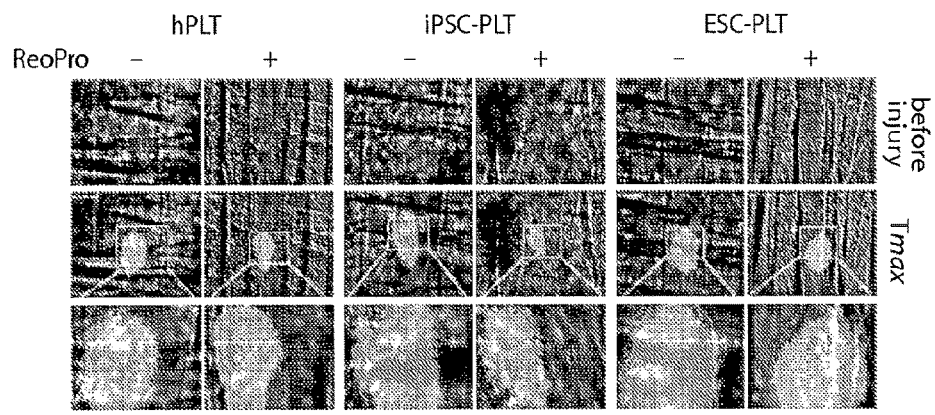
FIGS. 12A-12B. Functional comparison of circulating human platelets and platelets derived from human iPSCs and ESCs. These figures show the in vivo clot forming potential of circulating human platelets, hiPSC-PLTs and hESC-PLTs. Experiments were performed with natural human platelets ("hPLT"), iPSC-PLT, and hES cell derived platelets ("hESC-PLT").
Figure 12B:
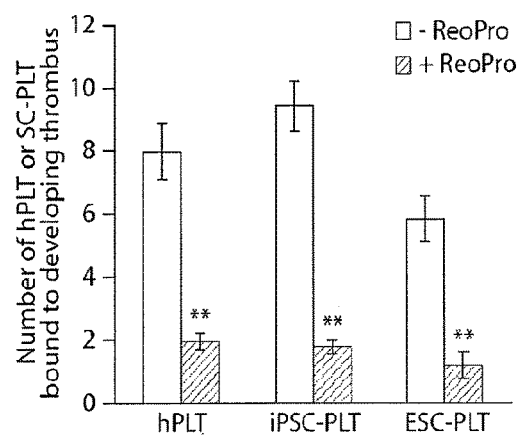

Using the laser-induced vessel injury model, the intravital microscopy analyses demonstrate that hiPSC-PLTs and hESC-PLTs, like blood platelets, are incorporated into the developing mouse platelet thrombus through αIIbβIII integrin following vascular injury (FIG. 12A). hiPSC-PLTs and hESC-PLTs functional capabilities were determined to be mediated by αIIbβIII by pretreatment with ReoPro, a Fab fragment of a human-murine chimeric monoclonal antibody that binds specifically to αIIbβIII and inhibits platelet function (FIG. 12B). These results provide evidence that hESC-PLTs are functional at the site of vascular injury in vivo. Importantly, it is shown for the first time that platelets derived from pluripotent stem cells under serum and feeder free conditions are able to facilitate coagulation and thrombus formation in vivo.

Two previous studies have reported the generation of MKs from hESCs. The yield in these systems is extremely low, and unlike the current system, relies on co-culture with animal stromal cells supplemented with serum (15,16). Moreover, in vivo functionality was not reported (15,16). The elimination of these two variables in pluripotent stem cell differentiation allows the generation of platelets without exposure to animal products. Additionally, the present disclosure demonstrates that the feeder-free system described herein can generate MKs with high efficiency and that functional platelets can be efficiently generated under the feeder-free conditions.

Thrombopoiesis is a highly complex process, with sophisticated reorganization of membrane and microtubules and precise distributions of granules and organelles (40). Despite recent advances in the understanding of platelet biogenesis, mechanistic details underlying membrane reorganization, initiation of proplatelets, transportation of platelet organelles and secretary granules, and control of platelet size remain to be elucidated. The ability to generate MKs under serum- and feeder-free conditions should aid in the screening of factors that are critical in regulating different aspects of megakaryopoiesis under well-defined conditions, including lineage commitment, expansion and maturation.

This disclosure provides various methods for producing PVE-HE cells, MLPs, MK, proplatelets and platelets in vitro (or ex vivo) that are iPS-derived or ESC-derived.

This disclosure provides methods for transitioning from an iPS cell or ES cell to a PVE-HE cell, or to a MLP, or to a MK, or to a platelet. This disclosure provides methods for transitioning from a PVE-HE cell to a MLP, or to a MK, or to a platelet. This disclosure provides methods for transitioning from a MLP to a MK, or to a platelet. This disclosure provides methods for transitioning from a MK to a platelet. These various cultures are described briefly below.

PVE-HE cells may be produced from iPS or ES cells through a method that comprises culturing iPS cells or ES cells in a culture medium comprising Iscove's Modified Dulbecco's Medium (IMDM) as basal medium, human serum albumin, iron-saturated transferrin, insulin, b-mercaptoethanol, soluble low-density lipoprotein (LDL), cholesterol, and further comprising bone morphogenetic protein 4 (BMP4) (e.g., at 50 ng/ml), basic fibroblast growth factor (bFGF) (e.g., at 50 ng/ml), and vascular endothelial growth factor (VEGF) (e.g., at 50 ng/ml). This culture period may last an average of 6 days.

MLPs may be produced from PVE-HE cells through a method that comprises culturing PVE-HE cells in a culture medium comprising Iscove's modified Dulbecco's medium (IMDM), Ham's F-12 nutrient mixture, Albucult (rh Albumin), Polyvinylalcohol (PVA), Linoleic acid, SyntheChol (synthetic cholesterol), Monothioglycerol (a-MTG), rh Insulin-transferrin-selenium-ethanolamine solution, protein-free hybridoma mixture II (PFHMII), ascorbic acid 2 phosphate, Glutamax I (L-alanyl-L-glutamine), Penicillin/streptomycin, and further comprising Stem Cell Factor (SCF) (e.g., at 25 ng/ml), Thrombopoietin (TPO) (e.g., at 25 ng/ml), Fms-related tyrosine kinase 3 ligand (FL) (e.g., at 25 ng/ml), Interleukin-3 (IL-3) (e.g., at 10 ng/ml), Interleukin-6 (IL-6) (e.g., at 10 ng/ml), and optionally Heparin (e.g., at 5 Units/ml). This culture period may last an average of 3-4 days. In the latter half of the culture, including in the last 48 hours, the last 36 hours, the last 24 hours, the last 18 hours, the last 12 hours, or the last 6 hours an inhibitor of BET may be added to the culture, preferably at sub-cytotoxic levels. The MLPs harvested from these cultures may be cryopreserved or used immediately for platelet production or other analysis.

Megakaryocytes may be produced from MLPs through a method that comprises culturing the MLPs in a medium that comprises Iscove's Modified Dulbecco's Medium (IMDM), human serum albumin, iron-saturated transferrin, insulin, b-mercaptoethanol, soluble low-density lipoprotein (LDL), cholesterol, and further comprises TPO (e.g., at 30 ng/ml), SCF (e.g., at 1 ng/ml), IL-6 (e.g., at 7.5 ng/ml), IL-9 (e.g., at 13.5 ng/ml), and optionally a ROCK inhibitor such as Y27632 (e.g., at 5 µM), and/or Heparin (e.g., at 5-25 units/nil).

Megakaryocytes may be produced from MLPs through a method that comprises culturing the MLPs in a medium that comprises Iscove's Modified Dulbecco's Medium (IMDM), human serum albumin, iron-saturated transferrin, insulin, b-mercaptoethanol, soluble low-density lipoprotein (LDL), cholesterol, and further comprises one or more of TPO (e.g., at 10-100 ng/ml), SCF (e.g., at 0.5-100 ng/ml), IL-11 (e.g., at 5-25 ng/ml), and optionally a ROCK inhibitor such as Y27632 (e.g., at 5 µM), and/or Heparin (e.g., at 2.5-25 Units/nil).

This latter culture produces MK and platelets depending on the length of the culture. Platelets are typically observed by about days 3-4 of culture. It will be understood that during the culture period the MLP will be maturing into MK, and the MK will be maturing into proplatelets, and the proplatelets will be maturing into platelets.

Platelets therefore may be produced from MLPs or MKs through a method that comprises culturing the MLPs or MKs in a medium that comprises Iscove's Modified Dulbecco's Medium (IMDM), human serum albumin, iron-saturated transferrin, insulin, b-mercaptoethanol, soluble low-density lipoprotein (LDL), cholesterol, and further comprises TPO (e.g., at 30 ng/ml), SCF (e.g., at 1 ng/ml), IL-6 (e.g., at 7.5 ng/ml), IL-9 (e.g., at 13.5 ng/ml), and optionally a ROCK inhibitor such as Y27632 (e.g., at 5 µM), and/or Heparin (e.g., at 5-25 units/nil). These culture period may be 4-8 days in length, or more.

Platelets may be produced from MLPs or MKs through a method that comprises culturing the MLPs or MKs in a medium that comprises Iscove's Modified Dulbecco's Medium (IMDM), human serum albumin, iron-saturated transferrin, insulin, b-mercaptoethanol, soluble low-density lipoprotein (LDL), cholesterol, and further comprises one or more of TPO (e.g., at 10-100 ng/ml), SCF (e.g., at 0.5-100 ng/ml), IL-11 (e.g., at 5-25 ng/ml), and optionally a ROCK inhibitor such as Y27632 (e.g., at 5 µM), and/or Heparin (e.g., at 2.5-25 Units/nil).

These platelet production methods include culture of MLP or MK under static or shear force culture conditions. A static culture condition is a culture condition in which the culture medium in contact with the cultured cells is relatively static. A shear force culture condition is a culture condition that comprises deliberate and constant movement of culture medium in contact with the cultured cells. Shear force is measured in dynes/cm$^2$. In some instances, the shear force approximates the shear force that occurs in the hematopoietic environment of the bone marrow. The shear force in the BM sinusoid has been reported to be about 1.3 to 4.1 dynes/cm$^2$. The disclosure contemplates that a shear force culture may be carried out at a shear force ranging from about 1 to about 4.5 dynes/cm$^2$, or about 1.3 to about 4.1 dynes/cm$^2$, including at any force or any range of forces therebetween including about 1.5, about 2.0, about 2.5, about 3.0, about 3.5, about 4.0, and about 4.1 dynes/cm$^2$.

It will be understood that the culture may be carried out at a flow rate that yields such shear forces. For a given culture, the shear force is associated with flow rate (volume/time). Shear force can be determined with knowledge of the flow rate, for any given culture or culture device, using knowledge in the art. Some of the experimental results provided herein compare platelet production in a given microfluidic device at flow rates of 12 microliters/min and 16 microliters/min. In some instances, the flow rate may be in the range of 5-25 microliters/min, or within 10-20 microliters/min. In some instances, the flow rate may be in the range of 10-15 microliters/min and in others it may be in the range of 16-20 microliters/min.

Where a shear force culture is used, the platelet production method may comprise a first culture period in a static culture for 3-4 days, or until platelets are observed, followed by a second culture in a shear force environment such as a microfluidic device or other device capable of inducing a shear force.

It is to be understood that aliquots may be harvested from such cultures and measured for platelet content using for example FACS. This will identify periods of peak platelet production.

It is also be understood that platelet production methods often times have as a starting material a mixture of MLPs and MK, or comprise in their culture medium at some point during the culture period a mixture of MLPs and MK.

The disclosure contemplates that the MLP or MK cultured in microfluidic devices or other culture devices in which a shear force condition can be achieved. In some instances, the device is designed such that the MLP or MK are immobilized within but not attached to the device. In some instances, the device is made of a synthetic resin such as polydimethylsiloxane (PDMS) or dimethicone. These are commonly used in microfluidic devices and chips.

The disclosure further contemplates that, when platelets are produced using shear force culture conditions, better platelet yields and functionality is obtained if particular protease inhibitors are added to the culture. It was found according to this disclosure that when platelets are placed under shear force cell surface CD42b can be lost from the platelet surface rendering the platelet less active. To avoid this and yet still reap the benefits of a shear culture, the disclosure contemplates using a protease inhibitor that prevents the shearing or loss of CD42b. Examples of such inhibitors include metalloprotease inhibitors and more specifically matrix metalloprotease (MMP) inhibitors. Another example of inhibitors that may be used in the shear culture is plasminogen activator inhibitors. These inhibitors may be pan inhibitors, intending that a single inhibitor may inhibit more than one and possibly all proteases within the class. Alternatively, they may be specific inhibitors, intending that a single inhibitor inhibits one protease within the class altogether or predominantly.

In some instances, the cultures are performed in the presence of an MMP inhibitor. The inhibitors may be small molecules such as small organic molecules, antibodies or antibody fragments, antisense or RNAi nucleic acids, and the like.

Examples of MMP inhibitors include, but are not limited to, GM6001 (a pan inhibitor), N-Dansyl-D-phenylalanine, 4-epi-Chlortetracycline, Hydrochloride Pyridoxatin, ARP 100, ARP 101, Batimastat, Chlorhexidine, Dihydrochloride, cis-ACCP, CL 82198 hydrochloride, Minocycline, Hydrochloride, Alendronate, Sodium Salt, GM 1489, TAPI-1, TAPI-2, GM 6001, Marimastat, MMP Inhibitor II, MMP Inhibitor III, EGTA, MMP Inhibitor V, MMP-13 Inhibitor, MMP-2 Inhibitor I, MMP-2 Inhibitor II, CP 471474, MMP-2/MMP-3 Inhibitor I, MMP-2/MMP-3 Inhibitor II, MMP-2/MMP-9 Inhibitor I, MMP-2/MMP-9 Inhibitor II, MMP-2/MMP-9 Inhibitor V. Ecotin, E. coli, MMP-3 Inhibitor, MMP-3 Inhibitor III, MMP-3 Inhibitor IV, Actinonin, MMP-3 Inhibitor V, MMP-3 Inhibitor VIII, MMP-7 Antisense Oligonucleotide, Sodium Salt, MMP-8 Inhibitor I, MMP-9 Inhibitor I, MMP-9/MMP-13 Inhibitor I, MMP-9/MMP-13 Inhibitor II, NNGH, NSC 23766, PD166793, Pro-Leu-Gly hydroxamate hydrochloride, Ro 32-3555, PF-356231, SB-3CT, Phosphoramidon, WAY 170523, UK 370106, UK 356618, Barium chloride dehydrate, Luteolin, Isobavachalcone, Doxycycline Hyclate, Collagenase Inhibitor I, o-Phenanthroline, and TAPI-0 from Santa Cruz Biotechnology, Inc. They also include TIMP-1, TIMP-2, TIMP-3, TIMP-4, GM6001, methylprednisolone, batimastat, marimastat, prinomastat, BAY 12-9566, MMI270(B), BMS-275291, metastat and other inhibitors of MMP-1 through MMP-26. It is to be understood that a MMP inhibitor may inhibit only one MMP family member or it may inhibit more than one or all MMP family members.

Certain synthetic MMP inhibitors generally contain a chelating group that binds the catalytic zinc atom at the MMP active site tightly. Common chelating groups include hydroxamates, carboxylates, thiols, and phosphinyls.

Other MMP inhibitors include BB-94, Ro 32-3555, BB-1101, BB-2516, SE205, CT1746, CGS 27023A, AG3340, BAY 12-9566, D2163, D1927, PNU-142372, CMT-1, and actinonin.

Many MMP inhibitors are commercially available.

The art is familiar with MMP inhibitors, and further examples are provided in U.S. Pat. Nos. 4,877,805; 5,837,224; 6,365,630; 6,630,516; 6,683,069; 6,919,072; 6,942,870; 7,094,752; 7,029,713; 6,942,870; 6,919,072; 6,906,036; 6,890,937; 6,884,425; 6,858,598; 6,759,432; 6,750,233; 6,750,228; 6,713,074; 6,699,486; 6,645,477; 6,630,516; 6,548,667; 6,541,489; 6,379,667; 6,365,630; 6,130,254; 6,093,398; 5,962,466; 5,837,224; 7,705,164; 7,786,316; 8,008,510; 7,579,486; 8,318,945; and 7,176,217; published U.S. patent applications 20070037253; 20060293345; 20060173183; 20060084688; 20050058709; 20050020607; 20050004177; 20040235818; 20040185127; 20040176393; 20040067883; 20040048852; 20040034098; 20040034086; 20040034085; 20040023969; 20040019055; 20040019054; 20040019053; 20040006137; 20040006077; 20030212048; 20030004165; 20020198176; 20020177588; 20020169314; 20020164319; 20020106339; 20020061866; 20020054922; 20020049237; 20020010162; 20010039287; and 20010014688; and published PCT applications WO 02/064552, WO 05/1103399, WO 06/028523, WO2008/024784, WO 02/064552, WO 05/110399, WO 06/028523, WO01/62261, and WO2008/024784, each of which is incorporated herein by reference.

MMP inhibitors have also been described in the scientific literature, see, for example, Whittaker et al. Chem Rev. 99:2735-2776, 1999; Whittake et al. Celltransmissions 17(1):3-14 (Table AB) and Harrison, Nature Reviews Drug Discovery 6:426-427, 2007 (Table AC), the specific teachings of which are incorporated herein by reference.

Some MMP inhibitors may be

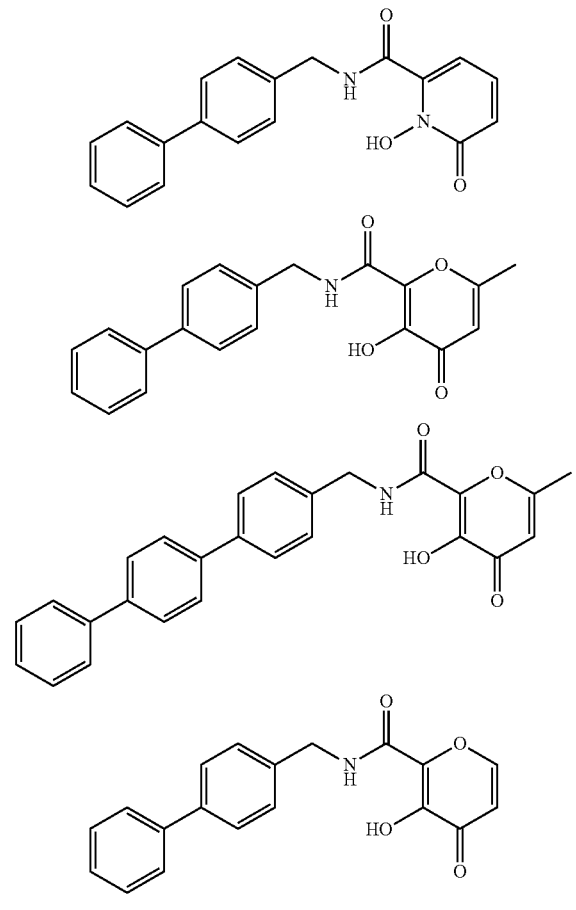

In some instances, an MMP8 inhibitor such as specific MMP8 inhibitor may be used in a static or a shear force culture. In some instances, the MMP8 inhibitor may be used in cultures of naturally occurring MLP and MK, such as bone marrow or umbilical cord blood derived MLP (e.g., $CD34^+$ progenitor cells) or MK.

An example of an MMP8 specific inhibitor is MMP8-I having chemical name (3R)-(+)-[2-(4-Methoxybenzenesulfonyl)-1,2,3,4-tetrahydroisoquinoline-3-hydroxamate], and which is commercially available from Millipore.

In some instances, the protease inhibitor may be a plasminogen activator inhibitor. Examples of plasminogen activator inhibitors include, but are not limited to, plasminogen activator inhibitor 1 (PAI-1), plasminogen activator inhibitor 2 (PAI-2), and tissue plasminogen activator (tPA) inhibitor. Other plasminogen activator inhibitors include those described in U.S. Pat. No. 4,923,807; international PCT applications WO/13063331; WO/1316974; and literature references Fortenberry Y M. Plasminogen activator inhibitor-1 inhibitors: a patent review (2006-present). Expert Opin Ther Pat. 2013 July; 23(7):801-15; and Pannekoek et al., EMBO J. 1986; 5(10):2539-44 each of which is incorporated herein by reference.

In some instances, two or more protease inhibitors may be used together in a culture. As an example, the MMP inhibitor GM6001 may be used together with the MMP8 specific inhibitor MMP8-I.

In some instances, the cultures may be performed at a temperature above 37° C. The culture temperature may be in the range of 37° C. to 45° C., or 37° C. to 42° C. or 38° C. to 41° C., or 39° C. to 40° C., or about 39° C. or about 40° C. The culture is performed at the set temperature. Culture at a temperature above 37° C. is referred to herein as an elevated temperature culture.

In some instances, the method that produces MLPs from PVE-HE cells is performed in the presence of inhibitors of the BET family of bromodomain containing proteins. BET inhibitor may be any molecule or compound that inhibits a BET family member, and may be a nucleic acid such as DNA and RNA aptamer, antisense oligonucleotide, siRNA and shRNA, a small peptide, an antibody or antibody fragment, and a small molecule such as a small chemical compound. A BET inhibitor may prevent or reduce binding of the bromodomain of at least one BET family member to acetyl-lysine residues of proteins. It is to be understood that a BET inhibitor may inhibit only one BET family member or it may inhibit more than one or all BET family members.

Examples of BET inhibitors are described in US 2011143651, WO2009/084693A1, WO 2011143669, WO 2011143660, WO 2011054851, and JP 2008156311, which are incorporated herein by reference.

Examples of BET inhibitors known in the art include, but are not limited to, RVX-208 (Resverlogix), PFI-1 (Structural Genomics Consortium), OTX015 (Mitsubishi Tanabe Pharma Corporation), BzT-7, GSK525762A (iBET, Glaxo-SmithKline), JQ1 (Cell 2011 146(6):904-17), and the compounds below (WO 2011054851, GlaxoSmithKline):

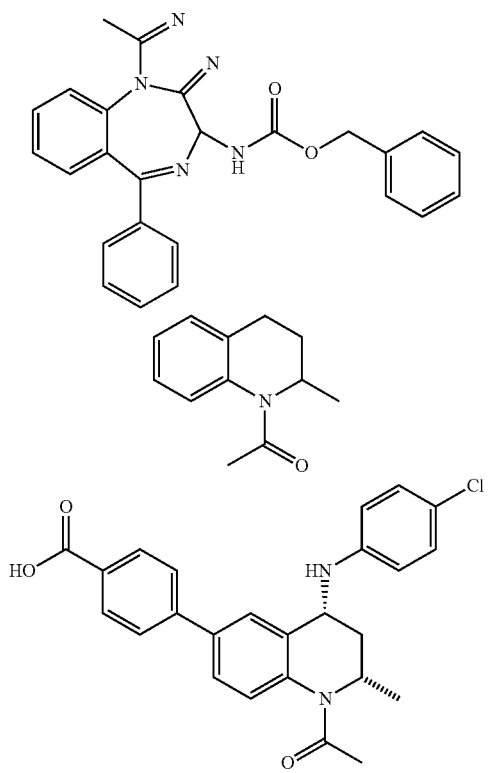

-continued

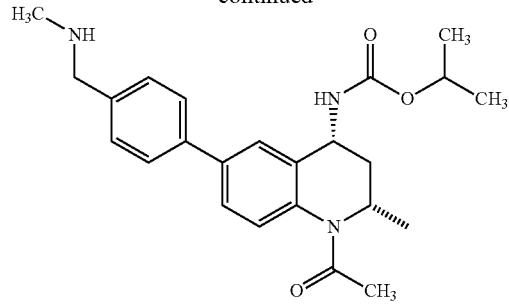

In some embodiments, the BET inhibitor is a small molecule compound (e.g., JQ1 or derivatives thereof) that binds to the binding pocket of the first bromodomain of a BET family member (e.g., BRD1, BRD2, BRD3, BRD4, BRD7, BRDT; see WO 2011143669). Other BET inhibitors include JQ1S, JQ1R, JQ20, JQ8, JQ6, JQ13, JQ19, JQ18, JQ11, JQ21, JQ24B, and KS1.

Another example of a BET inhibitor (referred to herein as iBET) is GSK1210151A (referred to herein as I-BET-151). Other BET inhibitors include IBET151 and IBET762.

Many BET inhibitors are useful as anti-leukemia agents. When used in the methods of this disclosure, they are typically used as low concentrations (i.e., below the level at which their cytotoxic effects are observed).

The disclosure contemplates that the BET inhibitors are used during the culture period that differentiates (or matures) PVE-HE cells to MLP. This culture period usually lasts about 4 days. The BET inhibitor is typically added in the latter half of the culture, including in the last 48 hours, last 36 hours, last 24 hours, last 12 hours, or last 6 hours of the culture.

Myc inhibitors include 10058-F4 and CX-3543.

Megakaryocyte Lineage Progenitors

Various embodiments of the present disclosure provide for a method of generating Megakaryocyte Lineage Progenitors (MLPs) from pluripotent stem cells (including human iPS and human ES), as well as compositions of MLPs.

Early lineage hemogenic endothelial cells are CD41a negative, expressing CD41a during late-stage hemogenic differentiation in hematopoietic progenitors. CD42b is expressed exclusively in mature megakaryocytes. MLP cultures may be heterogeneous with a high percentage of CD41+ cells and a low percentage of CD42+ cells.

MLPs may be assessed for the percentage of CD41a and CD42b doubly positive cells by FACS analysis. CD41a is a subunit of fibrinogen receptor ($\alpha IIb\beta III$) and CD42b is a subunit on von Willebrand Factor receptor (GPIb-V-IX). The expression of both receptors is specific for megakaryocyte lineages and both are thought to be required for platelet function.

Prior to harvesting for cryopreservation MLPs may be assessed for the approximate percentage of attached cells and the extent of differentiated large cells with low nuclei to cytoplasm ratio. Attached cells may appear as diffuse colonies with no clear colony borders. There may be an abundance of the floating MLPs resting on top of the attached cell population. Viable floating MLPs may appear clear, with minimal birefringence, demarked by a smooth cell membrane.

MLPs and compositions thereof may optionally be provided as a cryopreserved composition.

In another embodiment, the present disclosure provides for a method of screening for a modulator of cellular differentiation comprising: providing a quantity of PVE-HE cells or megakaryocytes progenitors (MLPs); contacting the PVE-HE cells or MLPs with a test compound; and determining the presence or absence of a functional effect from the contact between the PVE-HE cells or MLPs and the test compound, wherein the presence of a functional effect indicates that the test compound is a megakaryopoietic, thrombopoietic, and/or hematopoietic factor that modulates cellular differentiation and the absence of a functional effect indicates that the test compound is not a megakaryopoietic, thrombopoietic, and/or hematopoietic factor that modulates cellular differentiation. In other embodiments, megakaryopoietic, thrombopoietic, and/or hematopoietic factors relate to the expansion, endomitosis, cytoplasmic maturation, and terminal differentiation of functional platelets.

Megakaryocytes

Various embodiments of the present disclosure provide for a method of generating megakaryocytes from pluripotent stem cells (including human iPS and human ES) under stromal-free conditions and/or under serum-free conditions. These embodiments include generating megakaryocytes. Further embodiments provide for a method of generating megakaryocytes from pluripotent derived hemogenic endothelial cells. Said megakaryocytes are preferably able to produce platelets, e.g., when cultured under the conditions as described herein.

In one embodiment, the method comprises: providing pluripotent stem cells; and differentiating the pluripotent stem cells into megakaryocytes. In one embodiment, the pluripotent stem cells are human cells. In another embodiment, the pluripotent stem cells are hESC optionally produced without the destruction of the embryo such as the NED7 line. In another embodiment, the pluripotent cells are human ES cells. In another embodiment, the megakaryocytes are derived from induced pluripotent stem cells. In another embodiment, the pluripotent stem cells are human iPS cells derived from reprogramming somatic cells. In one embodiment, the somatic cells are from fetal tissue. In another embodiment, the somatic cells are from adult tissue.

In another embodiment, the present disclosure provides for a method of screening for a modulator of cellular differentiation comprising: providing a quantity of megakaryocytes (MKs); contacting the MKs with a test compound; and determining the presence or absence of a functional effect from the contact between the MKs and the test compound, wherein the presence of a functional effect indicates that the test compound is a megakaryopoietic, thrombopoietic, and/or hematopoietic factor that modulates cellular differentiation and the absence of a functional effect indicates that the test compound is not a megakaryopoietic, thrombopoietic, and/or hematopoietic factor that modulates cellular differentiation. In other embodiments, megakaryopoietic, thrombopoietic, and/or hematopoietic factors relate to the expansion, endomitosis, cytoplasmic maturation, and terminal differentiation of functional platelets.

Platelets

Other embodiments of the present disclosure provide for a method of generating platelets from human embryonic stem cells and pluripotent stem cells (including iPSC and human iPSC). In one embodiment, the method comprises: providing human embryonic stem cells (hESCs); forming PVE-HE cells differentiating the PVE-HE cells into megakaryocytes; and differentiating the megakaryocytes into platelets.

In another embodiment, the method of generating platelets comprises: providing PVE-HE cells; differentiating the PVE-HE cells into MLPs or megakaryocytes; and optionally differentiating the MLPs into megakaryocytes; and then differentiating (or maturing) the megakaryocytes into platelets, typically through a proplatelet step. The process of differentiating the PVE-HE cells into megakaryocytes can be performed as described above. In one embodiment, the PVE-HE cells are derived from human ES cells. In another embodiment, the PVE-HE cells are derived from induced pluripotent stem cells (iPSCs). In one embodiment, the iPS cells are human iPS cells derived from reprogramming somatic cells. In one embodiment, the somatic cells are from fetal tissue. In another embodiment, the somatic cells are from adult tissue. In various embodiments, the process of differentiating the megakaryocytes into platelets comprises continuing to culture the megakaryocytes to allow the megakaryocytes to differentiate into platelets. In various embodiments, the process of differentiating the megakaryocytes into platelets is under feeder free conditions and comprises collecting the megakaryocytes differentiated from megakaryocyte-lineage specific progenitor cells.

In further embodiments, platelets are collected from Day 4 to Day 10 of megakaryocyte culture in MK-M medium or other medium comprising Iscove's Modified Dulbecco's Medium (IMDM) as basal medium, human serum albumin, iron-saturated transferrin, insulin, b-mercaptoethanol, soluble low-density lipoprotein (LDL), cholesterol, TPO (e.g., at 30 ng/ml), SCF (e.g., at 1 ng/ml), IL-6 (e.g., at 7.5 ng/ml), IL-9 (e.g., at 13.5 ng/ml), and optionally a ROCK inhibitor such as Y27632 (e.g., at 5 µM), and/or Heparin (e.g., at 5-25 units/ml). In a preferred embodiment, platelets are collected from 3-5 days after the first emergence of proplatelet forming cells in the megakaryocyte culture in MK-M medium. In certain embodiments, the platelets are purified using density gradient centrifugation. In further embodiments, the density gradient centrifugation uses Percoll medium. In further embodiments, the density gradient centrifugation uses BSA/HSA medium. In another embodiment, the platelet purification method separates particles that are CD41a negative. In another embodiment, the platelet purification method separates particles that are CD42b negative. In another embodiment, the platelet purification method retains cell viability and morphological integrity. In other embodiments, the platelets express CD41a and CD42b. In other embodiments, the platelets are responsive to thrombin stimulation. In another embodiment, the platelets are able to spread on fibrinogen and von Willebrand Factor (vWF) surfaces. In additional embodiments, the platelets have capacity for PAC-1 binding and integrin activation. In another embodiment, the platelets form micro-aggregates and facilitate clot formation and retraction. In another embodiment, the platelets are not activated in the presence of apyrase and/or EDTA.

Various embodiments of the present disclosure provide for a method of using pluripotent stem cell-derived platelets. In certain embodiments, the pluripotent stem cell-derived platelets are used in platelet transfusions. The method may comprise providing a quantity of pluripotent stem cell-derived platelets; and administering the quantity of pluripotent stem cell-derived platelets to a subject in need thereof. In various embodiments the pluripotent stem cell-derived platelets can be patient-matched platelets. In another embodiment, the platelets are derived from iPSCs. In a certain embodiment, the platelets are derived from human iPS cells. In other embodiments, the platelets are stored in a solution that does not contribute to an HLA alloimmunogenic response in a subject upon administration of the platelets to the subject. In additional exemplary embodiments, the pluripotent stem cell-derived platelets may be substantially free of leukocytes, for example containing less than 5%, less than 4%, less than 3%, less than 2%, or less than 1% leukocytes, preferably less than 0.1%, 0.001% or even 0.0001%. Additional exemplary embodiments provide a preparation of pluripotent stem cell-derived platelets which contains less than $10^6$ leukocytes in the preparation, more preferably less than $10^5$, $10^4$, or even $10^3$ leukocytes.

Additional exemplary embodiments provide a composition containing at least $10^8$ platelets, more preferably at least $10^9$, at least $10^{10}$, or at least $10^{11}$ platelets.

Using the current blood bank storage conditions at 22-24° C., the viability and function of human platelets (collected by aphaeresis) can be maintained for only 5 days—the limited storage time though to be due to aging of the platelets and an increasing risk of bacterial proliferation. It is expected that platelets produced by the methods of the present invention will have a longer shelf life than banked platelets, such as being able to be maintained for at least 6, 7, 8, 9, 10, 11, 12, 13, 14 or even 15 days at 22-24° C. and maintain appropriate viability to be used in human patients.

In certain embodiments, the platelets can be treated—after isolation or during one or more of the culturing steps leading to platelet production—with one or more agents that prolong platelet storage at 22-24° C., refrigerated (e.g., 4° C.) and/or frozen.

For example, the present invention contemplates treating the platelets with agents, or deriving the platelets under conditions, that reduce sialidase activity and (optionally) inhibit proliferation of one or more bacteria in a platelet product preparation. The method can include the steps of contacting the platelet product preparation with an amount of a sialidase inhibitor, to thereby obtain a sialidase treated platelet product preparation; wherein the sialidase activity is reduced and the proliferation of one or more bacteria is inhibited, as compared to a platelet product preparation not subjected to a sialidase inhibitor.

The type of bacteria inhibited include those commonly found in platelet product preparations. Examples of such bacteria include: *Aspergillus, Bacillus* sp, *Bacteroides eggerthii, Candida albicans, Citrobacter* sp, *Clostridium perfringens, Corynebacterium* sp, *Diphtheroid, Enterobacter aerogenes, Enterobacter amnigenus, Enterobacter cloacae, Enterococcus avium, Enterococcus faecalis, Escherichia coli, Fusobacterium* spp., *Granulicatella adiacens, Heliobacter pylori, Klebsiella* sp, (*K. pneumonia, K. oxytoca*), *Lactobacillus* sp, *Listeria* sp, *Micrococcus* sp, *Peptostreptococcus, Proteus vulgaris, Pseudomonas* sp, *Pseudomys oxalis, Propionibacterium* sp, *Salmonella* sp, *Serratia* sp, *Serratia marcescens Staphylococcus* sp (*Coagulase-negative Staphylococcus, Staphylococcus epidermidis, Staphylococcus aureus*), *Streptococcus* sp, (*S. gallolyticus, S. bovis, S. pyogenes, S. viridans*), and *Yersinia enterocolitica.*

The sialidase inhibitors that can be used with the present invention include, e.g., fetuin, 2,3-dehydro-2-deoxy-N-acetylneuraminic acid (DANA) or a pharmaceutically acceptable salt thereof; ethyl (3R,4R,5S)-5-amino-4-acetamido-3-(pentan-3-yloxy)-cyclohex-1-ene-1-carboxylate); (2R,3R,4S)-4-guanidino-3-(prop-1-en-2-ylamino)-2-((1R, 2R)-1,2,3-tr-hydroxypropyl)-3,4-dihydro-2H-pyran-6-carboxylic acid; (4S,5R,6R)-5-acetamido-4-carbamimidamido-6-[(1R,2R)-3-hydroxy-2-methoxypropyl]-5,6-dihydro-4H-pyran-2-carboxylic acid; and (1S,2S,3S,4R)-3-[(1S)-1-acetamido-2-ethyl-butyl]-4-(diaminomethylideneami-no)-2-hydroxy-cyclopentane-1-carboxylic acid, or a pharmaceutically acceptable salt thereof.

One or more glycan-modifying agents can be added to the platelets. Such glycan modifying agents include, for example, CMP-sialic acid, a CMP-sialic acid precursor, UDP galactose or a combination thereof. In an aspect, an enzyme that converts the CMP-sialic acid precursor to CMP-sialic acid can also be added to the platelets.

In certain embodiments, the platelets can be treated with at least one glycan modifying agent in an amount effective to reduce the clearance of the population of platelets. In some embodiments, the glycan modifying agent is selected from the group consisting UDP-galactose and UDP-galactose precursors. In some preferred embodiments, the glycan modifying agent is UDP-galactose.

In certain embodiments, the platelets can be treated with certain sugar molecules which lead to glycation of the exposed GlcNAc residues on GP1b and thereby reduced platelet clearance, block platelet phagocytosis, increase platelet circulation time, and/or increase platelet storage time.

In certain embodiments, the platelets can be treated with trehalose or other low molecular weight polysaccharides.

In certain embodiments, the platelets can be treated with protease inhibitors, such as matrix metalloprotease inhibitors.

In some embodiments, the in vivo circulation time of the platelets is increased by at least about 10%, 15%, 20%, 25%, 30%, 40%, 50%, 60%, 75%, 100%, 150%, 200%, or more The platelets of the present invention can be stored chilled for at least about 3 days, at least about 5 days, at least about 7 days, at least about 10 days, at least about 14 days, at least about 21 days, or at least about 28 days.

Further, deriving platelets from stem cells in culture affords the opportunity to precondition the platelets and the megakaryocytes, and even to genetically modify the stem cells or progenitor cells like the megakaryocytes in a manner that extends the shelf-life of the platelets and enhances yield and viability after refrigeration and/or cryopreservation storage. For instance, the MKs can be engineered to have altered levels of expression of genes involved in membrane lipid ratios, protein glycosylation patterns, stress-induced proteins, 14-3-3ζ translocation and the like.

In a further embodiment, the platelets are functional platelets. In a further embodiment the percentage of functional platelets is at least about 60%, is at least about 70%, is at least about 80% or is at least about 90%. In a yet further embodiment, the functional platelets are active for at least 2 days when stored at 22-37° C.

The disclosure further contemplates that the platelets generated according to the methods provided herein can be engineered to include one or more therapeutic agents which are released by the platelets either in a passive manner (e.g., they may diffuse out of the platelet over time) or in an active manner (e.g., are released upon activation and degranulation of platelets). A wide range of drugs can be used, and may include an antibiotic, anti-viral agent, anesthetic, steroidal agent, anti-inflammatory agent, anti-neoplastic agent, antigen, vaccine, antibody, decongestant, antihypertensive, sedative, birth control agent, progestational agent, anticholinergic, analgesic, anti-depressant, anti-psychotic, β-adrenergic blocking agent, diuretic, cardiovascular active agent, vasoactive agent, non-steroidal anti-inflammatory agent, nutritional agent, etc.

For example, the engineered platelets may be prepared so that they include one or more compounds selected from the group consisting of drugs that act at synaptic and neuroeffector junctional sites (e.g., acetylcholine, methacholine, pilocarpine, atropine, scopolamine, physostigmine, succinylcholine, epinephrine, norepinephrine, dopamine, dobutamine, isoproterenol, albuterol, propranolol, serotonin); drugs that act on the central nervous system (e.g., clonazepam, diazepam, lorazepam, benzocaine, bupivacaine, lidocaine, tetracaine, ropivacaine, amitriptyline, fluoxetine, paroxetine, valproic acid, carbamazepine, bromocriptine, morphine, fentanyl, naltrexone, naloxone); drugs that modulate inflammatory responses (e.g., aspirin, indomethacin, ibuprofen, naproxen, steroids, cromolyn sodium, theophylline); drugs that affect renal and/or cardiovascular function (e.g., furosemide, thiazide, amiloride, spironolactone, captopril, enalapril, lisinopril, diltiazem, nifedipine, verapamil, digoxin, isordil, dobutamine, lidocaine, quinidine, adenosine, digitalis, mevastatin, lovastatin, simvastatin, mevalonate); drugs that affect gastrointestinal function (e.g., omeprazole, sucralfate); antibiotics (e.g., tetracycline, clindamycin, amphotericin B, quinine, methicillin, vancomycin, penicillin G, amoxicillin, gentamicin, erythromycin, ciprofloxacin, doxycycline, acyclovir, zidovudine (AZT), ddC, ddI, ribavirin, cefaclor, cephalexin, streptomycin, gentamicin, tobramycin, chloramphenicol, isoniazid, fluconazole, amantadine, interferon); anti-cancer agents (e.g., cyclophosphamide, methotrexate, fluorouracil, cytarabine, mercaptopurine, vinblastine, vincristine, doxorubicin, bleomycin, mitomycin C, hydroxyurea, prednisone, tamoxifen, cisplatin, decarbazine); immunomodulatory agents (e.g., interleukins, interferons, GM-CSF, TNFα, TNFβ, cyclosporine, FK506, azathioprine, steroids); drugs acting on the blood and/or the blood-forming organs (e.g., interleukins, G-CSF, GM-CSF, erythropoietin, vitamins, iron, copper, vitamin B12, folic acid, heparin, warfarin, coumarin); hormones (e.g., growth hormone (GH), prolactin, luteinizing hormone, TSH, ACTH, insulin, FSH, CG, somatostatin, estrogens, androgens, progesterone, gonadotropin-releasing hormone (GnRH), thyroxine, triiodothyronine); hormone antagonists; agents affecting calcification and bone turnover (e.g., calcium, phosphate, parathyroid hormone (PTH), vitamin D, bisphosphonates, calcitonin, fluoride), vitamins (e.g., riboflavin, nicotinic acid, pyridoxine, pantothenic acid, biotin, choline, inositol, carnitine, vitamin C, vitamin A, vitamin E, vitamin K), gene therapy agents (e.g., viral vectors, nucleic-acid-bearing liposomes, DNA-protein conjugates, antisense agents); or other agents such as targeting agents etc.

In certain embodiments, the platelets have been engineered to include one or more therapeutic agents, such as a small molecule drug, apatamer or other nucleic acid agent, or recombinant proteins, i.e., which may be stored in the platelets' granules (α-granules, for example), and preferably released upon activation of the platelets, such as at the site of a vascular injury or other wound, atherosclerotic plaque or endothelial cell erosion, infection, or a prothrombotic environment capable of platelet activation, such as the vasculature of a solid tumor. In other embodiments, the engineered platelets can be used to reduce the severity of or prevent fibrosis, such as in the treatment of lung fibrosis, i.e., such as may be selected from the group consisting of pulmonary fibrosis, pulmonary hypertension, chronic obstructive pulmonary disease (COPD), asthma and cystic fibrosis.

In certain embodiments, the platelets include one or more exogenous agents which promote or accelerate normal wound healing, reduce scarring, reduce fibrosis, or a combination thereof. An exemplary recombinant protein which can be expressed in the megakaryocytes and packaged in the granules of the platelets produced therefrom include erythropoietin. Localized delivery of erythropoietin accelerates fibrin-induced wound-healing response, and recombinant EPO-loaded platelets can be used in treatments of open wounds and sores, including diabetic ulcers, burns, etc., as well as closed (internal) wounds including surgical procedures (surgical lesion, such as resulting from laminectomy, discectomy, joint surgery, abdominal surgery or thoracic surgery). Other wound-healing proteins, particularly non-fibrotic growth factors, for which expression in MK cells and storage in platelet granules can be accomplished according to the present invention include insulin-like growth factor 1 (IGF-1); Basic Fibroblast Growth Factor (bFGF); Transforming Growth Factor β-3 (TGFβ-3), granulocyte colony stimulating factor (GCSF), granulocyte macrophage colony stimulating factor (GMCSF), keratinocyte growth factor (KGF), fibronectin, vitronectin, thrombospondin, laminin, tenasin.

In certain embodiments, the platelets include one or more exogenous anti-fibrotic agents, such as, but not limited to include antibodies (particularly single chain antibodies) to TGFβ-1, TGFβ-2 and/or PDGF; binding proteins which prevent TGFβ-1, TGFβ-2 and/or PDGF from binding to their receptors by either binding to the growth factor itself or binding to the receptor (e.g., peptides containing the receptor binding site sequence) or soluble forms of growth factor receptor or the growth factor binding domains of these receptors; or aptamers which inhibitor receptor-ligand interaction.

In certain embodiments, the platelets include one or more exogenous agents which modulate wound healing, such as proteases; vasoactive substances such as serotonin and/or histamine; fibronectin; collagenases; plasminogen activator; neutral proteases; elastin; collagens; proteogycans; epidermal growth factor (EGF); hormones such as estradiol, testosterone or progesterone; macrophage derived growth factor (MDGF); adrenomedullin; angiogenin; angiopoietin-1; angiopoitin-related growth factor; brain derived neurotrophic factor; corticotropin-releasing hormone; Cyr16; follistatin; hepatocyte growth factor; interleukins; midkine; neurokinin A; neuropeptide Y (NPY); pleiotrophin; progranulin, prolifern; secretoneurin; substance P; VG5Q; and factors that recruit pericytes; and becaplermin.

In certain embodiments, the platelets include one or more nucleic apatamers that can promote wound healing and/or reduce fibrosis and scarring at the site of a wound. Scarring is believed to be caused by both persistent inflammation and overexuberant fibroblast activation. Osteopontin (OPN) is a cytokine that promotes cell activation. The absence of OPN in vivo reduces dermal scarring. RNA aptamers are short RNA molecules that bind target proteins with high affinity. The aptamer OPN-R3 (R3) blocks OPN signaling. In certain embodiments, the platelets can be loaded with OPN-R3 to be released actively or passively, preferably actively at the site to platelet activation. Exemplary OPN inhibitory apatmers are described in US20110190386.

In certain embodiments, the platelets include one or more small (organic) agents that can promote wound healing and/or reduce fibrosis and scarring at the site of a wound. Excisional wound closure, for example, can be significantly accelerated by A2A receptor agonists, such as CGS-21680 (Montesinos et al. JEM 1997, 186(9) pages 1615-1620). Accordingly, merely to illustrate, the platelets can be loaded with an A2A receptor agonists to be released actively or passively, preferably actively at the site to platelet activation. Other small molecule agents include steroids, non-steroidal antiinflammatory compounds (NSAID), 5-lipoxygenase (5-LO) inhibitors, leukotriene B4 (LTB4) receptor antagonists, leukotriene A4 (LTA4) hydrolase inhibitors, 5-HT agonists, 3-hydroxy-3-methylglutaryl coenzyme A (HMG-CoA) inhibitors, H2 antagonists, antineoplastic agents, and cyclooxygenase-2 inhibitors.

In certain embodiments, the platelets include one or more exogenous antibiotic agents. Exemplary antibiotics include chloramphenicol, chlortetracycline, clyndamycin, clioquinol, erythromycin, framycetin, gramicidin, fusidic acid, gentamicin, mafenide, mupiroicin, neomycin, polymyxin B, bacitracin, silver sulfadiazine, tetracycline, chlortetracycline, tobramycin, amikacin, vancomycin, ramoplanin, levofloxacin, ofloxacin, moxifloxacin, clindamycin or combinations thereof.

In certain embodiments, the platelets include one or more exogenous analgesic or anesthetic and/or anti-inflammatory agents. Exemplary anti-inflammatory agents can be selected from acetaminophen, aspirin, ibuprofen, diclofenac, indometacin, piroxicam, fenoprofen, flubiprofen, ketoprofen, naproxen, suprofen, loxoprofen, cinnoxicam, tenoxicam, and a combination thereof.

Platelets engineered to deliver antithrombotic/antirestenosis agents can be used during angioplasty and thrombolysis procedures.

In certain embodiments, the engineered platelets can be used to prevent or reduce the severity of atherosclerosis, and may include one or more exogenous anti-atherosclerosis agent (i.e., an agent that reduces atherosclerotic lesions or prevents formation), and may include: antiproliferative/antimitotic agents including natural products such as *vinca* alkaloids (i.e.vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (Cortisol, cortisone, fludrocortisone, prednisone, prednisolone, 6a-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

In certain embodiments, the engineered platelets can used to prevent or reduce the severity of restenosis, and may include one or more exogenous anti-antiproliferative substances, antiphlogistic as well as antithrombotic compounds are used as active agents. Exemplary active agents for restenosis include sirolimus, everolimus, somatostatin, tacrolimus, roxithromycin, dunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoboside, teniposide, nimustine, carmustine, lomustine, cyclophosphamide, 4-hydroxyoxycyclophosphamide, estramustine, melphalan, ifosfamide, tropfosfamide, chlorambucil, bendamustine, dacarbazine, busulfan, procarbazine, treosulfan, tremozolomide, thiotepa, daunorubicin, doxorubicin, aclarubicin, epirubicin, mitoxantrone, idarubicin, bleomycin, mitomycin, dactinomycin, methotrexate, fludarabine, fludarabine-5'-dihydrogenphosphate, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, pegasparase, anastrozole, exemestane, letrozole, formestane, aminogluteth-emide, adriamycin, azithromycin, spiramycin, cepharantin, smc proliferation inhibitor-2w, epothilone A and B, mitoxantrone, azathioprine, mycophenolatmofetil, c-myc-antisense, b-myc-antisense, betulinic acid, camptothecin, lapachol, β-lapachone, podophyllotoxin, betulin, podophyllic acid 2-ethylhydrazide, molgramostim, peginterferon α-2b, lenograstim; filgrastim, macrogol, dacarbazine, basiliximab, daclizumab, selectin, cytokine antagonist, CETP inhibitor, cadherines, cytokinin inhibitors, COX-2 inhibitor, NFκ.B, angiopeptin, ciprofloxacin, camptothecin, fluroblastin, monoclonal antibodies, which inhibit the muscle cell proliferation, bFGF antagonists, probucol, prostaglandins, 1,11-dimethoxycanthin-6-one, 1-hydroxy-11-methoxycanthin-6-one, scopolectin, colchicine, NO donors, pentaerythritol tetranitrate, syndnoeimines, S-nitrosoderivatives, tamoxifen, staurosporine, β-estradiol, α-estradiol, estriol, estrone, ethinylestradiol, fosfestrol, medroxyprogesterone, estradiol cypionates, estradiol benzoates, tranilast, kamebakaurin and other terpenoids, which are applied in the therapy of cancer, verapamil, tyrosine kinase inhibitors, tyrphostines, cyclosporine A, paclitaxel and derivatives thereof, baccatin, taxotere and other both synthetically and from native sources obtained macrocyclic oligomers of carbon suboxide (MCS) and derivatives thereof, mofebutazone, acemetacin, diclofenac, lonazolac, dapsone, o-carbamoylphenoxyacetic acid, lidocaine, ketoprofen, mefenamic acid, piroxicam, meloxicam, chloroquine phosphate, penicillamine, hydroxychloroquine, auranofin, sodium aurothiomalate, oxaceprol, celecoxib, β-sitosterin, ademetionine, myrtecaine, polidocanol, nonivamide, levomenthol, benzocaine, aescin, ellipticine, Calbiochem D-24851, colcemid, cytochalasin A-E, indanocine, nocadazole, S 100 protein, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plaminogen activator inhibitor-1, plasminogen activator inhibitor-2, antisense oligonucleotides, VEGF inhibitors, IGF-1, antibiotics, antithrombotics, argatroban, aspirin, abciximab, synthetic antithrombin, bivalirudin, coumadin, enoxoparin, desulphated and N-reacetylated heparin, tissue plasminogen activator, GpIIb/IIIa platelet membrane receptor, factor X a inhibitor antibody, hirudin, r-hirudin, PPACK, protamin, prourokinase, streptokinase, warfarin, urokinase, vasodilators, dipyramidole, trapidil, nitroprussides, PDGF antagonists, triazolopyrimidine and seramin, ACE inhibitors, captopril, cilazapril, lisinopril, enalapril, losartan, thioprotease inhibitors, prostacyclin, vapiprost, interferon α, β and γ, histamine antagonists, serotonin blockers, apoptosis inhibitors, apoptosis regulators, p65 NF-κ.B and Bc1-xL antisense oligonucleotides, halofuginone, nifedipine, tocopherol, tranirast, molsidomine, tea polyphenols, epicatechin gallate, epigallocatechin gallate, Boswellic acids and derivatives thereof, leflunomide, anakinra, etanercept, sulfasalazine, etoposide, dicloxacillin, tetracycline, triamcinolone, mutamycin, procainimid, retinoic acid, quinidine, disopyrimide, flecainide, propafenone, sotolol, amidorone, natural and synthetically obtained steroids, bryophyllin A, inotodiol, maquiroside A, ghalakinoside, mansonine, strebloside, hydrocortisone, betamethasone, dexamethasone, fenoporfen, ibuprofen, indomethacin, naproxen, phenylbutazone, antiviral agents, antimycotics, antiprozoal agents, natural terpenoids, hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-α-senecioyloxychaparrin, taxamairin A and B, regenilol, triptolide, cymarin, apocymarin, aristolochic acid, anopterin, hydroxyanopterin, anemonin, protoanemonin, berberine, cheliburin chloride, cictoxin, sinococuline, bombrestatin A and B, cudraisoflavone A, curcumin, dihydronitidine, nitidine chloride, 12-β-hydroxypregnadien-3,20-dione, bilobol, ginkgol, ginkgolic acid, helenalin, indicine, indicine-N-oxide, lasiocarpine, inotodiol, glycoside 1a, podophyllotoxin, justicidin A and B, larreatin, malloterin, mallotochromanol, isobutyrylmallotochromanol, maquiroside A, marchantin A, maytansine, lycoridicin, margetine, pancratistatin, liriodenine, bisparthenolidine, oxoushinsunine, aristolactam-AII, bisparthenolidine, periplocoside A, ghalakinoside, ursolic acid, deoxypsorospermin, psycorubin, ricin A, sanguinarine, manwu wheat acid, methylsorbifolin, sphatheliachromen, stizophyllin, mansonine, strebloside, akagerine, dihydrousambaraensine, hydroxyusambarine, strychnopentamine, strychnophylline, usambarine, usambarensine, berberine, liriodenine, oxoushinsunine, daphnoretin, lariciresinol, methoxylariciresinol, syringaresinol, umbelliferon, afromoson, acetylvismione B, desacetylvismione A, or vismione A and B.

In still other embodiments, the engineered platelets can used as part of a treatment for solid tumors. Solid tumors generate a prothrombotic environment capable of platelet activation. Recent findings indicate that the activated platelets are crucial regulators of tumor vascular homeostasis in that they prevent tumor hemorrhage. Surprisingly, this effect is independent of platelets' capacity to form thrombi and instead relies on the secretion of their granule content. Thus, using platelet secretory activities to target the release of antitumor and/or anti-angiogeneic agents represents an approach to specifically kill tumor cells and/or destabilize tumor vasculature. In certain preferred embodiments, the engineered platelets can be loaded with anti-angiogeneic agents and/or agents causing the disruption of tumor vascular structure.

To further illustrate, the engineered platelets can be loaded with such anticancer agents as anti-neoplastic or chemotherapeutic agents, which may include (a) alkylating agents, such as mechlorethamine, cyclophosphamide, ifosfamide, melphaan, chlorambucil, hexamethylmelamine, thiotepa, busulfan, carmustine, lomustine, semustine, streptozocin, dacarbazine, etc.; (b) antimetabolites, such as methotrexate, 5-FU, FudR, cytarabine, 6 MP, thioguanine, pentostatin, etc.; (c) natural products, such as taxol, vinblastine, vincristine, etoposide, teniposide, etc.; (d) antibiotics such as dactinomycin, daunorubicin, doxorubicin, bleomycin, plicamycin, mitomycin c, etc.; (e) enzymes such as L-asparaginase, heparinases, chondroitinases, etc.; (f) interferons and interleukins, such as interferon-α, interferon-γ, tumor necrosis factor, etc.; (g) platinum coordination complexes such as cisplatin, carboplatin or their derivatives; and (h) other miscellaneous agents such as mitoxantrone, bischloroethyl nitrosourea, hydroxyurea, chloroethyl-cyclohexyl nitrosourea, prednisone, diethylstilbestrol, medroxyprogesterone, tamoxifen, mitotane, procarbazine, aminoglutethimide, progestins, androgens, antiadrogens, Leuprolide, etc.

In an exemplary embodiment, the engineered platelets include a recombinant protein which acts as an inhibitor of VEGF (i.e., VEGF antagonists). Such proteins include antibodies and antibody analogs (such as single chain antibodies, monobodies, antigen binding sites and the like) such as ranibizumab, VEGF-traps such as Aflibercept which are soluble proteins including ligand binding domains from VEGF receptors, which bind to either VEGF or the VEGF receptor and block receptor activation. In preferred embodiments, the polypeptide VEGF antagonist is expressed in MK cells in a manner in which it is incorporated into granules, particularly α-granules, of the platelets and released upon activation of the platelets.

Although, a preferred use of the engineered platelets composition would be in tumor therapy, both solid and myeloid, the same principle is embodied in the treatment of other abnormal angiogenesis-based pathologies. Other pathologies may include arthritis, retinopathies, psoriasis, solid tumors, benign tumors, Kaposi's sarcoma, and hematological malignancies. This could include drugs described earlier; or for example in the case of arthritis, it may comprise of disease modifying drugs (DMARDs), non-steroidal anti-inflammatory drugs (NSAIDS), Colchicine, methotrexate, etc.

In exemplary embodiments, the engineered platelets can be loaded with such anticancer drugs as may be selected from acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, Bacillus calmette-guerin (BCG), Baker's Antifol (soluble), beta-2'-deoxythioguanosine, bisantrene HCl, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids,

*Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol., flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of Bacillus calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof.

The engineered platelets may include one or more immunostimulatory agents in order to promote immune activation against tumor cells, so may include such agents as a toll like receptor (TLR) agonist, TLR4, TLR7, TLR9, N-acetylmuramyl-L-alanine-D-isoglutamine (MDP), lipopolysaccharides (LPS), genetically modified and/or degraded LPS, alum, glucan, colony stimulating factors, EPO, GM-CSF, G-CSF, M-CSF, pegylated G-CSF, SCF, IL-3, IL6, PIXY 321, interferons, γ-interferon, α-interferon, interleukins, IL-2, IL-7, IL-12, IL-15, IL-18, MHC Class II binding peptides, saponins, QS2I, unmethylated CpG sequences, I-methyl tryptophan, arginase inhibitors, cyclophosphamide, or antibodies that block immunosuppressive functions, anti-CTLA4 antibodies, or mixtures of two or more thereof.

In certain instances, particular for creating engineered platelets including small molecule drugs and/or nucleic acids, the active agent(s) can be introduced into the platelets by addition to the culture media for megakaryocytes, proplatelets or other cells along the differentiation pathway, or can be provided in media/solutions in which the platelets are incubated.

In other instances, particular for creating engineered platelets including protein therapeutics, the active agent(s) can be recombinantly expressed by the megakaryocytes, proplatelets or other cells along the differentiation pathway, and can thus be present in the resulting platelets. In preferred embodiments, the recombinant protein is packaged in the platelet granules (especially α-granules). Certain recombinant proteins are automatically trafficked into the granules, such as Factor VIII, otherwise may require the use of fusion proteins which include granule targeting moieties which traffic the fusion protein to platelet granules. An exemplary granule targeting moiety is platelet factor 4 (PF4), or a portion thereof sufficient to traffic the resulting fusion protein to platelet granules. See, for example, Briguet-Laugier et al., J Thromb Haemost. 2004 2(12):2231-40; El Goli et al. J Biol Chem. 2005 280(34):30329-35;

An exemplary embodiment of a recombinant protein that requires no addition granule trafficking moiety is Factor VIII. The present invention contemplates platelets that have been engineered to have Factor VIII stored in their a-granules, and which release the recombinant protein upon activation such as at the site of a wound. Hemophilia A is an X chromosome-linked bleeding disorder caused by defects in the factor VIII (FVIII) gene and affecting approximately 1:5000 male individuals. Current treatment consists of factor replacement by using pooled FVIII concentrate or recombinant product. The limitations of these products include their expense and the limited ability of these products to prevent long-term sequelae unless used in a rigorous prophylaxis regimen. About 10% of the population with hemophilia A develops inhibitors to the infusion product, requiring alternative, even more expensive and less effective, forms of therapy. Concerns about infectious complications from blood-derived replacement products have continued to be an issue even with new preparative techniques. The high costs of treatment, the infectious and immune complications of therapy, and the limitations in preventing the long-term complications of hemophilia A make a platelet delivery strategy for the treatment of hemophilia A an attractive alternate form of therapy.

To further illustrate, Yarovoi et al. Blood, 2003 102(12): 4007 describes an expression construct that can be used to generate the Factor VIII engineered platelets of the present invention. In particular, the coding sequence for (human) Factor VIII can be placed under the regulatory control of the megakaryocyte-specific glycoprotein Ib (GPIbα) proximal promoter region. See Fujita et al. Blood. 1998; 92:488-495. The ectopically expressed factor VIII in developing megakaryocytes is stored in α-granules, which are contained within the platelets produced by the MKs, and then released from circulating platelets upon activation.

Pharmaceutical Preparations

Exemplary compositions of the present disclosure may be formulation suitable for use in treating a human patient, such as pyrogen-free or essentially pyrogen-free, and pathogen-free. When administered, the pharmaceutical preparations for use in this disclosure may be in a pyrogen-free, pathogen-free, physiologically acceptable form.

Additional exemplary compositions of the present disclosure may be irradiated, e.g., prior to administration. For example, the cells may be irradiated with gamma irradiation, e.g., with a dosage of approximately 25 gy. For example, the composition may be irradiated with a dosage sufficient to mitotically inactivate any nucleated eukaryotic cells, and/or pathogens contained in the composition, e.g., in a dosage sufficient to mitotically inactivate any pluripotent stem cells, MKs, leukocytes, and/or PVE-HE that may be contained therein.

Delivery of Platelets

Various membranes, devices and methods of their manufacture have been proposed and evaluated as a means of transplanting cells and their secreted products into the human body and are collectively referred to in the patent literature as bioartificial implants. Typically they share a common principle of operation, that is, the cells are sequestered inside a chamber bounded by a semipermeable membrane. Long term cell viability is thought to rely on the sustained diffusive exchange of nutrients and waste products with adjacent vascularized tissue. (U.S. Pat. Nos. 6,372,244, 6,113,938, 6,322,804 4,911,717, 5,855,613, 6,083,523, 5,916,554, 6,511,473, 6,485,723). There are three major types of devices described in the scientific and patent literature for implantation of cells into various tissue compartments including: planar disk designs, hollow fiber-based designs, and geometric solid-based designs. These devices are typically designed to be placed in a body cavity.

DEFINITIONS

"Embryoid bodies" refers to clumps or clusters of pluripotent cells (e.g., iPSC or ESC) which may be formed by culturing pluripotent cells under non-attached conditions, e.g., on a low-adherent substrate or in a "hanging drop." In these cultures, pluripotent cells can form clumps or clusters of cells denominated as embryoid bodies. See Itskovitz-Eldor et al., Mol Med. 2000 February; 6(2):88-95, which is hereby incorporated by reference in its entirety. Typically, embryoid bodies initially form as solid clumps or clusters of pluripotent cells, and over time some of the embryoid bodies come to include fluid filled cavities, the latter former being referred to in the literature as "simple" EBs and the latter as "cystic" embryoid bodies.

The term "embryonic stem cells" (ES cells) is used herein as it is used in the art. This term includes cells derived from the inner cell mass of human blastocysts or morulae, including those that have been serially passaged as cell lines. The ES cells may be derived from fertilization of an egg cell with sperm, as well as using DNA, nuclear transfer, parthenogenesis, or by means to generate ES cells with homozygosity in the HLA region. ES cells are also cells derived from a zygote, blastomeres, or blastocyst-staged mammalian embryo produced by the fusion of a sperm and egg cell, nuclear transfer, parthenogenesis, androgenesis, or the reprogramming of chromatin and subsequent incorporation of the reprogrammed chromatin into a plasma membrane to produce a cell. Embryonic stem cells, regardless of their source or the particular method used to produce them, can be identified based on (i) the ability to differentiate into cells of all three germ layers, (ii) expression of at least Oct 4 and alkaline phosphatase, and (iii) ability to produce teratomas when transplanted into immunodeficient animals. Embryonic stem cells that may be used in embodiments of the present invention include, but are not limited to, human ES cells ("ESC" or "hES cells") such as MA01, MA09, ACT-4, No. 3, H1, H7, H9, H14 and ACT30 embryonic stem cells. Additional exemplary cell lines include NED1, NED2, NED3, NED4, NED5, and NED7. See also NIH Human Embryonic Stem Cell Registry. An exemplary human embryonic stem cell line that may be used is MA09 cells. The isolation and preparation of MA09 cells was previously described in Klimanskaya, et al. (2006) "Human Embryonic Stem Cell lines Derived from Single Blastomeres." Nature 444: 481-485. The isolation and preparation of other ES cells that can be used in accordance with this disclosure was also previously described in Chung et al. (2008) "Human Embryonic Stem Cell Line Generated Without Embryo Destruction", Cell Stem Cell, 2:113-117. The human ES cells used in accordance with exemplary embodiments of the present invention may be derived and maintained in accordance with GMP standards.

As used herein, the term "pluripotent stem cells" includes embryonic stem cells, embryo-derived stem cells, and induced pluripotent stem cells, regardless of the method by which the pluripotent stem cells are derived. Pluripotent stem cells are defined functionally as stem cells that are: (a) capable of inducing teratomas when transplanted in immunodeficient (SCID) mice; (b) capable of differentiating to cell types of all three germ layers (e.g., can differentiate to ectodermal, mesodermal, and endodermal cell types); and (c) express one or more markers of embryonic stem cells (e.g., express Oct 4, alkaline phosphatase. SSEA-3 surface antigen, SSEA-4 surface antigen, nanog, TRA-1-60, TRA-1-81, SOX2, REX1, etc.). In certain embodiments, pluripotent stem cells express one or more markers selected from the group consisting of: OCT-4, alkaline phosphatase, SSEA-3, SSEA-4, TRA-1-60, and TRA-1-81. Exemplary pluripotent stem cells can be generated using, for example, methods known in the art. Exemplary pluripotent stem cells include embryonic stem cells derived from the ICM of blastocyst stage embryos, as well as embryonic stem cells derived from one or more blastomeres of a cleavage stage or morula stage embryo (optionally without destroying the remainder of the embryo). Such embryonic stem cells can be generated from embryonic material produced by fertilization or by asexual means, including somatic cell nuclear transfer (SCNT), parthenogenesis, and androgenesis. Further exemplary pluripotent stem cells include induced pluripotent stem cells (iPSCs) generated by reprogramming a somatic cell by expressing a combination of factors (herein referred to as reprogramming factors). The iPSCs can be generated using fetal, postnatal, newborn, juvenile, or adult somatic cells.

In certain embodiments, factors that can be used to reprogram somatic cells to pluripotent stem cells include, for example, a combination of Oct 4 (sometimes referred to as Oct 3/4), Sox2, c-Myc, and Klf4. In other embodiments, factors that can be used to reprogram somatic cells to pluripotent stem cells include, for example, a combination of Oct 4, Sox2, Nanog, and Lin28. In certain embodiments, at least two reprogramming factors are expressed in a somatic cell to successfully reprogram the somatic cell. In other embodiments, at least three reprogramming factors are expressed in a somatic cell to successfully reprogram the somatic cell. In other embodiments, at least four reprogramming factors are expressed in a somatic cell to successfully reprogram the somatic cell. In other embodiments, additional reprogramming factors are identified and used alone or in combination with one or more known reprogramming factors to reprogram a somatic cell to a pluripotent stem cell. Induced pluripotent stem cells are defined functionally and include cells that are reprogrammed using any of a variety of methods (integrative vectors, non-integrative vectors, chemical means, etc.). Pluripotent stem cells may be genetically modified or otherwise modified to increase longevity, potency, homing, to prevent or reduce alloimmune responses or to deliver a desired factor in cells that are differentiated from such pluripotent cells (for example, platelets).

"Induced pluripotent stem cells" (iPS cells or iPSC) can be produced by protein transduction of reprogramming factors in a somatic cell. In certain embodiments, at least two reprogramming proteins are transduced into a somatic cell to successfully reprogram the somatic cell. In other embodiments, at least three reprogramming proteins are transduced into a somatic cell to successfully reprogram the somatic cell. In other embodiments, at least four reprogramming proteins are transduced into a somatic cell to successfully reprogram the somatic cell.

The pluripotent stem cells can be from any species. Embryonic stem cells have been successfully derived in, for example, mice, multiple species of non-human primates, and humans, and embryonic stem-like cells have been generated from numerous additional species. Thus, one of skill in the art can generate embryonic stem cells and embryo-derived stem cells from any species, including but not limited to, human, non-human primates, rodents (mice, rats), ungulates (cows, sheep, etc.), dogs (domestic and wild dogs), cats (domestic and wild cats such as lions, tigers, cheetahs), rabbits, hamsters, gerbils, squirrel, guinea pig, goats, elephants, panda (including giant panda), pigs, raccoon, horse, zebra, marine mammals (dolphin, whales, etc.) and the like. In certain embodiments, the species is an endangered species. In certain embodiments, the species is a currently extinct species.

Similarly, iPS cells can be from any species. These iPS cells have been successfully generated using mouse and human cells. Furthermore, iPS cells have been successfully generated using embryonic, fetal, newborn, and adult tissue. Accordingly, one can readily generate iPS cells using a donor cell from any species. Thus, one can generate iPS cells from any species, including but not limited to, human, non-human primates, rodents (mice, rats), ungulates (cows, sheep, etc.), dogs (domestic and wild dogs), cats (domestic and wild cats such as lions, tigers, cheetahs), rabbits, hamsters, goats, elephants, panda (including giant panda), pigs, raccoon, horse, zebra, marine mammals (dolphin, whales, etc.) and the like. In certain embodiments, the species is an endangered species. In certain embodiments, the species is a currently extinct species.

Induced pluripotent stem cells can be generated using, as a starting point, virtually any somatic cell of any developmental stage. For example, the cell can be from an embryo, fetus, neonate, juvenile, or adult donor. Exemplary somatic cells that can be used include fibroblasts, such as dermal fibroblasts obtained by a skin sample or biopsy, synoviocytes from synovial tissue, foreskin cells, cheek cells, or lung fibroblasts. Although skin and cheek provide a readily available and easily attainable source of appropriate cells, virtually any cell can be used. In certain embodiments, the somatic cell is not a fibroblast.

The induced pluripotent stem cell may be produced by expressing or inducing the expression of one or more reprogramming factors in a somatic cell. The somatic cell may be a fibroblast, such as a dermal fibroblast, synovial fibroblast, or lung fibroblast, or a non-fibroblastic somatic cell. The somatic cell may be reprogrammed through causing expression of (such as through viral transduction, integrating or non-integrating vectors, etc.) and/or contact with (e.g., using protein transduction domains, electroporation, microinjection, cationic amphiphiles, fusion with lipid bilayers containing, detergent permeabilization, etc.) at least 1, 2, 3, 4, 5 reprogramming factors. The reprogramming factors may be selected from Oct 3/4, Sox2, NANOG, Lin28, c Myc, and Klf4. Expression of the reprogramming factors may be induced by contacting the somatic cells with at least one agent, such as a small organic molecule agents, that induce expression of reprogramming factors.

Further exemplary pluripotent stem cells include induced pluripotent stem cells generated by reprogramming a somatic cell by expressing or inducing expression of a combination of factors ("reprogramming factors"). iPS cells may be obtained from a cell bank. The making of iPS cells may be an initial step in the production of differentiated cells. iPS cells may be specifically generated using material from a particular patient or matched donor with the goal of generating tissue-matched megakaryocytes and platelets. iPSCs can be produced from cells that are not substantially immunogenic in an intended recipient, e.g., produced from autologous cells or from cells histocompatible to an intended recipient.

The somatic cell may also be reprogrammed using a combinatorial approach wherein the reprogramming factor is expressed (e.g., using a viral vector, plasmid, and the like) and the expression of the reprogramming factor is induced (e.g., using a small organic molecule.) For example, reprogramming factors may be expressed in the somatic cell by infection using a viral vector, such as a retroviral vector or a lentiviral vector. Also, reprogramming factors may be expressed in the somatic cell using a non-integrative vector, such as an episomal plasmid. See, e.g., Yu et al., Science. 2009 May 8; 324(5928):797-801, which is hereby incorporated by reference in its entirety. When reprogramming factors are expressed using non-integrative vectors, the factors may be expressed in the cells using electroporation, transfection, or transformation of the somatic cells with the vectors. For example, in mouse cells, expression of four factors (Oct3/4, Sox2, c myc, and Klf4) using integrative viral vectors is sufficient to reprogram a somatic cell. In human cells, expression of four factors (Oct3/4, Sox2, NANOG, and Lin28) using integrative viral vectors is sufficient to reprogram a somatic cell.

Once the reprogramming factors are expressed in the cells, the cells may be cultured. Over time, cells with ES characteristics appear in the culture dish. The cells may be chosen and subcultured based on, for example, ES morphology, or based on expression of a selectable or detectable marker. The cells may be cultured to produce a culture of cells that resemble ES cells—these are putative iPS cells.

To confirm the pluripotency of the iPS cells, the cells may be tested in one or more assays of pluripotency. For example, the cells may be tested for expression of ES cell markers; the cells may be evaluated for ability to produce teratomas when transplanted into SCID mice; the cells may be evaluated for ability to differentiate to produce cell types of all three germ layers. Once a pluripotent iPSC is obtained it may be used to produce megakaryocyte cells and platelets.

The term "hemogenic endothelial cells" (PVE-HE) as used herein refers to cells capable of differentiating to give rise to hematopoietic cell types or endothelial cell types, which may express PECAM1, VE-Cadherin, and/or endoglin (e.g., PECAM1+VE-Cad+Endoglin+ hemogenic PVE-HE), and which may optionally be derived from pluripotent stem cells. These cells can be described based on numerous structural and functional properties including, but not limited to, expression (RNA or protein) or lack of expression (RNA or protein) of one or more markers. The PVE-HE cells are characterized by the expression of the markers CD31 (PECAM1). For example, at least about 90%, at least about 95%, or at least about 9 addition, immunofluorescence and transmission electron microscopic results further demonstrate 9% of the PVE-HE cells in a population may be CD31+. The PVE-HE cells may also express the markers CD105 (endoglin), and CD144 (VE-Cadherin). For example, at least about 70%, about at least about 80%, at least about 85%, at least about 90%, at least about 95%, or at least about 99% of the PVE-HE cells in a population may be CD105+, CD144+, and CD31+. In certain embodiments the PVE-HE cells are loosely adherent to each other. CD31, the platelet endothelial cell adhesion molecule-1 (PECAM-1), has been used as a marker for the development of endothelial cell progenitors, vasculogenesis, and angiogenesis. CD31 is constitutively expressed on the surface of adult and embryonic endothelial cells, is a major constituent of the endothelial cell intercellular junction (where up to $10^6$ PECAM-1 molecules are concentrated) and is weakly expressed on many peripheral leukocytes and platelets.

In exemplary embodiments, PVE-HE may exhibit one or more, preferably all, of the following characteristics: (1) Significant amount of CD31+ PVE-HE cells can be detected as early as 72 hours after initiation of PVE-HE differentiation. (2) It will reach peak level at round 120 to 146 hours after initiation of PVE-HE differentiation. (3) The CD31+ PVE-HE cell population can be isolated and cryopreserved. (3) They express almost all endothelial progenitor cell surface marker such as CD31, CD105 (Endoglin), CD144 (VE-Cadherin). They may also express CD34, CD309 (KDR) and CD146. (4) A subpopulation of CD31+ PVE-HE cells also express CXCR4 (CD184). (5) The endothelial lineage potential can be confirmed by culturing CD31+ PVE-HE cells onto fibronectin in endothelial cell (EC)-specific medium (such as EGM-2 or EndoGro) to obtain monolayer of cells with typical endothelial morphology. (6) PVE-HE-derived endothelial cells (PVE-HE-EC) not only express CD31 (localized at cell-cell junction), but also express von Willibrandt Factor (vWF), and capable of LDL-uptake. (7) PVE-HE-ECs are capable of forming 3D-network structure when cultured on top of Matrigel. (8) When plating in extreme low density on Fibronectin in EC-specific medium, the CD31+ PVE-HE cells are capable of forming colonies with typical endothelial morphology confirming their clonogenic capability. (9) When plating in methylcellulose medium for blast-colony growth, blast colony can only be generated from CD31+ fraction. Unlike CD31− cells, both CD34− and CD105− are capable of generating blast colonies suggesting hemogenic capability is exclusively maintained in CD31 fraction only. (10) Newly derived PVE-HE-EC maintain hemogenic potential and will give rise to hemogenic cells if cultured under conditions favorable to the hematopoietic lineages.

The term "megakaryocyte lineage-specific progenitor cells" ("MLPs"), as used herein, refers to mononuclear hematopoietic stem cells committed to at least the megakaryocyte lineage and includes, but is not limited to, cells in the umbilical cord blood, bone marrow, and peripheral blood as well as hematopoietic stem cells, cells derived from human embryonic stem cells, and cells derived from induced pluripotent stem cells. These cells can be described based on numerous structural and functional properties including, but not limited to, expression (RNA or protein) or lack of expression (RNA or protein) of one or more markers. The MLPs of this disclosure can be a mixture of immature and mature cells. The percentage of mature vs. immature MLPs may vary based upon the length of time in culture in MLP-Derivation and Expansion Medium (MLP-DEM, also referred to herein as APEL) (described in Example 2). Immature MLPs are characterized by the expression of the markers CD41a, CD31, CD34, CD13 and the lack of CD14 and CD42b marker expression. Exemplary methods of the disclosure provide for detection and/or purification of MLPs by a method comprising detecting the expression of CD13 and/or enriching or purifying CD13-positive cells. Optionally in these methods the expression of CD13 may be detected and/or used as a basis for cell purification in combination with the expression of one or more additional markers of immature or mature MLPs described herein. Mature MLPs are characterized by the expression of the markers CD41a, CD31, CD34, CD13, CD42b and the lack of CD14 expression. In certain embodiments MLPs generated in feeder free culture may be semi-detached or detach completely and may float in the culture medium. For example, MLPs may be collected from the PVE-HE when they start to float up in suspension. Preferably MLPs are not plated and allowed to adhere, which may permit differentiation into lineages other than MKs or non-MK lineages (such as endothelial cells). MLPs are preferably grown in suspension to produce MKs. Optionally, MLPs may be cryopreserved.

The term "megakaryocytes" (MKs) as used herein refers to large polyploid hematopoietic cells that give rise to platelets, as well as smaller MKs (which may be produced by the subject methods) that may be diploid but fully capable of producing platelets. One primary morphological characteristic of mature MKs is the development of a large, polyploid nucleus. Mature MKs stop proliferating but continue to increase their DNA content through endomitosis; with a parallel increase in cell size. The large polyploid nucleus, large cell volume, and ample cytoplasm of MKs allows for the production of thousands of platelets per cell. MKs can be described based on these and numerous other structural and functional properties including, but not limited to, expression (RNA or protein) or lack of expression (RNA or protein) of one or more markers. Mature MKs express the markers CD41a and CD42b. Mature MKs may also express CD61 and CD29. For example, a MK of the present disclosure is preferably functional in the sense of being able to produce platelets, e.g., when cultured under conditions those described herein. Exemplary embodiments provide a method of detecting matured MKs comprising detecting expression of CD29 and identifying CD29 positive cells as matured MKs. Additional exemplary embodiments provide a method of purifying MKs, comprising purification of CD29 positive cells from a population, for example using magnetic bead subtraction, FACS, other immunoaffinity based methods, or the like. Optionally in these methods the expression of CD29 may be detected and/or used as a basis for cell purification in combination with the expression of one or more additional markers of matured MKs, such as those markers shown in Table 1 (which provides further exemplary cell surface marker expression of matured MKs).

In vivo, MK are derived from hematopoietic stem cell precursor cells in the bone marrow. These multipotent stems cells reside in the marrow sinusoids and are capable of producing all types of blood cells depending on the signals they receive. The primary signal for MK production is TPO. TPO induces differentiation of progenitor cells in the bone marrow towards a final MK phenotype. The MK develops through the following lineage: CFU-ME (pluripotent hemopoietic stem cell or hemocytoblast), megakaryoblast, promegakaryocyte, megakaryocyte. The cell eventually reaches megakaryoblast stage and loses its ability to divide. However, it is still able to replicate its DNA and continue development, becoming polyploidy. The cytoplasm continues to expand and the DNA complement can increase to greater than 64 N.

Once the cell has completed differentiation and becomes a mature megakaryocyte, it begins the process of producing platelets. TPO plays a role in inducing the MK to form small proplatelet processes. Platelets are held within these internal membranes within the cytoplasm of the MK. There are two proposed mechanisms for platelet release. In one scenario, these proplatelet processes break up explosively to become platelets. Alternatively, the cell may form platelet ribbons into blood vessels. The ribbons are formed via pseudopodia and they are able to continuously emit platelets into circulation. In either scenario, each of these proplatelet processes can give rise to 2000-5000 new platelets upon breakup.

Overall, more than 75% of these newly-produced platelets will remain in circulation while the remainder will be sequestered by the spleen.

The term "platelet" as used herein refers to anucleate cytoplasmic bodies derived from cells that are involved in the cellular mechanisms of primary hemostasis leading to the formation of blood clots. Platelets (thrombocytes) are small, irregularly shaped clear cell fragments 2-3 pm in diameter, which in vivo are derived from fragmentation of precursor megakaryocytes (MK). Platelets can be identified based on numerous structural and functional properties including, but not limited to, expression (RNA or protein) or lack of expression (RNA or protein) of one or more markers. Platelets express the markers CD41a and CD42b. Platelets adhere to tissue and to each other in response to vascular injury.

The terms "functional platelet" or "platelets that are functional" as used herein refer to platelets that can be activated by thrombin and participate in clot retraction. In exemplary embodiments, whether platelets are functional platelets may be determined using an animal model, e.g., as described in Example 4 (FIG. 12), for example by comparison to naturally-derived platelets, which may be of the same species. Additionally, activated platelets can be identified by expression of CD62p and αIIbβIII, and functional platelets can be identified (optionally quantitatively) by their expression of these markers upon activation such as upon activation with thrombin. The phrase "substantially all of the platelets are functional" refers to a composition or preparation comprising platelets wherein, for example, at least 60% of the platelets are functional platelets, or at least 65%, at least 70%, at least 80%, at least 90%, at least 95%, at least 96%, at least 97%, at least 98%, at least 99% of the platelets are functional platelets. Functional platelets may be active for at least 5 days when stored at 22-37° C.

PECAM1 (CD31) is a member of the immunoglobulin (Ig) superfamily that is expressed on the surface of circulating platelets, monocytes, neutrophils, and particular T-cell subsets. It is also a major constituent of the endothelial cell intercellular junction, where up to an estimated 1 million molecules are concentrated. Because of this cellular expression pattern, PECAM1 is implicated in several functions, including transendothelial migration of leukocytes, angiogenesis, and integrin activation. Ig superfamily mediate cell adhesion (e.g., NCAM1, ICAM1, and VCAM1) or antigen recognition (e.g., immunoglobulins, T-cell receptors, and MHC molecules). In addition, a subgroup comprising 30 members characterized by the presence of 1 or more immunoreceptor tyrosine-based inhibitory motifs (ITIMs) within their cytoplasmic domains has also been recognized. PECAM1, which has 6 ITIMs within its cytoplasmic domain, is a member of this subfamily.

Endoglin (ENG), also called CD105, is a homodimeric membrane glycoprotein primarily associated with human vascular endothelium. It is also found on bone marrow proerythroblasts, activated monocytes, fibroblasts, smooth muscle cells and lymphoblasts in childhood leukemia. Endoglin is a component of the transforming growth factor-beta (TGFB) receptor complex and binds TGFB 1 with high affinity. Endoglin is involved in the cytoskeletal organization affecting cell morphology and migration, in processes such as development of cardiovascular system and in vascular remodeling. Its expression is regulated during heart development. Experimental mice without the endoglin gene die due to cardiovascular abnormalities.

VE-cadherin (CD144) is a classical cadherin from the cadherin superfamily. VE-cadherin plays an important role in endothelial cell biology through control of the cohesion and organization of the intercellular junctions, therefore maintain the integrity of the endothelium. VE-cadherin is indispensable for proper vascular development. Transgenic mouse models studies confirmed that VE-cadherin deficiency is embryonically lethal due to vascular defects. VE-cadherin serves the purpose of maintaining newly formed vessels.

The term "ROCK inhibitor" as used herein refers to any substance that inhibits or reduces the function of Rho-associated kinase or its signaling pathway in a cell, such as a small molecule, an siRNA, a miRNA, an antisense RNA, or the like. "ROCK signaling pathway," as used herein, may include any signal processors involved in the ROCK-related signaling pathway, such as the Rho-ROCK-Myosin II signaling pathway, its upstream signaling pathway, or its downstream signaling pathway in a cell. An exemplary ROCK inhibitor that may be used is Stemgent's Stemolecule Y27632, a rho-associated protein kinase (ROCK) inhibitor (see Watanabe et al., Nat Biotechnol. 2007 June; 25(6):681-6) Other ROCK inhibitors include, e.g., H-1152, Y-30141, Wf-536, HA-1077, hydroxyl-HA-1077, GSK269962A and SB-772077-B. Doe et al., J. Pharmacol. Exp. Ther., 32:89-98, 2007; Ishizaki, et al., Mol. Pharmacol., 57:976-983, 2000; Nakajima et al., Cancer Chemother. Pharmacol., 52:319-324, 2003; and Sasaki et al., Pharmacol. Ther., 93:225-232, 2002, each of which is incorporated herein by reference as if set forth in its entirety. ROCK inhibitors may be utilized with concentrations and/or culture conditions as known in the art, for example as described in US PGPub No. 2012/0276063 which is hereby incorporated by reference in its entirety. For example, the ROCK inhibitor may have a concentration of about 0.05 to about 50 microM, for example, at least or about 0.05, 0.1, 0.2, 0.5, 0.8, 1, 1.5, 2, 2.5, 5, 7.5, 10, 15, 20, 25, 30, 35, 40, 45, or 50 microM, including any range derivable therein, or any concentration effective for promoting cell growth or survival.

For example, pluripotent stem cell viability may be improved by inclusion of a ROCK inhibitor. In an exemplary embodiment, the pluripotent stem cells may be maintained under feeder-free conditions. In another example, megakaryocyte lineage-specific progenitor cell viability may be improved by inclusion of a ROCK inhibitor. In another example, megakaryocyte viability may be improved by inclusion of a ROCK inhibitor. In another exemplary embodiment, the megakaryocyte lineage-specific progenitor cell may be maintained under feeder free conditions.

ABBREVIATIONS iPS: induced pluripotent stem
iPSC: induced pluripotent stem cell
hiPSC: human induced pluripotent stem cell
hES: human embryonic stem
hESC: human embryonic stem cell
MK: megakaryocyte
MLP: megakaryocytic lineage-specific progenitor also called megakaryocyte progenitor (MKP)
PVE-HE: hemogenic endothelial cell, which are optionally PECAM1+VE-Cadherin+Endoglin+ and which are optionally derived from pluripotent stem cells,
iPS-PVE-HE: iPS cell-derived hemogenic endothelial cell (such as a PECAM1+VE-Cadherin+Endoglin+ cell)
hES-PVE-HE: hES cell-derived hemogenic endothelial cell (such as a PECAM1+VE-Cadherin+Endoglin+ cell)
PVE-HE-MLP: megakaryocytic lineage-specific progenitor produced from a hemogenic endothelial cell iPS-PVE-HE-MLP: PVE-HE-MLP produced from an iPS cell hES-PVE-HE-MLP: PVE-HE-MLP produced from an hES cell PVE-HE-MLP-MK: megakaryocyte produced from a megakaryocytic lineage-specific progenitor which was produced from a hemogenic endothelial cell iPS-PVE-HE-MLP-MK: PVE-HE-MLP-MK produced from an iPS cell hES-PVE-HE-MLP-MK: PVE-HE-MLP-MK produced from an hES cell PLT: platelet hiPSC-PLT: platelet or platelet-like particle produced from human induced pluripotent stem cells hESC-PLT: platelet or platelet-like particle produced from human embryonic stem cells ADM: advanced differentiation morphology.

REFERENCES

1. Guerriero R, Mattia G, Testa U et al. Stromal cell-derived factor 1 alpha increases polyploidization of megakaryocytes generated by human hematopoietic progenitor cells. Blood 2001; 97:2587-2595.
2. Matsunaga T, Tanaka I, Kobune M et al. Ex vivo large-scale generation of human platelets from cord blood CD34+ cells. Stem Cells 2006; 24:2877-2887.
3. Kaufman D S, Hanson E T, Lewis R L, Auerbach R, Thomson J A. Hematopoietic colony-forming cells derived from human embryonic stem cells. Proc. Natl. Acad. Sci. U.S.A. 2001; 98: 10716-10721.
4. Lu S-J, Li F, Vida L, Honig G R. CD34+CD38-hematopoietic precursors derived from human embryonic stem cells exhibit an embryonic gene expression pattern. Blood 2004; 103:4134-4141.
5. Chadwick K, Wang L, Li L et al. Cytokines and BMP-4 promote hematopoietic differentiation of human embryonic stem cells. Blood 2003 2003; 102:906-915.
6. Chang K H, Nelson A M, Cao H et al. Definitive-like erythroid cells derived from human embryonic stem cells coexpress high levels of embryonic and fetal globins with little or no adult globin. Blood 2006; 108: 1515-1523.
7. Tian X, Morris J K, Linehan J L, Kaufman D S. Cytokine requirements differ for stroma and embryoid body-mediated hematopoiesis from human embryonic stem cells. Exp. Hematol. 2004; 32: 1000-1009.
8. Vodyanik M A, Bork J A, Thomson J A, Slukvin I I. Human embryonic stem cell-derived CD34+ cells: efficient production in the coculture with OP9 stromal cells and analysis of lymphohematopoietic potential. Blood 2005; 105:617-626.
9. Wang L, Menendez P, Shojaei F et al. Generation of hematopoietic repopulating cells from human embryonic stem cells independent of ectopic HOXB4 expression. J. Exp. Med. 2005; 201: 1603-1614.
10. Woll P S, Martin C H, Miller J S, Kaufman D S. Human embryonic stem cell-derived NK cells acquire functional receptors and cytolytic activity. J. Immunol. 2005; 175: 5095-5103.
11. Zambidis E T, Peault B, Park T S, Bunz F, Civin C I. Hematopoietic differentiation of human embryonic stem cells progresses through sequential hematoendothelial, primitive, and definitive stages resembling human yolk sac development. Blood 2005; 106:860-870.
12. Qiu C, Hanson E, Olivier E et al. Differentiation of human embryonic stem cells into hematopoietic cells by coculture with human fetal liver cells recapitulates the globin switch that occurs early in development. Exp. Hematol. 2005; 33: 1450-1458.
13. Zhan X, Dravid G, Ye Z et al. Functional antigen-presenting leucocytes derived from human embryonic stem cells in vitro. Lancet 2004; 364: 163-171.
14. Ledran M H, Krassowska A, Armstrong L et al. Efficient hematopoietic differentiation of human embryonic stem cells on stromal cells derived from hematopoietic niches. Cell Stem Cell 2008; 3:85-98.
15. Gaur M, Kamata T, Wang S et al. Megakaryocytes derived from human embryonic stem cells: a genetically tractable system to study megakaryocytopoiesis and integrin function. J. Thromb. Haemost. 2006; 4:436-442.
16. Takayama N, Nishikii H, Usui J et al. Generation of functional platelets from human embryonic stem cells in vitro via ES-sacs, VEGF-promoted structures that concentrate hematopoietic progenitors. Blood 2008; 111: 5298-5306.
17. Lu S J, Feng Q, Caballero S et al. Generation of functional hemangioblasts from human embryonic stem cells. Nat. Methods 2007; 4:501-509.
18. Klimanskaya I, McMahon J. Approaches of derivation and maintenance of human ES cells: Detailed procedures and alternatives. In: Lanza Rea, ed. Handbook of Stem Cells. Volume 1: Embryonic Stem Cells. New York, USA: Elsevier/Academic Press; 2004:437-449.
19. Lu S J, Luo C, Holton K et al. Robust generation of hemangioblastic progenitors from human embryonic stem cells. Regen. Med. 2008; 3:693-704.
20. Lu S J, Feng Q, Park J S et al. Biologic properties and enucleation of red blood cells from human embryonic stem cells. Blood 2008; 112:4475-4484.
21. Fujiki H, Kimura T, Minamiguchi H et al. Role of human interleukin-9 as a megakaryocyte potentiator in culture. Exp. Hematol. 2002; 30: 1373-1380.
22. Jeanpierre S, Nicolini F E, Kaniewski B et al. BMP4 regulation of human megakaryocyte differentiation is involved in thrombopoietin signaling. Blood 2008; 112: 3154-3163.
23. Lordier L, Jalil A, Aurade F et al. Megakaryocyte endomitosis is a failure of late cytokinesis related to defects in the contractile ring and Rho/ROCK signaling. Blood 2008; 112:3164-3174.
24. Chang Y, Aurade F, Larbret F et al. Proplatelet formation is regulated by the Rho/ROCK pathway. Blood 2007; 109:4229-4236.
25. Taguchi K, Saitoh M, Arai Y et al. Disparate effects of interleukin 11 and thrombopoietin on megakaryocytopoiesis in vitro. Cytokine 2001; 15:241-249.
26. Philipp C S, Remmler J, Zucker-Franklin D. The effects of Mpl-ligand, interleukin-6 and interleukin-11 on megakaryocyte and platelet alpha-granule proteins. Thromb. Haemost. 1998; 80:968-975.
27. Kanaji T, Russell S, Cunningham J et al. Megakaryocyte proliferation and ploidy regulated by the cytoplasmic tail of glycoprotein Ibalpha. Blood 2004; 104:3161-3168.
28. Santoso S, Kalb R, Kiefel V, Mueller-Eckhardt C. The presence of messenger RNA for HLA class I in human platelets and its capability for protein biosynthesis. Br. J. Haematol. 1993; 84:451-456.
29. Lalezari P, Driscoll A M. Ability of thrombocytes to acquire HLA specificity from plasma. Blood 1982; 59: 167-170.
30. Sullenbarger B, Bahng J H, Gruner R, Kotov N, Lasky L C. Prolonged continuous in vitro human platelet production using three-dimensional scaffolds. Exp. Hematol. 2009; 37: 101-110.

31. Giammona L M, Fuhrken P G, Papoutsakis E T, Miller W M. Nicotinamide (vitamin B3) increases the polyploidisation and proplatelet formation of cultured primary human megakaryocytes. Br. J. Haematol. 2006; 135:554-566.
32. Nagata Y, Yoshikawa J, Hashimoto A et al. Proplatelet formation of megakaryocytes is triggered by autocrine-synthesized estradiol. Genes Dev. 2003; 17:2864-2869.
33. Larson M K, Watson S P. Regulation of proplatelet formation and platelet release by integrin alpha IIb beta3. Blood 2006; 108: 1509-1514.
34. Klimchenko O, Mori M, Distefano A et al. A common bipotent progenitor generates the erythroid and megakaryocyte lineages in embryonic stem cell-derived primitive hematopoiesis. Blood 2009; 114: 1506-1517.
35. Nishikii H, Eto K, Tamura N et al. Metalloproteinase regulation improves in vitro generation of efficacious platelets from mouse embryonic stem cells. J. Exp. Med. 2008; 205: 1917-1927.
36. Furie B, Furie B C. Mechanisms of thrombus formation. N. Engl. J. Med. 2008; 359: 938-949.
37. Day S M, Reeve J L, et al. Murine thrombosis models. Thromb. Haemost. 2004; 92: 486-494.
38. Sachs U J and Nieswandt B. In vivo thrombus formation in murine models. Circ. Res. 2007; 100: 979-991.
39. Furie B and Furie B C. In vivo thrombus formation. J. Thromb. Haemost. 2007; 5 Suppl 1: 12-17.
40. Junt T, Schulze H, et al. Dynamic visualization of thrombopoiesis within bone marrow. Science 2007; 317: 1767-1770.
41. Yu J, Hu J, et al. Human induced pluripotent stem cells free of vector and transgene sequences. Science 2009; 324: 797-801.
42. Takahashi K, Tanabe K, et al. Induction of pluripotent stem cells from adult human fibroblasts by defined factors. Cell 2007; 131: 861-872.
43. Yu J, Vodyanik M A, et al. Induced pluripotent stem cell lines derived from human somatic cells. Science 2007; 318: 1917-1920.
44. Kim D, Kim C H, et al. Generation of human induced pluripotent stem cells by direct delivery of reprogramming proteins. Cell Stem Cell 2009; 4: 472-476.
45. Ginsberg M H, Du X, Plow E F. Inside-out integrin signalling. Curr. Opin. Cell Biol. 1992; 4: 766-771.
46. Chen Y P, O'Toole T E, et al. A point mutation in the integrin beta 3 cytoplasmic domain (S752→P) impairs bidirectional signaling through alpha IIb beta 3 (platelet glycoprotein IIIb-IIIa). Blood 1994; 84: 1857-1865.
47. Cho J, Furie B C, et al. A critical role for extracellular protein disulfide isomerase during thrombus formation in mice. J. Clin. Invest 2008; 118: 1123-1131.
48. Coller B S. Anti-GPIIb/IIIa drugs: current strategies and future directions. Thromb. Haemost. 2001; 86: 427-443.
49. Cho J, Mosher D F. Enhancement of thrombogenesis by plasma fibronectin cross-linked to fibrin and assembled in platelet thrombi. Blood 2006; 107; 3555-3563.
50. Falati S, Gross P, et al. Real-time in vivo imaging of platelets, tissue factor and fibrin during arterial thrombus formation in the mouse. Nat. Med. 2002; 8: 1175-1181.
51. Reems J A, Pineault N, and Sun S. In vitro megakaryocyte production and platelet biogenesis: state of the art. Transfus. Med. Rev. 2010; 24: 33-43.
52. Chockalingam P, Sacher R A. Management of patients' refractory to platelet transfusion. J. Infus. Nurs. 2007; 30: 220-225.
53. Hod E, Schwartz J. Platelet transfusion refractoriness. Br. J. Haematol. 2008; 142: 348-360.
54. Tian X, Kaufman D S. Differentiation of embryonic stem cells towards hematopoietic cells: progress and pitfalls. Curr. Opin. Hematol. 2008; 15: 312-318.
55. Wang L, Menendez P, et al. Generation of hematopoietic repopulating cells from human embryonic stem cells independent of ectopic HOXB4 expression. J. Exp. Med. 2005; 201: 1603-1614.
56. Robert et al., Megakaryocyte and platelet production from human cord blood stem cells. Methods Mol Biol. 2012; 788:219-47.
57. Piper et al., In vivo recovery of human platelets in severe combined immunodeficient mice as a measure of platelet damage. Transfusion, 47:1540-1549, 2007.
58. Hu et al., Full reconstitution of human platelets in humanized mice after macrophage depletion. Blood 120: 1713-1716, 2012.
59. Klimanskaya et al. Human embryonic stem cell lines derived from single blastomeres. Nature 444: 481-485, 2006.
60. Chung et al. Human embryonic stem cell line generated without embryo destruction. Cell Stem Cell, 2:113-117, 2008.

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1—Generation of Pluripotent-Derived Hemogenic Endothelial Cells (PVE-HE)

Pluripotent-Derived Hemogenic Endothelial Cells (PVE-HE) were generated from induced pluripotent stem (iPS) cells.

First, iPS cells were expanded by culturing on Matrigel (a soluble preparation from Engelbreth-Holm-Swarm (EHS) mouse sarcoma cells) in the feeder-free pluripotent stem cell culture medium mTeSR1. Briefly, human iPS cells were harvested by dissociation using chemically defined Cell Dissociate Buffer (CDB) with EDTA as the sole active component. No enzyme or any other animal products were used in the culture medium or CDB. For investigators with ordinary skill in the art, it should be understood that it is possible to use another chemically defined matrix such as recombinant vitronectin or SyntheMax II, or medium such as mTeSR2, or other compatible cell dissociation reagents.

Figure 2A:
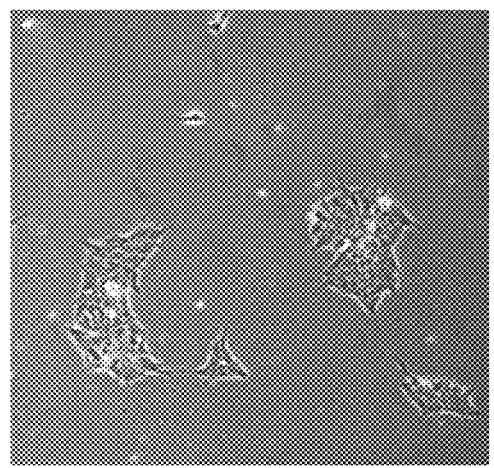
FIGS. 2A-2C. Progression of differentiation of iPS cells through advanced differentiation morphology cells (ADM). This Figure shows iPS cell progression toward PVE-HE.

Second, harvested human iPS cells were prepared for differentiation into multipotent PVE-HE which were PECAM1+VE-Cadherin+Endoglin+. Embryoid body (EB) formation was not required. Briefly, the harvested cells were resuspended in mTeSR1, and plated on top of the extracellular matrix human collagen IV (Advanced BioMatrix, cat#5022). The small molecule ROCK inhibitor Y27632 was added to the culture at 10 µM and was thought to help the harvested iPS cells attach to the Collagen IV coated surface. The iPS cells were allowed to attach for 12-48 hours in at 37° C. with 5% CO2. As shown in FIG. 2A, after 48 hours attached cells show typical pluripotent stem cell morphology under feeder-free condition.

Figure 2B:
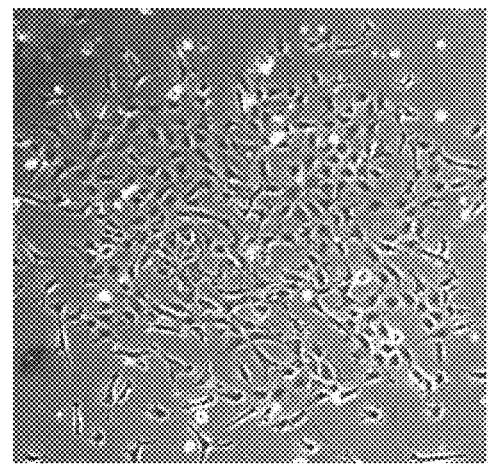
Figure 2C:
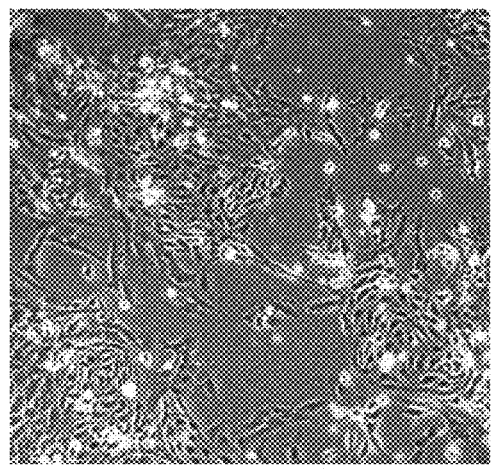

Third, prepared human iPS cells were differentiated into PVE-HE cells. Briefly, mTeSR1 medium with Y27632 was removed and a differentiation initiation medium (DIM) was added. DIM is an animal-component free medium (ACF) comprised of Iscove's Modified Dulbecco's Medium (IMDM) as basal medium, human serum albumin, iron-saturated transferrin, insulin, b-mercaptoethanol, soluble low-density lipoprotein (LDL), cholesterol, bone morphogenetic protein 4 (BMP4) at 50 ng/ml, basic fibroblast growth factor (bFGF) at 50 ng/ml, and vascular endothelial growth factor (VEGF) at 50 ng/ml. After being incubated for 48 hours at 37° C. with 5% $CO_2$, early morphology of desired PVE-HE differentiation was observed. The almost complete transition from pluripotent stem cell morphology into scattered small cell clusters can be seen in FIG. 2B. After 96 to 146 hours post PVE-HE differentiation initiation, advanced differentiation morphology was observed showing small compact cell clusters growing on top of the monolayer (FIG. 2C).

Figure 3A:
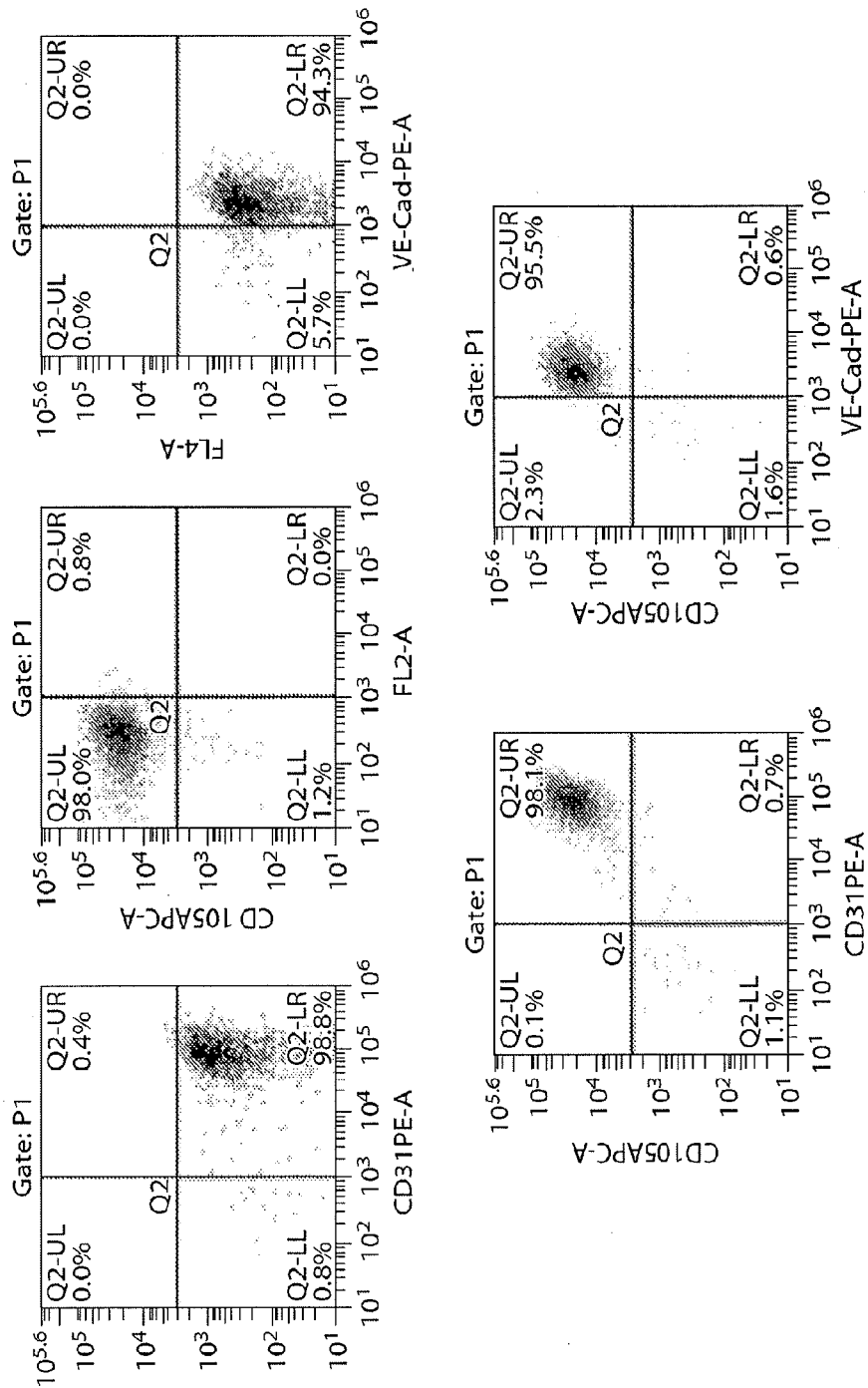
FIGS. 3A-3B. Characterization of advanced differentiation morphology of PVE-HE. This Figure shows the phenotype and morphology of ADM cells that have differentiated into PVE-HE. The ADM cells show the PVE-HE phenotype CD31$^+$CD144(VE-Cad)$^+$CD105$^+$ at this stage of differentiation (FIG. 3A). ADM cells were also analyzed for morphologic changes (FIG. 3B).
Figure 3B:
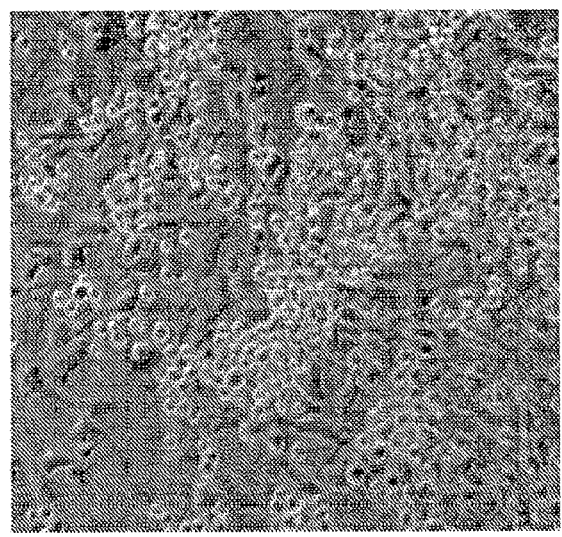

Fourth, after 120 hours post PVE-HE differentiation initiation, advanced differentiation morphology (ADM) cells were analyzed for morphologic changes (FIG. 3B) and successful PVE-HE differentiation. Briefly, a small sample of cells was subjected flow cytometric analysis of lineage-specific markers CD31 (PECAM), CD105 (Endoglin), CD144 (VE-Cadherin). The ADM cells show the PVE-HE phenotype $CD31^+CD144^+CD105^+$ at this stage of differentiation (FIG. 3A).

Example 2—Generating Detached Megakaryocytic Lineage-Specific Progenitors (MLPs) from Human iPS-Derived PVE-HE Cells First, initiation of MLP differentiation was performed 120 hours after initiating PVE-HE differentiation. Briefly, DIM medium containing 50 ng/ml BMP4, 50 ng/ml bFGF, and 50 ng/ml VEGF was removed and replaced with MLP Derivation and Expansion medium (MLP-DEM, also referred to as APEL or Stemline II, as shown in FIG. 1) comprised of Iscove's modified Dulbecco's medium (IMDM), Ham's F-12 nutrient mixture, Albucult (rh Albumin), Polyvinylalcohol (PVA), Linoleic acid, SyntheChol (synthetic cholesterol), Monothioglycerol (a-MTG), rh Insulin-transferrin-selenium-ethanolamine solution, protein-free hybridoma mixture II (PFHMII), ascorbic acid 2 phosphate, Glutamax I (L-alanyl-L-glutamine), Penicillin/streptomycin, Stem Cell Factor (SCF) at 25 ng/ml, Thrombopoietin (TPO) at 25 ng/ml, Fms-related tyrosine kinase 3 ligand (FL) at 25 ng/ml, Interleukin-3 (IL-3) at 10 ng/ml, Interleukin-6 (IL-6) at 10 ng/ml, and Heparin at 5 Units/ml. Cells were then incubated for up to 8 days at 37° C. with 5% $CO_2$. MLP differentiation was maintained for 8 days.

TABLE 1

MLP/MK marker comparison

|  | Matured MLPs | Matured MKs |
| --- | --- | --- |
| CD43 | 95.9% | 98.5% |
| CD41 | 89.3% | 91.4% |
| CD61 | 77.2% | 89.7% |
| CD42a | 66.3% | 88.8% |
| CD144 | 57.6% | 15.1% |
| CD31 | 57.0% | 80.6% |
| CD29 | 40.4% | 96.2% |
| CD45 | 40.3% | 66.1% |
| CD13 | 40.4% | 59.4% |
| CD34 | 30.3% | 44.1% |
| CD309 | 28.4% | 73.2% |
| CD71 | 26.4% | 59.6% |
| CD90 | 19.8% | 2.0% |
| CD105 | 7.5% | 46.0% |
| CD56 | 3.5% | 3.3% |
| CD14 | 4.4% | 4.7% |
| CD143 | 2.2% | 6.8% |
| CD15 | 1.6% | 11.0% |
| CD3 | 2.8% | 4.2% |
| CD117 | 2.7% | 10.2% |
| CD184 | 0.6% | 8.5% |
| CD11c | 0.4% | 2.5% |
| CD73 | 0.0% | 1.5% |

Table 1 shows comparative flow cytometric analysis of marker expression by matured MLP and matured MK cells. The analysis characterizes the phenotype of PVE-HE-derived MLP cells prior to crypopreservation and subsequent differentiation into MK cells of the defined phenotype.

Figure 4:
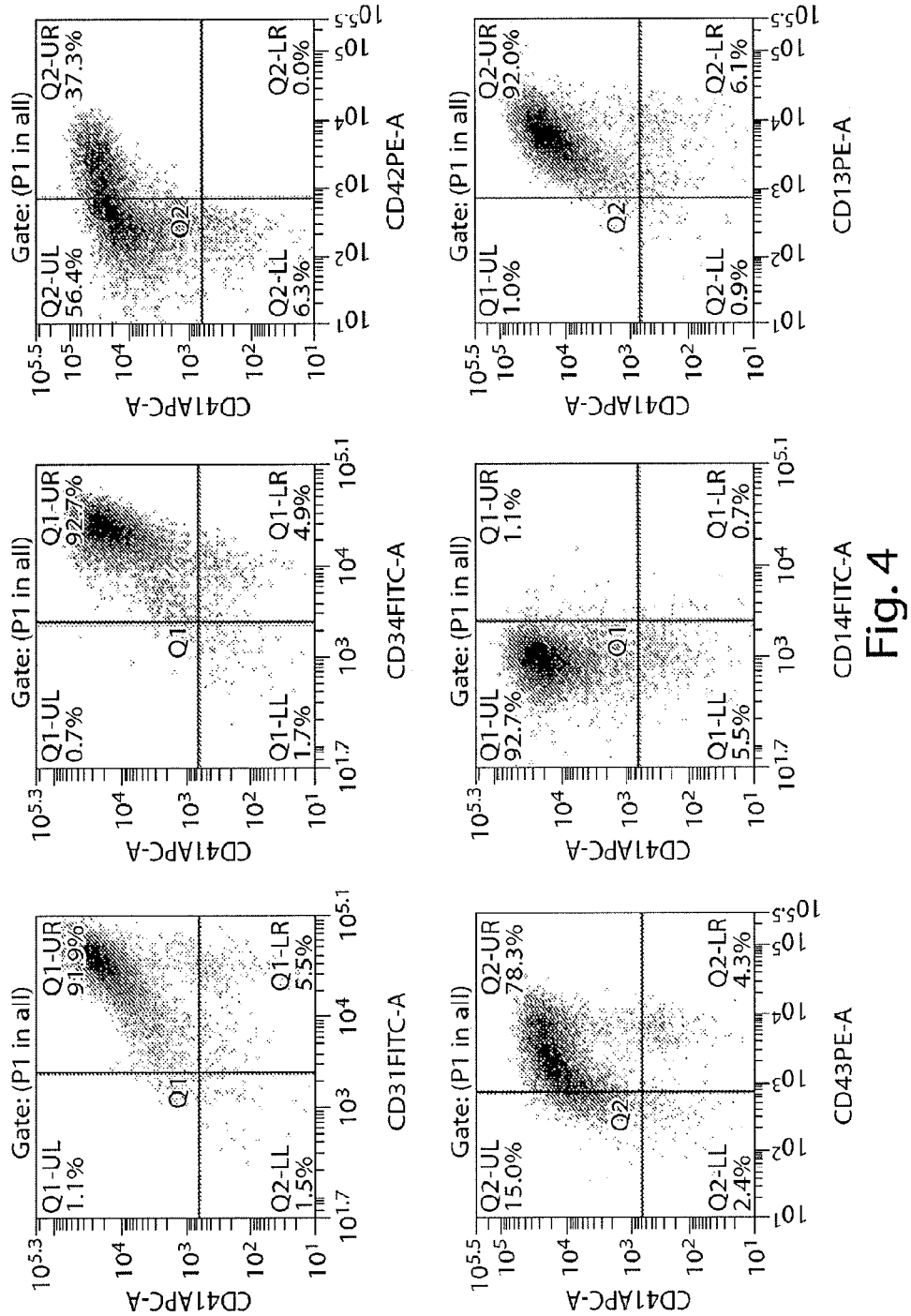
FIG. 4. Characterization of iPS-PVE-HE-derived megakaryocytic lineage-specific progenitors (MLPs) by flow cytometry. This Figure shows the phenotype of human iPS-PVE-HE-MLP cells as CD34$^+$CD31$^+$CD41a$^+$CD43$^+$CD13$^+$CD14$^-$CD42b$^{-/+}$.
Figure 5A:
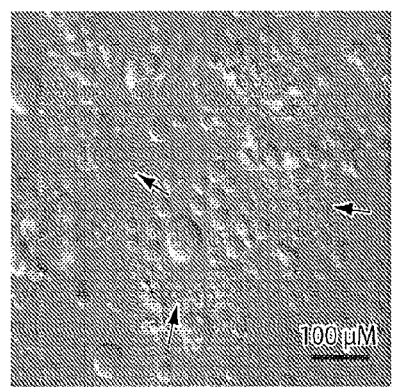
FIGS. 5A-5B. Morphologic analysis of human iPS-PVE-HE-MLP-derived maturing MK cells. This Figure shows nuclei inside MK cells (indicated by "N"), and readily observable proplatelet forming cells with elongated pseudopodia (indicated by arrows). At 72 hours post initiation of platelet differentiation, very large polyploidy MKs (50 µM) became abundant with progression of maturation (FIGS. 5A & B. Scale bar in 5A is 100 µM, N in 5B indicates nucleus inside MK). From between 72-96 hours proplatelet forming cells with elongated pseudopodia were readily observed microscopically.
Figure 5B:
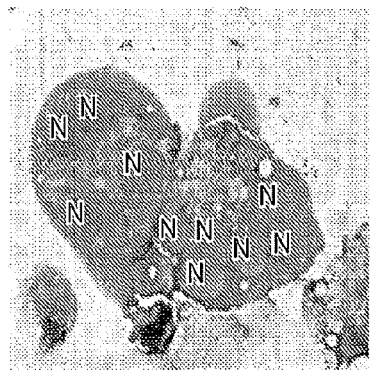
Figure 5C:
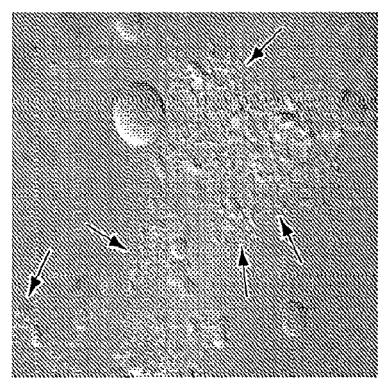

Second, floating and semi-detached MLPs on top of the attached cell population were collected by wash with mild force using serological pipette. Medium containing these MLPs was transferred into conical tubes and centrifuge at 300×g for 5 minutes to collect the MLPs. Medium was discarded and MLP pellet was resuspended in phosphate buffered saline and analyzed for morphology (FIG. 5) and by flow cytometry using markers seen in Table 1. Selected results seen in FIG. 4. Results demonstrate that MLPs collected at this stage are mainly (over 90%) comprised of two populations, one characterized by a relatively immature MLP population represented by $CD41a^+CD31^+CD34^+CD14^-CD13^+CD42b^-$, and a more matured MLPs population represented by $CD41a^+CD31^+CD34^+CD14^-CD13^+CD42b^+$.

Third, MLP cells were cryopreserved. Briefly, cryopreservation of MLPs was achieved using the cell freezing medium CS10 (Sigma) containing 10% DMSO.

Example 3—Generating Mature Platelets from Human iPS-PVE-HE-MLP-Derived Megakaryocytes (MK)

First, initiation of platelet differentiation was performed using human iPS-PVE-HE-derived MLP cells, as described above. MLPs were seeded onto a non-adherent surface in MK media (MK-M) comprised of Iscove's Modified Dulbecco's Medium (IMDM) as basal medium, human serum albumin, iron-saturated transferrin, insulin, b-mercaptoethanol, soluble low-density lipoprotein (LDL), cholesterol, TPO at 30 ng/ml, SCF at 1 ng/ml, IL-6 at 7.5 ng/ml, IL-9 at 13.5 ng/ml, Y27632 at 5 µM, and Heparin at 5-25 units/ml. Cells were then incubated at 37° C. in 5% $CO_2$ for 3 days.

In some instances, the MLPs were seeded onto a non-adherent surface in culture medium comprised of Iscove's modified Dulbecco's medium (IMDM), Ham's F-12 nutrient mixture, Albucult (rh Albumin), Polyvinylalcohol (PVA), Linoleic acid, Linolenic acid, SyntheChol (synthetic cholesterol), Monothioglycerol (a-MTG), rh Insulin-transferrin-selenium-ethanolamine solution, protein-free hybridoma mixture II (PFHMII), ascorbic acid 2 phosphate, Glutamax I (L-alanyl-L-glutamine), Penicillin/streptomycin, TPO at 30 ng/ml, SCF at 1 ng/ml, IL-6 at 7.5 ng/ml, IL-9 at 13.5 ng/ml, Y27632 at 5 µM, and Heparin at 5-25 units/ml. Cells were then incubated at 37° C. in 5% $CO_2$ for 3 days.

Figure 6A:
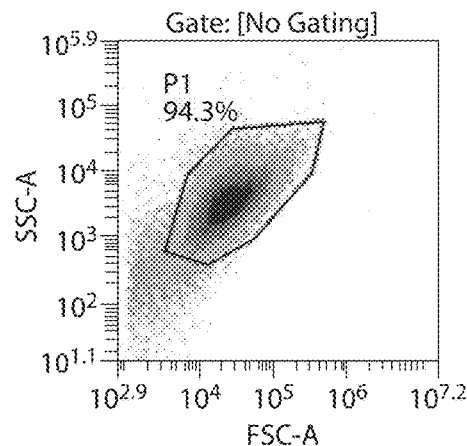
FIGS. 6A-6E. Comparison of phenotype and purity of platelet preparations from different sources. This Figure shows flow cytometric analysis of the morphology and cell surface expression of CD41a and CD42b on peripheral blood derived human platelets and iPS-PVE-HE-MLP-MK-derived platelets. Between 72-96 hours post initiation, the amount of CD41a+CD42b+ platelets increased dramatically, reaching levels as high as about 70% (FIG. 6D).
Figure 6B:
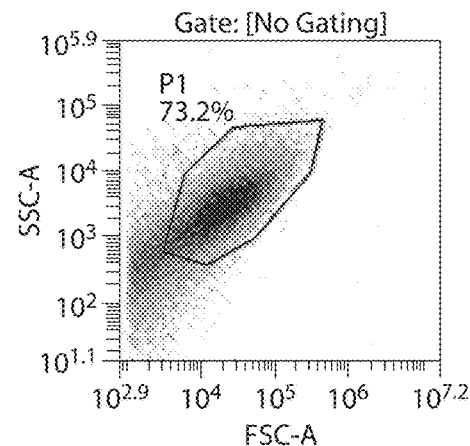
Figure 6C:
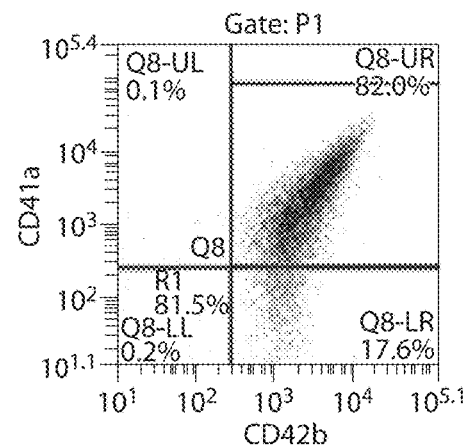
Figure 6D:
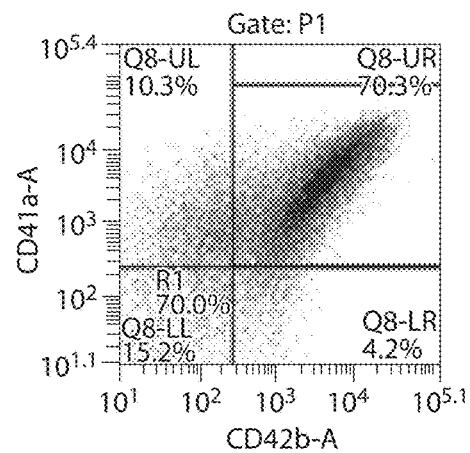
Figure 6E:
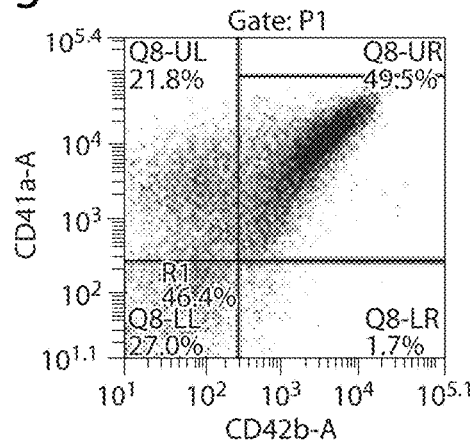

Second, iPS-PVE-HE-MLP-derived maturing MK cells were analyzed. At 72 hours post initiation of platelet differentiation, very large polyploid MKs (50 µM) became abundant with progression of maturation (FIGS. 5A & B. Scale bar in 5A is 100 µM, N in 5B indicates nucleus inside MK). From between 72-96 hours proplatelet forming cells with elongated pseudopodia were readily observed microscopically. (FIGS. 5A & 5C, indicated by arrows), and emerging amounts of CD41a+CD42b+ platelet particles were detected using flow cytometric analysis (FIG. 6). In FIG. 6 the cells in "A" were circulating human platelets, "B" is hES-PVE-HE-MLP, "C" is peripheral blood derived human platelets, "D" is iPS-PVE-HE-MLP, and "E" is hES-PVE-HE-MLP). At 84 hours post initiation, the amount of CD41a+CD42b+ platelets increased dramatically, reaching levels as high as 70% (FIG. 6D).

Third, high quality platelets were harvested without harming maturing MKs in cultures for at least 3-5 consecutive days and possibly longer, maximizing the yield of platelets from MLPs at least 3-5 times. To separate large MKs from platelet containing media, the cell suspension was centrifuged at 50×g for 10 minutes, supernatant removed and MK cell pellets re-suspended with fresh MK-M, allowing them to produce more platelets later. To separate platelets from proplatelets, large cell debris and small MKs, a BSA/HSA gradient sedimentation method was applied to obtain a purer population of platelets from the supernatant of the 50×g centrifugation. Purified platelets were suspended with MK-M and maintained at room temperature. Quality of platelets with respect to granularity, transparency, size, and cell surface marker expression were characterized by FACS analysis and compared to peripheral blood derived human platelets. (FIG. 6A-E). Purified platelets were stored in MK-M media at room temperature within a non-adherent surface, securing a minimal loss of functional platelets.

Example 4—Analysis of Mature Platelets from iPS-PVE-HE-MLP-Derived Megakaryocytes (MK)

Figure 7:
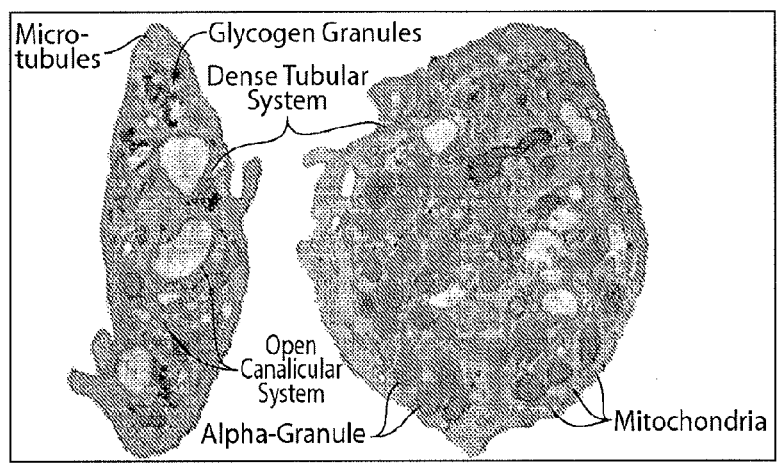
FIG. 7. Ultrastructural comparison of peripheral blood derived human platelets and platelets produced by differentiation of human induced pluripotent cells (hiPSC-PLTs) by transmission scanning microscopy. This Figure shows the similarities in cellular characteristics of peripheral blood derived human platelets and hiPSC-PLTs of the present disclosure. The hiPSC-PLTs are discoid.
Figure 7:
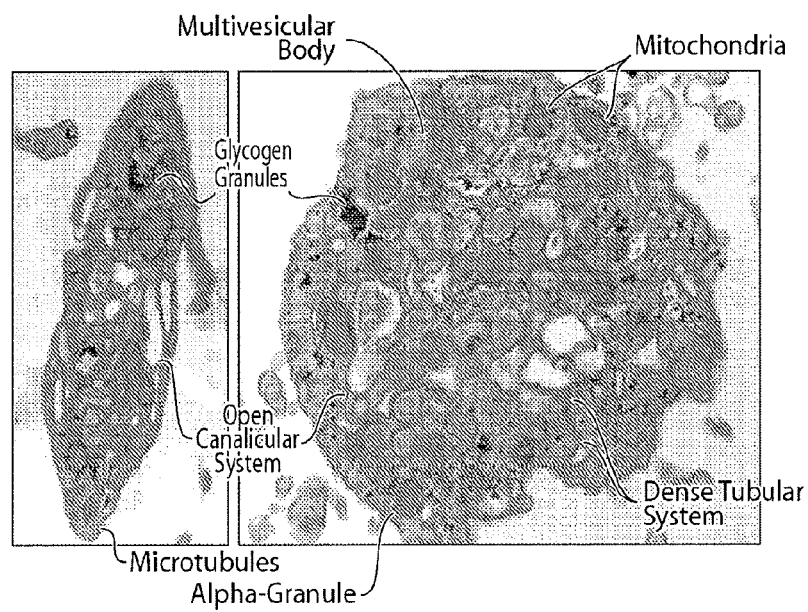
Figure 8:
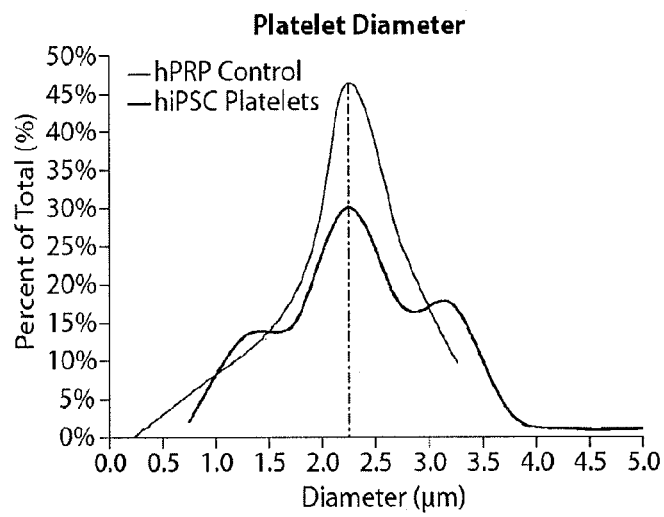
FIG. 8. Comparison of peripheral blood derived human platelets (hPRP) and hiPSC-PLTs. This Figure shows similarities between the two cell preparations in platelet diameter (left panel), and expression of structural cell proteins beta1-tubulin and F-actin (via FITC-phalloidin binding) (right panel), which are involved in activation induced platelet shape changes. Negative Hoechst staining (top right) confirmed the absence of nuclear DNA in iPSC-PLTs and donor-derived PLTs.
Figure 8:
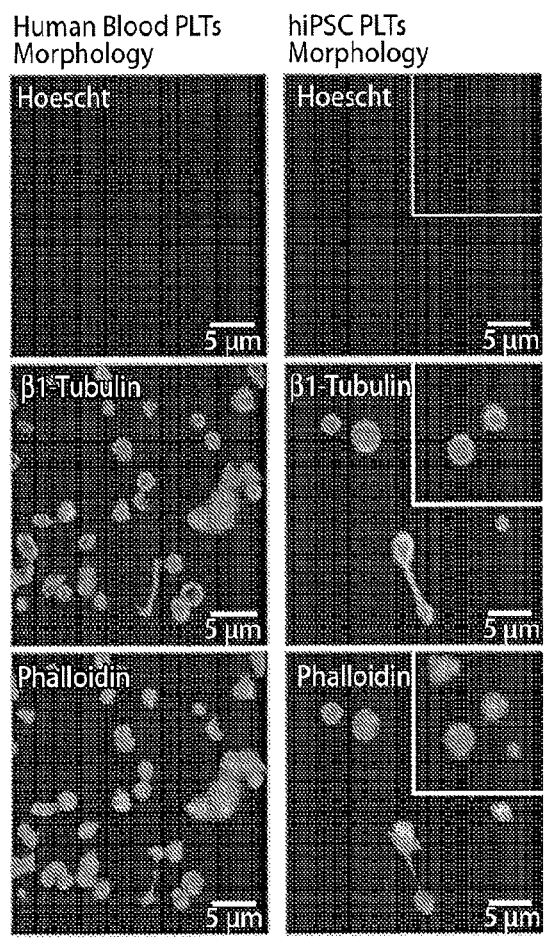
Figure 9:
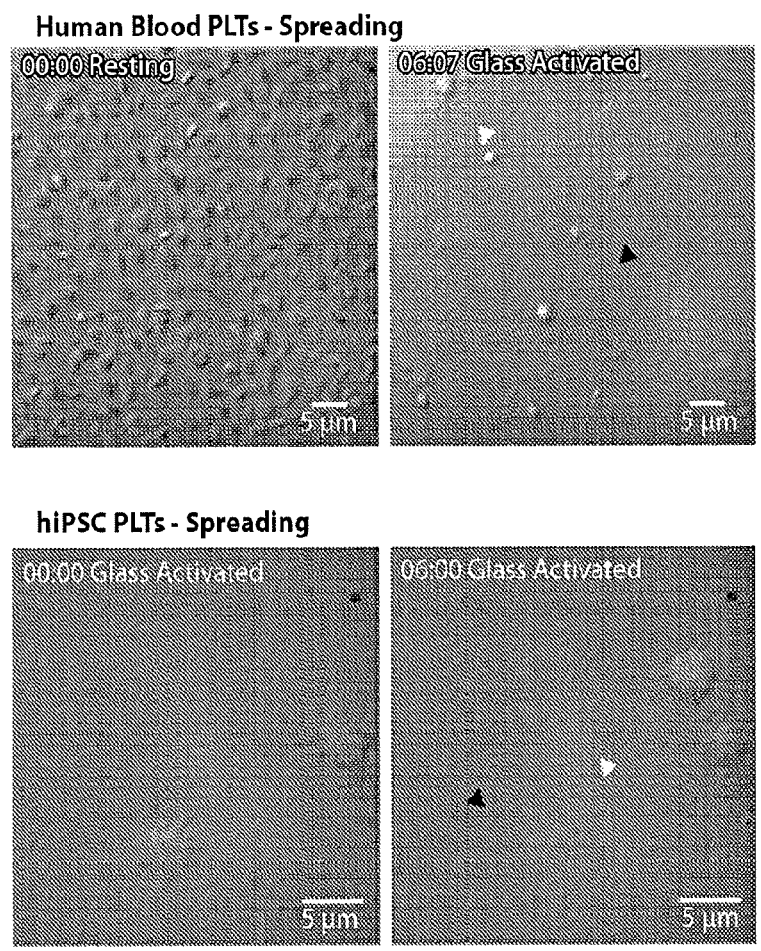
FIG. 9. Comparison of peripheral blood derived human platelets and hiPSC-PLTs. This Figure shows the similarities in morphologic characteristics of peripheral blood derived human platelets and hiPSC-PLTs of the present disclosure using differential interference contrast (DIC) live-cell microscopy. Both the peripheral blood derived human platelets and the hiPSC-PLT show pseudopodia emission indicative of activation when bound to the negatively charged glass surface.
Figure 10A:
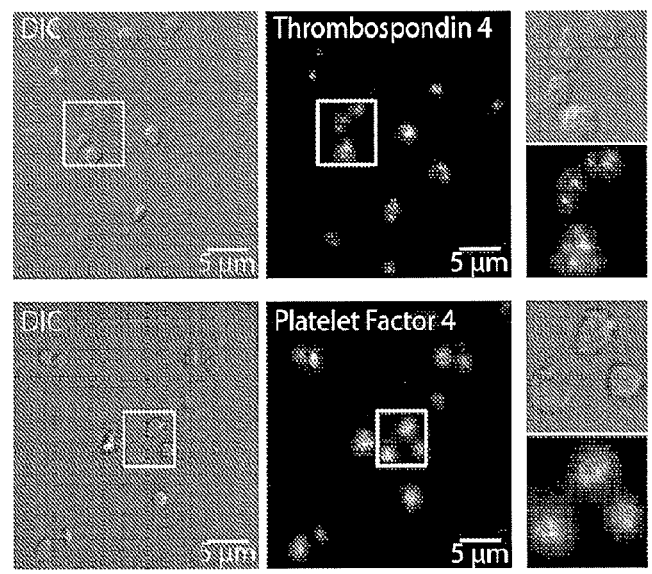
FIGS. 10A-10B. Comparison of peripheral blood derived human platelets and hiPSC-PLTs. This Figure shows the similarities of alpha-granule expression as demonstrated by Thrombospondin 4 (TSP4) and Platelet Factor 4 (PF4) labeling. TSP4 and PF4 are chemokines released from alpha-granules of activated platelets. hiPSC-PLTs (FIG. 10B) were seen to have normal alpha-granule expression relative to normal human platelets (FIG. 10A), as demonstrated by TSP4 and PF4 labeling.
Figure 10B:
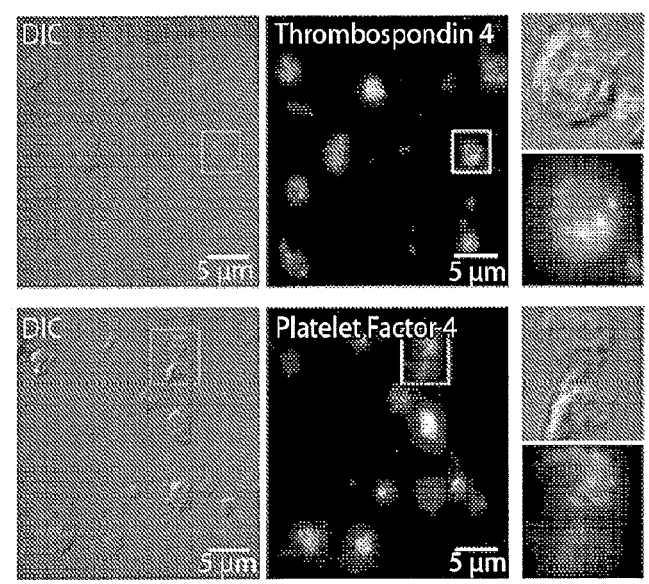

First, iPS-PVE-HE-MLP-derived platelets (hiPSC-PLTs) were analyzed for morphology. Immunoflouresensce and transmission electron microscopic analysis was performed according to methods previously described (Cell Research 2011 21:530-45). hiPSC-PLTs were found to be discoid and mostly ultrastructurally identical to circulating human PLTs (as demonstrated by transmission electron microscopy, FIG. 7). hiPSC-PLTs were comparable on average size with circulating human PLTs (2.38 µm±0.85 µm versus 2.27 µm±0.49 µm) as demonstrated by DIC and β1-tubulin IF microscopy (FIG. 8). hiPSC-PLTs spread on glass—form both filopodia and lamelopodia (as demonstrated by DIC live-cell microscopy images shown in FIG. 9). hiPSC-PLTs were anucleate, and comparable to circulating human PLTs (as demonstrated by Hoechst staining, FIG. 8). hiPSC-PLTs were seen to have normal tubulin cytoskeleton relative to circulating human PLTs (as demonstrated by β-tubulin labeling, FIG. 8). hiPSC-PLTs were seen to have normal filamentous actin relative to circulating human PLTs (as demonstrated by phalloidin labeling, FIG. 8). hiPSC-PLTs were seen to have normal alpha-granule expression relative to circulating human PLTs (as demonstrated by TSP4 and PF4 labeling in FIGS. 10A &10B).

Figure 11:
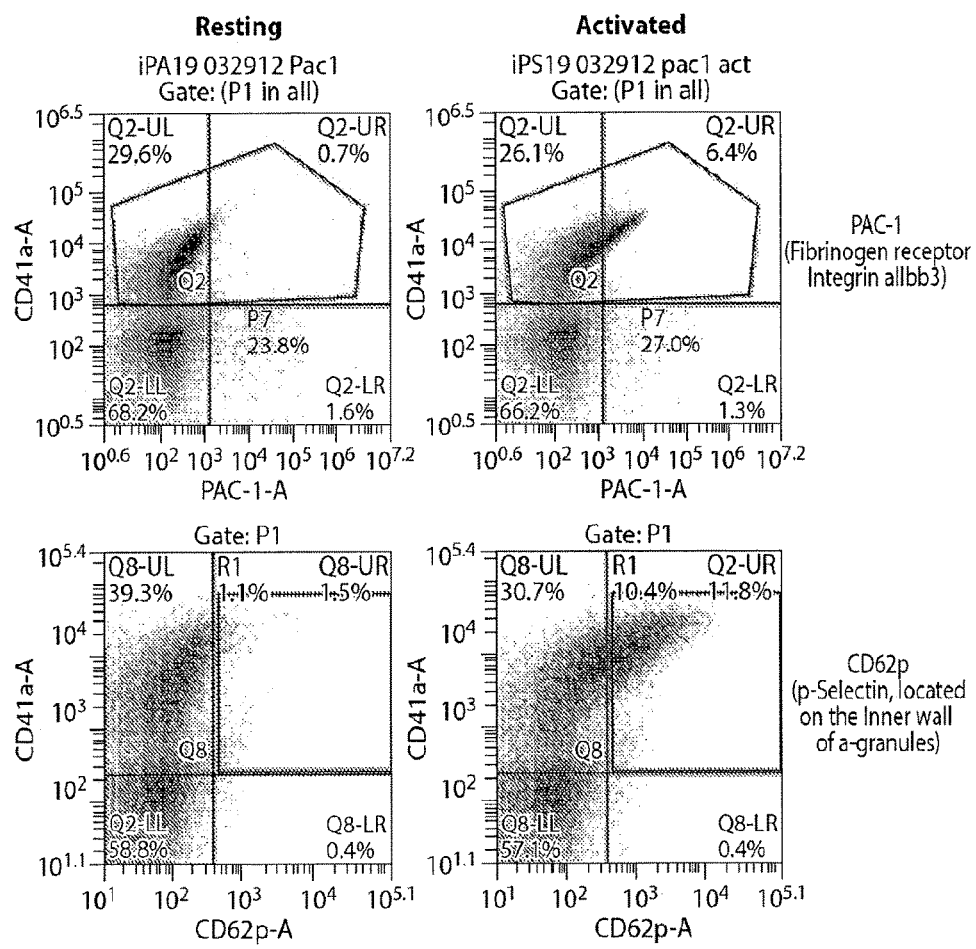
FIG. 11. Functional evaluation of hiPSC-PLTs. This Figure shows the in vitro activation of hiPSC-PLTs with thrombin as measured by the upregulation of two adhesion molecules CD62p and αIIbβIII (as measured by the PAC-1 Ab).

Second, hiPSC-PLTs were analyzed for functionality using an in vitro activation assay measuring the cell adhesion molecule expression on an activated platelet. Briefly, two adhesion molecules were analyzed, using an anti-CD62p antibody, and the PAC-1 antibody. PAC-1 recognizes the αIIbβIII integrin. Both CD62p and αIIbβIII are expressed on the surface of activated platelets. The assay was performed according to methods described previously (Cell Research 2011 21:530-45). In response to thrombin exposure, both PAC-1 and P-selectin binding were increased (FIG. 11).

Third, hiPSC-PLTs were analyzed for functionality using an in vivo assay system measuring thrombus formation in macrophage-depleted NOD/SCID mice. Briefly, intravital microscopy of cremaster muscle arterioles was performed as previously described (Cell Research 2011 21:530-45). Macrophage-depleted NOD/SCID mice were anesthetized by intraperitoneal injection of ketamine (125 mg/kg) and xylazine (25 mg/kg). A tracheal tube was inserted and the mouse was placed on a thermo-controlled blanket. After incision of the scrotum, the cremaster muscle was exteriorized onto an intravital microscopy tray. The muscle preparation was superfused with thermo-controlled (37° C.) and aerated (95% N2, 5% CO2) bicarbonate-buffered saline throughout the experiment. The cremaster muscle arteriolar wall was injured by micropoint laser ablation using a Micropoint Laser System (Photonics Instruments). The developing mouse platelet thrombus was visualized by infusion of Dylight 649-conjugated anti-mouse CD42c antibodies (Emfret Analytics, 0.05 µg/g body weight) through a jugular cannulus. Calcein AM-labeled hPLT, iPSC-PLT, and ESC-PLT, $3 \times 10^6$, were also infused with or without ReoPro, 100×g, into mice. Two to four thrombi were generated in one mouse. Fluorescence and brightfield images were recorded using an Olympus BX61W microscope with a 60×/1.0 NA water immersion objective and a high speed camera (Hamamatsu C9300) through an intensifier (Video Scope International). Data were collected for 5 min following vessel wall injury and analyzed using Slidebook v5.0 (Intelligent Imaging Innovations). The results seen in FIG. 12A are an indication that hiPSC-PLTs contribute to clot formation in an in vivo setting. hiPSC-PLT's functional capabilities were also determined to be mediated by αIIbβIII. Specifically, hiPSC-PLTs were pretreated with ReoPro, a Fab fragment of a human-murine chimeric monoclonal antibody that binds specifically to αIIbβIII and inhibits platelet function (FIG. 12B). Asterisks indicate a statistically significant difference compared to controls not treated with ReoPro ($p<0.01$ versus control, Student's t-test).

Figure 13:
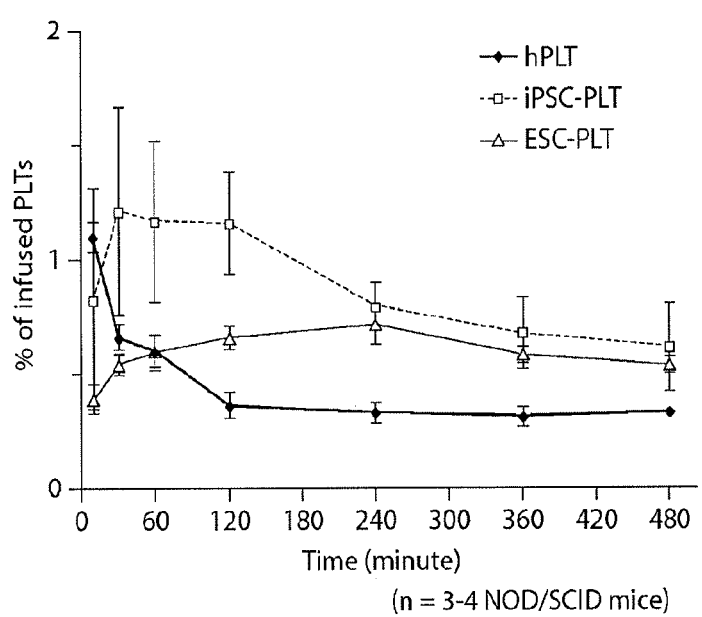
FIG. 13. Kinetics of PLTs in macrophage-depleted NOD/SCID mice after infusion. This Figure shows a detectable circulation of hiPSC-PLTs and hESC-PLTs of eight hours.
Figure 14A:
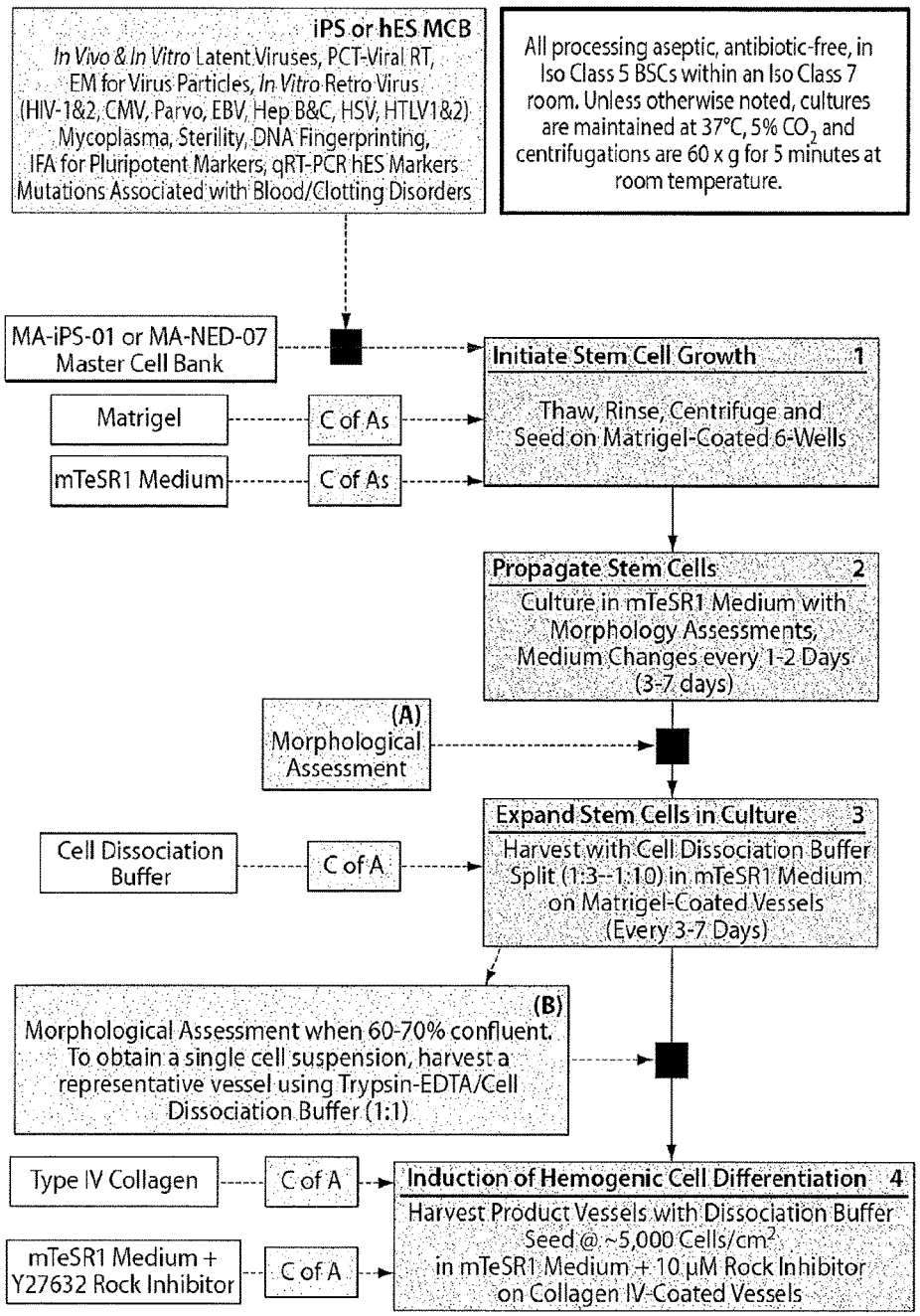
FIGS. 14A-14E. Exemplary process flow diagram for production of platelets from pluripotent stem cells.
Figure 14B:
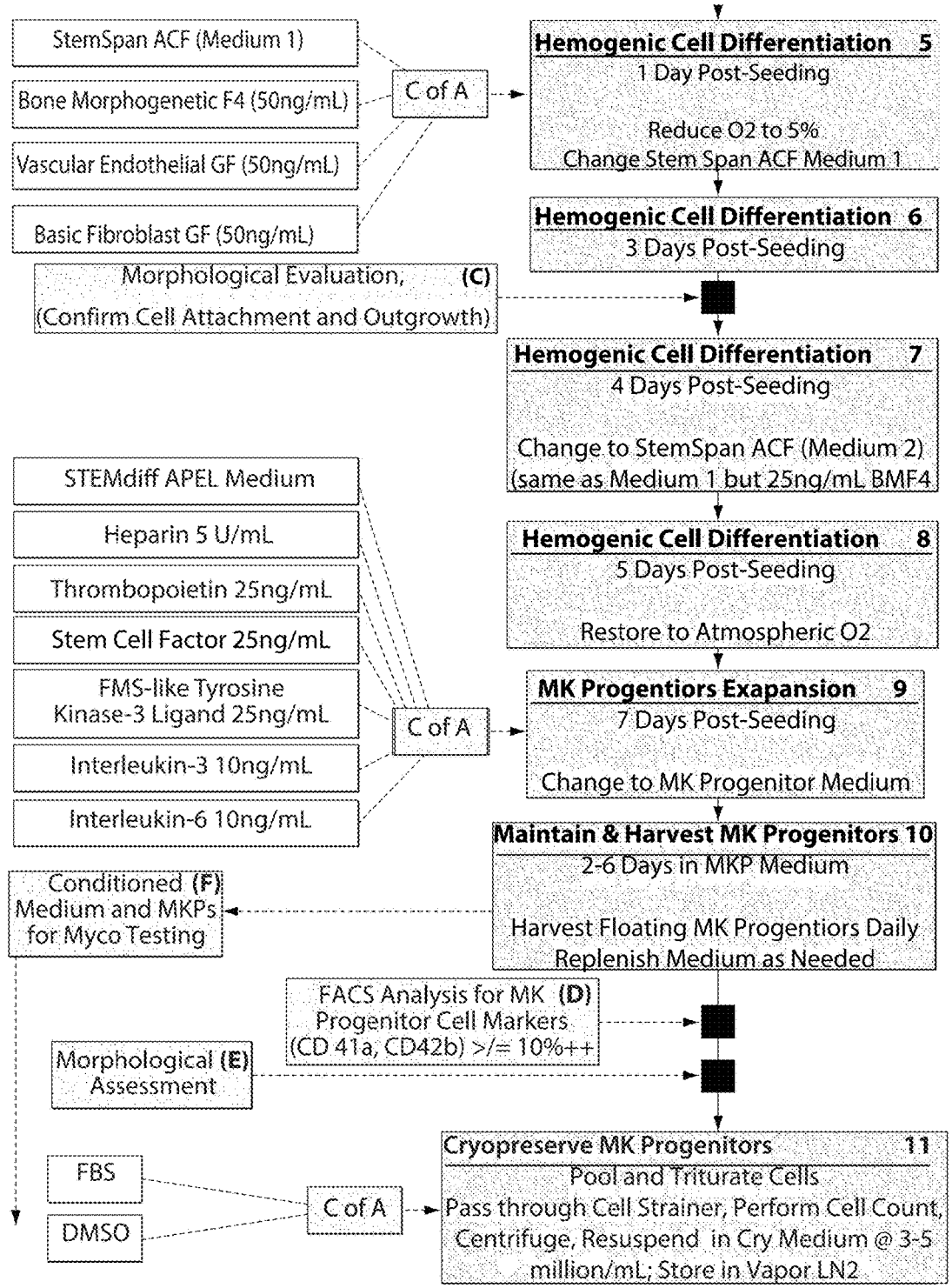
Figure 14C:
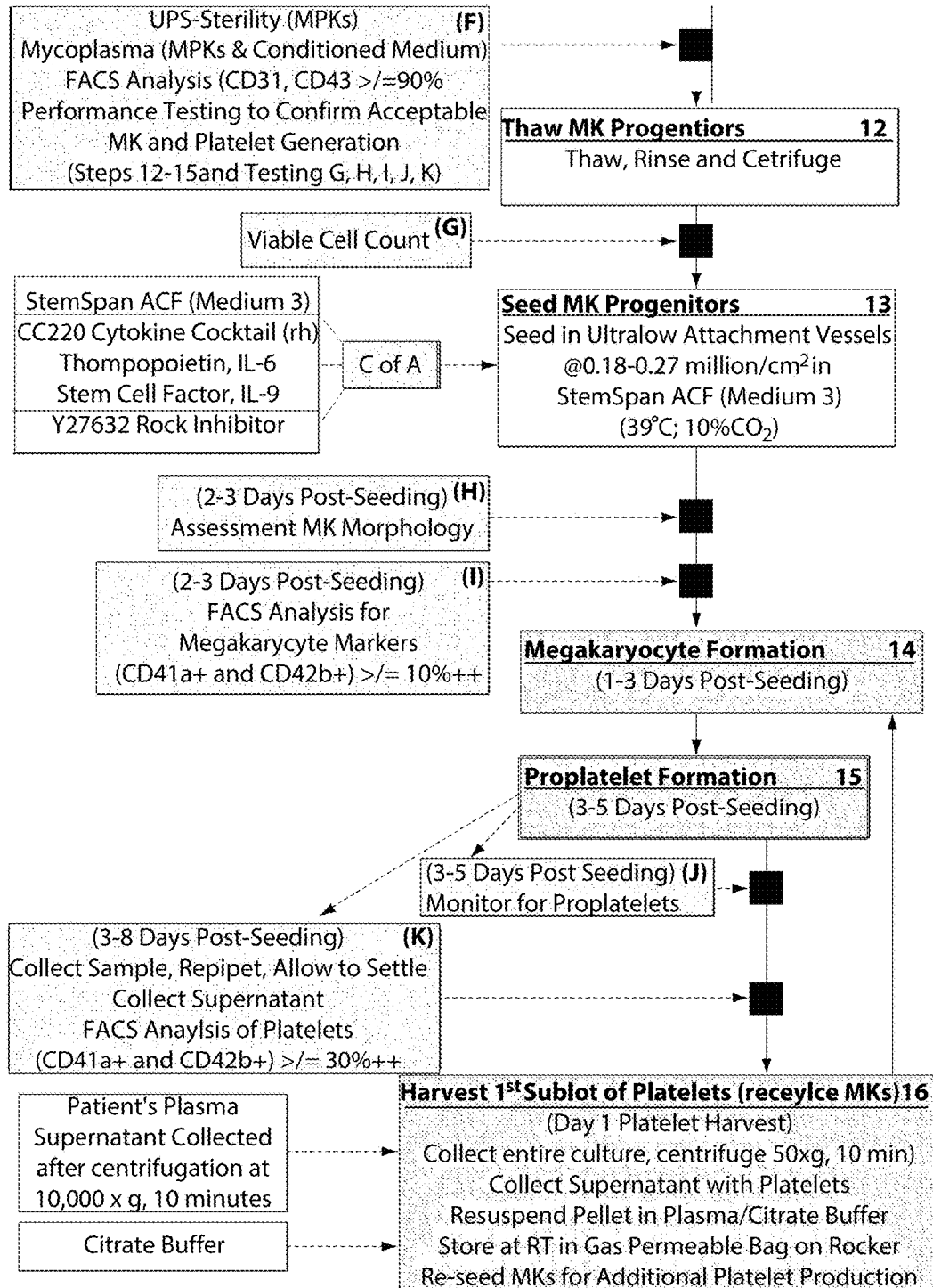
Figure 14D:
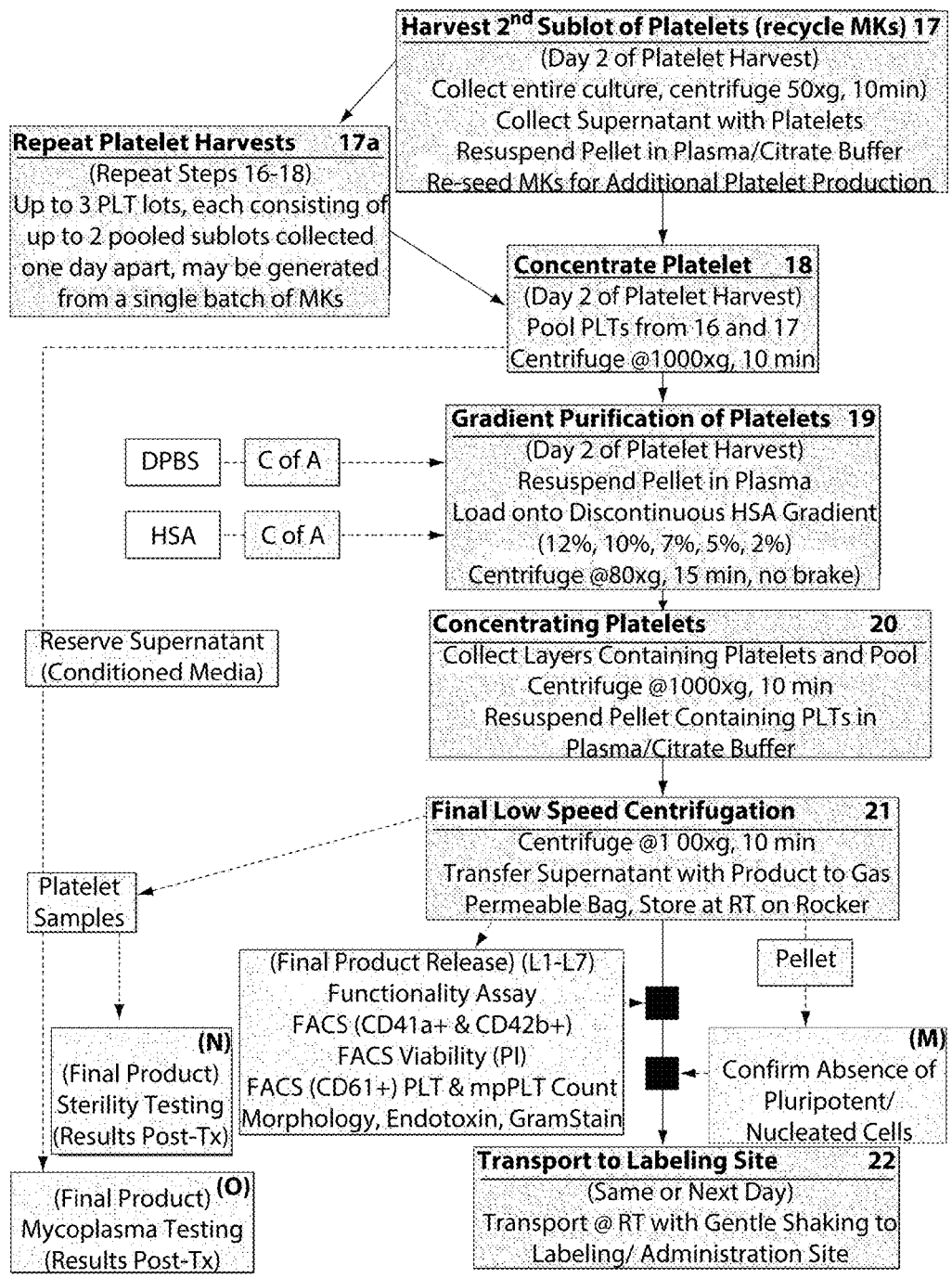
Figure 14E:
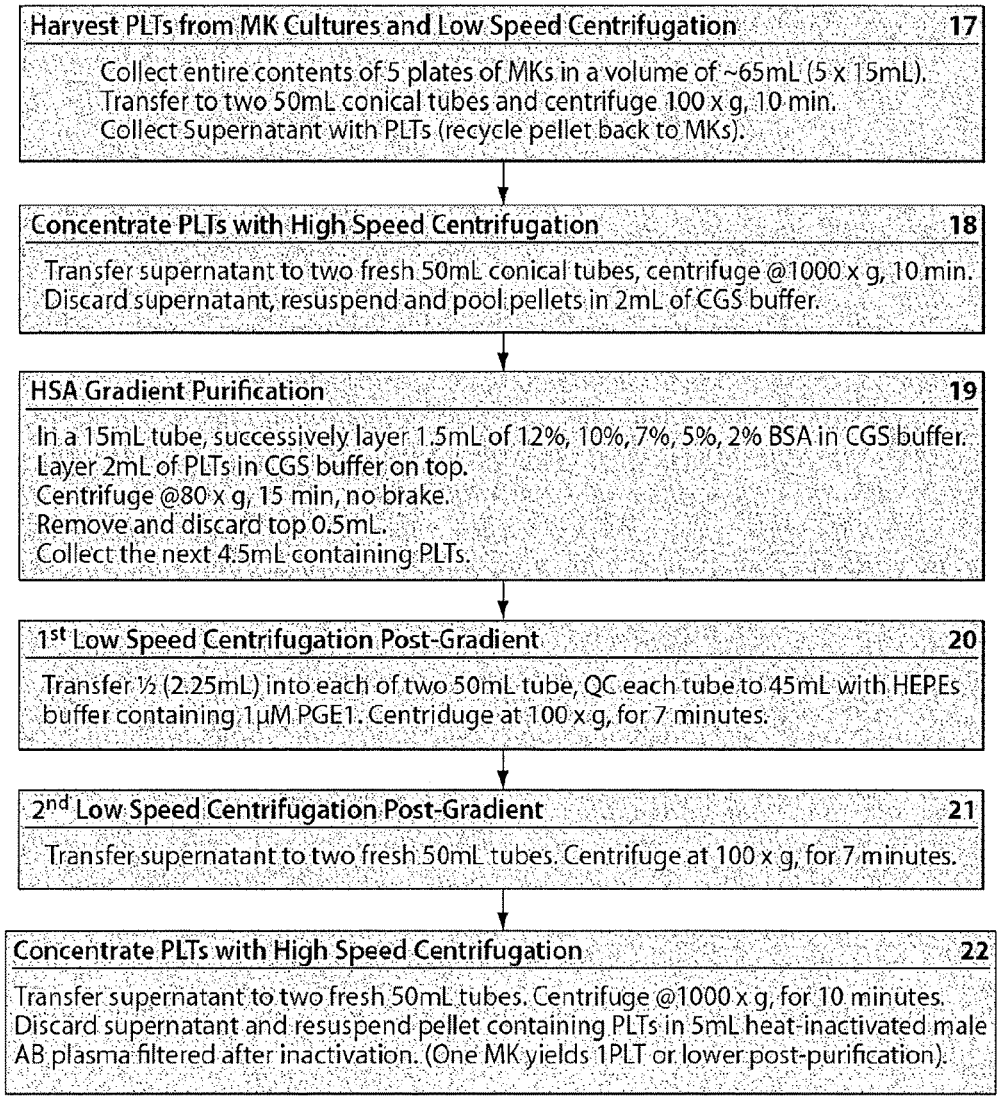

Fourth, the kinetics of hiPSC-PLTs in macrophage-depleted NOD/SCID mice after infusion were determined. To determine whether the kinetics of hiPSC-PLT and ESC-PLT is similar to that of hPLT in vivo, iPSC- or ESC-PLTs were infused into macrophage-depleted NOD/SCID mice, and blood collected at various time points was analyzed by flow cytometry. Briefly, macrophages were depleted by intravenous injection of liposome-encapsulated clodronate as described previously. Clodronate-liposomes were injected into mice through a tail vein at Day 0 (100 µl) and Day 2 (50 µl). At Day 3, human platelet-rich plasma was obtained by centrifugation of sodium citrate-treated blood at 200×g for 25 min and centrifuged at 800×g for 10 min in the presence of 0.5 µM PGE1 and 10% citrate buffer. The pellet was resuspended with HEPES-Tyrode buffer containing 0.15 µM PGE1 and 10% citrate buffer and centrifuged at 800×g for 5 min. Platelets were resuspended in HEPES-Tyrode buffer containing 0.1% fatty acid-free BSA. Isolated human platelets (hPLT, $1.5\times10^7$), induced pluripotent stem cell-derived platelets (hiPSC-PLT, $1.5\times10^7$) of the present disclosure, and embryonic stem cell-derived platelets (ESC-PLT, $1.0\times10^7$) of the present disclosure were intravenously infused into macrophage-depleted mice. Mouse blood, 30 µl, was collected through a jugular vein at different time points (10, 30, 60, 120, 240, 360, and 480 minutes) and analyzed by flow cytometry using APC-conjugated anti-human CD41 and Dylight 488-conjugated anti-mouse CD42c antibodies. Results demonstrate that hiPSC-PLTs circulate for several hours in macrophage-depleted NOD/SCID mice (FIG. 13).

Example 5. Production of Platelets from Pluripotent Cells

This example provides further exemplary methods of producing platelets from pluripotent stem cells.

As noted above, hESC-PLT and hiPSC-PLT are human platelets which are produced ex vivo from human embryonic and induced pluripotent stem cells. Initial in vitro and in vivo characterization described above has demonstrated that both hESC-PLT and hiPSC-PLT are morphologically and functionally comparable to human donor platelets. For example, hiPSC-PLT were able to spread on a glass substrate.

The production of bulk intermediate (MK progenitors) is initiated with the thaw of vials from an approved hiPSC or hESC master cell bank (MCB). The process flow chart for the production of bulk intermediate is presented in FIG. 14A-E. Cryovials containing 1-2 million hiPSC or hESC master or working cell banks are removed from the vapor phase of cGMP liquid nitrogen storage and transferred to the clean room (ISO Class 7). All processing is performed in a certified biosafety cabinet (ISO Class 5 BSC). Following thaw and wash to remove DMSO; cells are seeded on Matrigel coated vessels in mTeSR1 defined culture media. Care is taken to maintain the cells as aggregates. Plates are labeled with the date, lot number, and passage number and the lid of each well is labeled a unique number (e.g. 1-6). Seeded plates are placed in a 37° C., 5% $CO_2$ incubator. Cultures are inspected daily using a stereo-microscope and an inverted light microscope. Observations regarding colony size, cellular morphology; including the extent of differentiation, and media color are recorded on a work sheet. mTeSR1 medium is changed typically every 1-2 days until cultures are 60-90% confluent. When morphology and confluence evaluations indicate that the cultures need to be passaged, colonies are harvested using cell dissociation buffer. Care is again taken to maintain the cells as aggregates. Cultures are re-seeded onto Matrigel coated vessels in mTeSR1 media. Based on the $cm^2$ harvested and the $cm^2$ to be seeded, cells are typically split at a ratio of 1:4 to 1:8 every 3-7 days depending on the yield of stem cells required. Seeded cultures are returned to a 37° C., 5% $CO_2$ incubator. Stem cells may be passed 1-6 times before induction of hemogenic differentiation depending on the required lot size.

Three day post-seeding for hemogenic cell differentiation, cultures are examined to confirm cell attachment and outgrowth. At this stage cultures are typically low density with attached cells covering less than 10% of the total surface area. Well attached cells should demonstrate outgrowth with a significant transition from pluripotent stem cell morphology to differentiated cells: larger cells with significantly more cytoplasm relative to the size of the nucleus growing more diffusely with no clear colony borders.

When the stem cell expansion phase is estimated to meet cell yield requirements, hemogenic differentiation is initiated. A representative vessel is sacrificed for harvest and a single cell suspension is created. The cell concentration is quantified to establish culture seeding parameters, with the remaining cells discarded. Colonies are carefully harvested using cell dissociation buffer and reseeded into collagen IV coated vessels at a density of 5,000 cells/$cm^2$ in mTeSR1 media supplemented with 10 uM Y27632 (ROCK inhibitor). Seeded vessels are placed in a 37° C., 5% $CO_2$ incubator.

The following day the media is removed, taking care to minimize the removal any floating cell clusters, and replaced with StemSpan ACF (StemCell Technologies Inc.) supplemented with recombinant human (rh) BMP-4 at 50 ng/ml, rh VEGF at 50 ng/ml, and rh bFGF at 50 ng/ml. The cultures are transferred to a low $O_2$ (~5%), 37° C., 5% $CO_2$ environment and are left undisturbed for 2 days. After 2 days the cultures are evaluated morphologically for cell attachment and outgrowth. The media is removed, taking care to minimize the removal any floating cell clusters, and replaced with fresh media. The cultures are returned to the low $O_2$ (~5%), 37° C., 5% $CO_2$ environment for an additional 2 days. Following this time period the media is changed once more and the cultures are placed in normoxic culture conditions. After 2 days of normoxic culture the culture media is removed, taking care to minimize the removal of any floating cell clusters, and replaced with MLP medium comprising STEMdiff APEL (StemCell Technologies Inc.) supplemented with 5 Units/ml heparin, rh 25 ng/ml TPO, 25 ng/ml rh SCF, 25/ng rh FL, rh IL-6 and rh IL-3. These conditions are maintained for the next 2-6 days. Cultures undergo daily morphological evaluation to assess the quality of floating MK progenitors. Media changes are not performed, but additional media is added if the culture begins to indicate media depletion (culture media appears yellow). Cultures are periodically sampled and assayed by FACS for CD41a, CD42b expression. When culture morphology and CD41a, CD42b expression (~≥15% double positive) are appropriate, the cultures are harvested Cells are then cryopreserved @ 3-5 million viable MLPs/mL/cryovial in 10% dimethyl sulfoxide, 90% fetal bovine serum cryopreservation medium (Hyclone). Cryopreservation is accomplished by placing vials in freezing container (Nalgene) and then storing in a −80° C. freezer for 1-3 days, followed by transfer to the vapor phase of the cGMP liquid nitrogen storage system.

The production process for the final product hESC-PLT or hiPSC-PLT is initiated with the thaw of approved bulk intermediate. Cryovials containing 3-5 million MLPs which have passed bulk intermediate quality testing are removed from the vapor phase of cGMP liquid nitrogen storage and transferred to the clean room. Cells are seeded into ultra-low attachment (ULA) vessels at approximately $2.3\times10^5/cm^2$ in StemSpan ACF media supplemented with 30 ng/ml rh TPO, 1 ng/ml rh SCF, 7.5 ng/ml rh IL-6, 13.5 ng/ml rh IL-9 and 5 uM Y27632 (ROCK inhibitor). Culture vessels are labeled with the date and lot number and the lid on each vessel is labeled a unique number (e.g. 1-6). Cultures are maintained at 39° C., in a humidified 10% $CO_2$ atmosphere. Typically there is no significant cell expansion during this culture phase. Approximately 3 to 4 days into the culture, large maturing megakaryocytes (MK) will become evident. Cultures are monitored by periodic sampling and FACS analysis for CD41a, CD42b expression. Proplatelet formation is typically first observed after five days in culture. As proplatelet formation progresses and CD41a, CD42b expression increases to approximately 30%-70% the cultures can be harvested (days 6-7).

The harvested media is centrifuged at 50×g to remove the megakaryocyte slurry. The supernatant is removed and centrifuged at 1000×g to concentrate the platelets. The platelets are resuspended and then loaded on to a discontinuous albumin (Human) (HSA) gradient (12%, 10%, 7%, 5% and 2%) to further isolate the platelets. The platelet HSA gradient is centrifuged at 80×g for 15 minutes. Platelets are harvested from the gradient and $PGE_1$ is added to the suspension to prevent activation. Platelets are concentrated by centrifugation at 1000 g for 10 minutes. Currently hESC and hiPSC platelets are stored in culture media. For the purposes of the proposed study, a target product stability of 48 to 72 hours will be investigated. Preliminary studies indicate a minimum of 24 hour stability as determined by PAC1 binding results pre and post storage.

FACS analyses (CD31 and CD43) of the MLP cell population in the bulk intermediate have shown that approximately 98% of the cells are committed to a hemogenic endothelial or hematopoietic lineage and thus have differentiated beyond pluripotency.

Further downstream in the process, cells present during MK differentiation and PLT harvest phase of manufacture have been tested by vWF (von Willebrand Factor) expression. Cells at this phase of manufacture are approximately 100% vWF+. The maintenance of a highly differentiated cell population indicates that the culture is not experiencing a clonal expansion of undifferentiated progenitors.

Preliminary studies indicate a total absence of pluripotent cells in hiPS-derived MK cell populations analyzed by IFA staining for OCT4, NANOG, TRA-1-60, TRA-1-81 SSE3, SSE4 and Alkaline Phosphatase. Additional studies using IFA staining for pluripotent markers will examine populations of hES-derived and hiPS-derived MLPs and MKs, as well as, purified PLTs derived from the MKs, to screen for the presence of pluripotent cells. Spiking studies will be conducted to determine the LODs of this assay to detect stem cells in the various cell populations.

Preliminary studies have been performed to characterize MK populations using FACs analyses for pluripotent markers (SSEA4 and TRA-1-60). Spiking studies have been performed where hES cells were mixed with MKs at 1% and 0.1% concentrations. The results indicate a limit of detection of 0.1%. An initial study characterizing MKs for SSEA4 and TRA-1-60 provided a result of <0.1% (below the assay level of detection) SSEA4/TRA-1-60 positive cells in the MK population.

Referring to FIG. 14, steps 2-3, since stem cells harvested with dissociation buffer are dislodged as cell clumps, accurate cell counts are not possible. For this reason, a representative culture vessel is harvested using Trypsin-EDTA to ensure a single cell suspension. This suspension is counted in a hemocytometer and the harvested cell number is normalized per $cm^2$. Cells used for counting are then discarded. The remaining product cultures are harvested using dissociation buffer and the cell yield is calculated based on the normalized cells/$cm^2$×$cm^2$ harvested. The calculated cell yield is used to set the required cell density/$cm^2$ for seeding vessels to induce hemogenic cell differentiation.

Referring to FIG. 14, step 10, beginning at 2 days in MLP medium and out to 6 days in MLP medium cell samples are taken from representative culture vessels, pooled and assessed for the percentage of CD41a and CD42b doubly positive cells by FACS analysis. CD41a is a subunit of fibrinogen receptor ($\alpha IIb\beta III$) and CD42b is a subunit on von Willebrand Factor receptor (GPIb-V-IX). The expression of both receptors is specific for MK lineages and both are required for platelet function. Early lineage hemogenic endothelial cells are CD41a negative, expressing CD41a during late-stage hemogenic differentiation in hematopoietic progenitors. CD42b is expressed exclusively in mature MKs. At this point, cultures are heterogeneous with a high percentage of CD41+ cells and a low percentage of CD42+ cells (Pineault, et. Al., Megakaryocyte and platelet production from human cord blood stem cells. Methods Mol Biol. 2012; 788:219-47).

Figure 15:
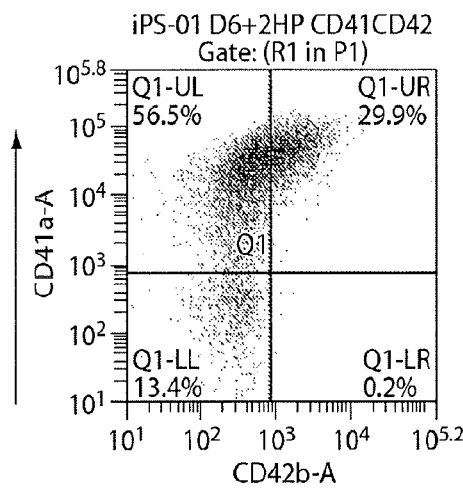
FIG. 15. FACS Analysis, CD41a, CD42b–MLP Derived From hiPSC.

The sample preparation and FACS analysis are performed as follows. Briefly, floating cells are collected and pooled. Using a serological pipette a gentle stream of growth medium is directed towards the culture surface to detach any loosely adherent MLPs and pooled with the free-floating cells. A sample (100-200 μL) of well-suspended pooled cells is collected and centrifuged (160×g for 5 minutes). The pellets is resuspended in DPBS, centrifuged again, and resuspended in DPBS plus 3% FBS (FACS buffer) containing CD41a-APC-conjugated (allophycocyanin) and CD42b-PE-conjugated (phycoerythrin) (BD Bioscience, San Jose, Calif.). Fluorescent conjugated antibodies and the appropriate isotype controls (mouse IgG1k-APC and mouse IgG1k-PE) are incubated in the presence for 15 minutes at room temperature. Labeled cells are then diluted in FACS buffer, centrifuged and resuspended in FACS buffer. FACS analysis is performed by monitoring 10,000 events. Cultures with an acceptable percentage of cells expressing double positive (CD41a+CD42b+) MLPs are harvested and cryopreserved. The tentative minimum specification is 10% double positive cells. Shown in FIG. 15 is a representative two dimensional dot plot for MLPs derived from hiPSC. In that Figure the cell population is 86.4% CD41a+; 31.2% CD42b+ with 29.9% of the population staining double positive.

Figure 16:
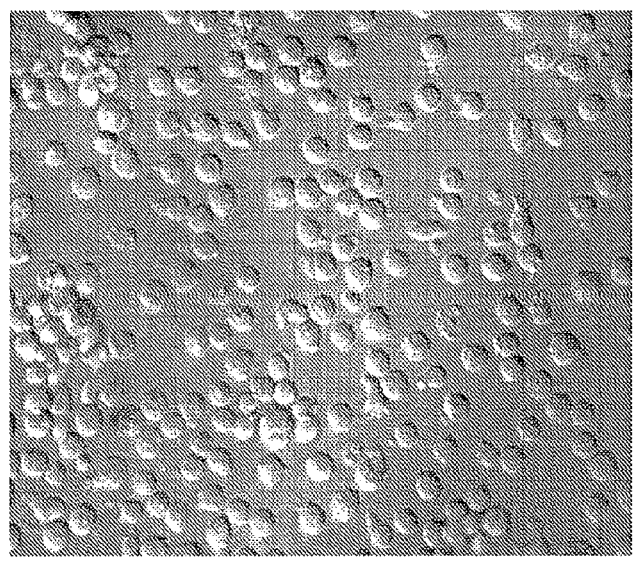
FIG. 16. Representative MLPs Derived from hiPSC.

Prior to harvesting for cryopreservation, MLP cultures are assessed for the approximate percentage of attached cells and the extent of differentiated large cells with low nuclei to cytoplasm ratio. Attached cells should appear as diffuse colonies with no clear colony borders. There should be an abundance of the floating MLPs resting on top of the attached cell population. Viable floating MLPs should appear clear, with minimal birefringence, demarked by a smooth cell membrane. Typically, a surface area of 1 $cm^2$ generates 5,000 to 15,000 MLPs per day. Shown in FIG. 16 is microphotograph of a representative population of MLPs derived from hiPSC line MA-iPS-01 (Hoffman Modulation Contrast, ×400)

Prior to cryopreservation MLPs, viable cell count is performed by trypan blue exclusion using a hemocytometer. Cells are assessed for the viable cell number and the percent viability. Representative vials are tested for mycoplasma and sterility.

Figure 17:
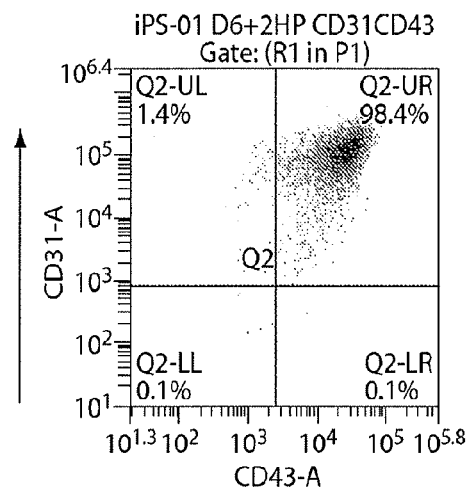
FIG. 17. FACS Analysis CD31+, CD43+–MLP Derived from hiPSC.

Additionally, a representative vial of cryopreserved MLPs is assessed for CD31 and CD43 expression, as follows. CD31 is a marker for hemogenic endothelial cells expressed in both endothelial and hematopoietic lineages. Expression of CD43 confirms hematopoietic commitment. A sample vial of cryopreserved MLPs is thawed rinsed, resuspended in DPBS plus 3% FBS (FACS buffer) and centrifuged (160×g for 5 minutes). The pellet is resuspended in DPBS plus 3% FBS (FACS buffer) containing CD31-APC-conjugated (allophycocyanin) and CD43-FITC-conjugated (BD Bioscience, San Jose, Calif.). Samples of thawed MLPs are incubated with the fluorescent conjugated antibodies and the appropriate isotype controls (mouse IgG-APC and mouse IgG-FITC) for 15 minutes at room temperature. Labeled cells are then diluted in FACS buffer, centrifuged and resuspended in FACS buffer. FACS analysis is performed by monitoring 10,000 events. Acceptable MLP banks have >1=50% CD31 positive cells and >1=50% CD43 positive cells. Shown in FIG. 17 is a representative two dimensional dot plot for MLPs derived from hiPSC line MA-iPS-01. In the example shown, the cell population is 99.8% CD31+; 98.5% CD43+ with 98.4% of the population staining double positive.

Additionally, a representative vial of cryopreserved MLPs is assessed by FACS analysis utilizing pluripotent markers such as SSEA4, TRA-1-60 to confirm the absence of pluripotent cells.

Sample cryovials of cryopreserved MLPs are thawed and assessed for viability and recovery post-thaw. MLPs are further processed to the point of proplatelet formation and assessed for morphology MK morphology and FACS analysis for CD41a+ and CD42b+ during MK maturation. Cultures are monitored for proplatelet formation and for platelet formation and characterization by FACS analysis for doubly stained (CD41a+ and CD42b+) cells. Acceptance criteria include: sterility (negative on <USP 21> Immersion test), negative for mycoplasma (tested by Direct (agar & broth), Indirect (cell culture)), at least 90% positive for CD31 and CD43 by FACS, at least 70% viability by Trypan Blue, and negative for expression of pluripotent cell markers.

Figure 18:
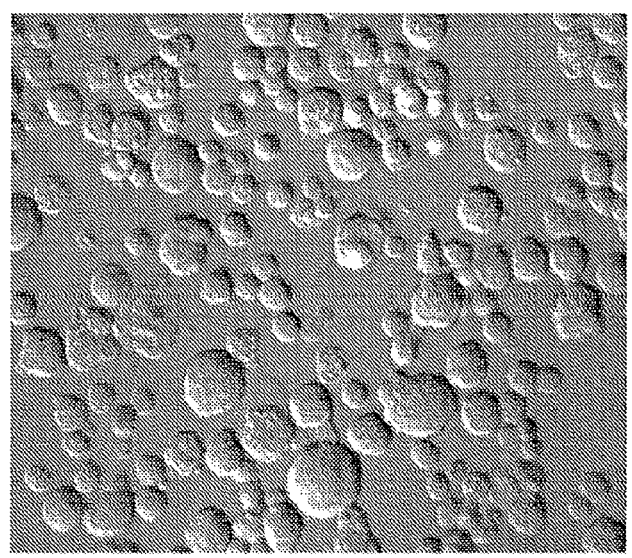
FIG. 18. Representative MKs derived from hESC.

Referring to FIG. 14, steps 13-14, after 2-3 days post-thaw and seeding of MLPs cultures are assessed for emergence of free-floating cells in the MK lineage. At this time cells are heterogeneous in size ranging from 10-50 microns in diameter. The approximate proportion of viable cells is assessed by visual observation in an inverted light microscope with healthy MK precursor cells and MKs displaying bright cytoplasm and smooth cellular membranes. Shown in FIG. 18 is microphotograph of a representative population of MKs derived from hESC (Hoffman Modulation Contrast, ×400).

Referring to FIG. 14, steps 13-14, after 2-3 days post-thawing of MLPs, cell samples are removed from representative culture vessels, pooled, processed, labeled with fluorescent-conjugated antibodies to CD41a and CD41b, and undergo FACS analysis. Cultures with an acceptable percentage of cells expressing both CD41a+ and CD42b+ MLPs are processed further (preferably at least 10% double positive cells).

Figure 19:
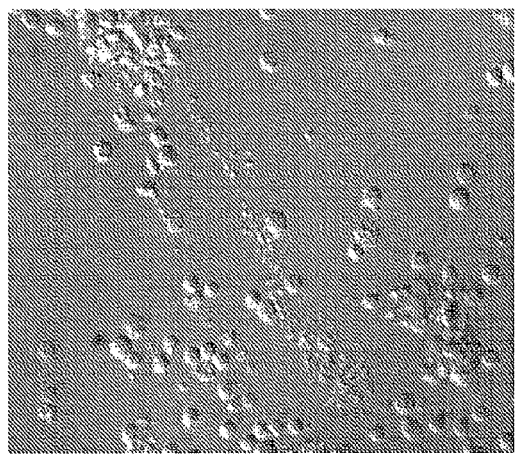
FIG. 19. Proplatelet Formation from MK.

Referring to FIG. 14, step 15, beginning at 3 days and out to 5 days post-thawing of MLPs, MK cultures are assessed for the appearance of proplatelets. The arrows in FIG. 19 depict proplatelet morphology. MK displaying proplatelets exhibit long projections extending from the cells showing some beading and branching prior to fragmentation.

Referring to FIG. 14, steps 15-16, upon confirming the presence of proplatelets, beginning at 3 days and out to 8 days post-thawing of MLPs, samples of proplatelets and platelets are collected from representative cultures. Briefly, using a 10 mL serological pipette, the samples are transferred to a 50 mL conical tube and drawn up and expelled at least 5 times to generate shear force sufficient to fracture the proplatelets. Samples are returned to a 39° C. incubator gassed with 10% $CO_2$ and allowed to settle for 30 minutes. Approximately 250 µL of the supernatant containing suspended platelets is stained and undergoes FACS analysis for CD41a and CD42b. Platelet harvesting and subsequent processing is initiated when peak levels of platelets are detected, typically when 30-70% of the platelets are double positive stained (CD41a+CD42b+).

hiPSC-PLT and hESC-PLT are characterized for pH, platelet count and identity (determined by expression of CD61, CD41a, CD42b), expression of platelet activation markers (CD62P, PAC1, Platelet Factor 4), Physiologic responses (Aggregation (microplate assay), TEG (thromboelastography), and Spreading), and morphologically evaluated by Electron Microcopy as well as DIC Microscopy with β1 Tubulin staining.

Cells are further tested for sterility (negative result of <USP 21> Immersion test), endotoxin (Gel Clot USP <85> less than 5 EU/ml), mycoplasma (negative result by European Pharmacopoeia and US Pharmacopoeia test), identity (by FACS, at least 70% CD41a+, CD42b+), PLT Count/mpPLT (FACS for CD61), morphology (DIC Microscopy with β1 Tubulin Staining), and potency by PAC1 Binding (Activated).

Purified platelets are stained with fluorescent-conjugated antibodies to CD41a and CD41b and undergo FACS analysis as described above. Shown below are representative two dimensional dot plot of PLTs derived from iPS-01. In the example shown in FIG. 20, the population is 81.8% CD41a+; 69.2% CD42b+ with 68.2% of the population staining double positive.

Figure 20:
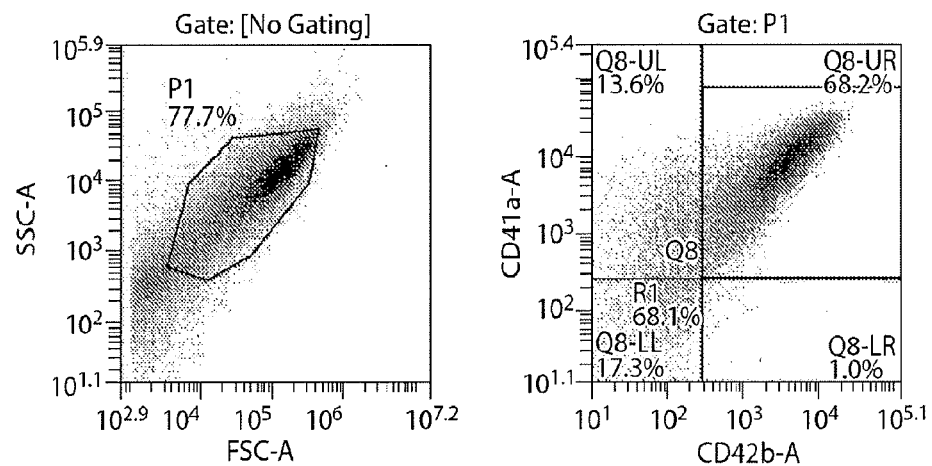
FIG. 20. FACS Analysis CD41a, CD42b.

In conjunction with CD41a+, CD42b+ FACS performed in FIG. 20, propidium iodine (PI) is added to the sample during CD staining to assess viability. FACS analysis is performed counting 10,000 events as described previously, with additional events collected at flow channel 3 to detect PI positive events (nonviable platelets). Data are analyzed to give the percentage of CD41a+/CD41b+ platelets and the percent viability (Total Platelets Detected–PI+ Platelets/Total Platelets Detected).

Each final product lot of platelets is assessed for the number of platelets and the number of platelet microparticles by detecting CD61 positive events using flow cytometric analysis. This assay is performed using a known number of fluorescent beads to normalize data and obtain the absolute number of PLTs/µL and mpPLTs/µL. Briefly, 5-10 µL samples of platelets are diluted in 0.9% saline and dispensed into each of two tubes:

1) one TruCount (BD Cat#340334) tube containing a lyophilized pellet with a known number of fluorescent beads and phycoerythrin-conjugated anti-CD61 IgG in a final reaction volume of 60 µL/tube and 2) one isotype control tube containing PE-conjugated mouse IgG to account for nonspecific primary antibody binding in a final reaction volume of 60 µL/tube.

The tubes are gently mixed, incubated for 20 minutes at 20-24'C followed by the addition of 400 µL of cold (2-8° C.) 1% formaldehyde and storage in the cold, protected from light for two hours. Prior to analyzing the fixed platelet samples, the FACS machine settings for the peak channel, gating, axes, quadrant locations, and marker boundaries for the appropriate regions of data acquisition are determined by collecting a minimum of 10,00 events from a sample of freshly sonicated latex beads with a uniform diameter of 1 µM (CML Cat#C37483) diluted in 0.9% saline. After applying these settings, a minimum of 100,000 events is acquired for the isotype control and for the CD61 stained sample. The counts obtained on the CD61 sample will register events for CD-61 positive fluorescence-stained PLTs, CD-61 positive mpPLTs and for the number of Trucount fluorescent beads detected. Events counted in the preset regions are analyzed in the platelet size range 2-4 microns and in the mpPLTs quadrant corrected for nonspecific binding detected in the isotype control. Data are normalized to the efficiency of Trucount beads detected using the following formula based on the known number of Trucount beads per tube provided by the manufacturer.

Events Counted/# Beads Counted X # TruCount Beads per tube/Sample Volume=mpPLT/μL or PLT/μL.

Figure 21:
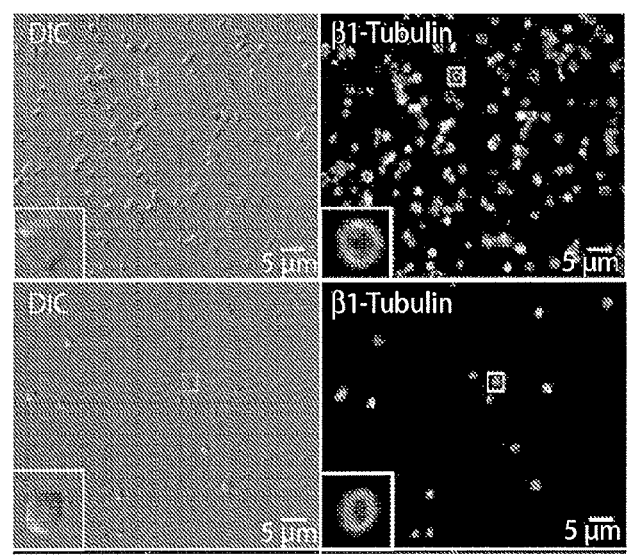
FIG. 21. DIC Microscopy with β1-Tubulin Staining, Human Donor PLT (top) hESC-PLT (bottom).

Additionally, microscopic inspection is utilized to assess hESC-PLT and hiPSC-PLT morphology. Morphology is assessed by Differential Interference Contrast Microscopy (DIC) and by confirming staining for β1-tubulin in a characteristic circumferential band of microtubules unique to platelets. Briefly, platelets are fixed in 4% formaldehyde and centrifuged onto 1 μg/ml poly-1-lysine-coated coverslips, permeabilized with 0.5% Triton X-100, and blocked in immunofluorescence blocking buffer (0.5 g BSA, 0.25 ml of 10% sodium azide, and 5 ml FCS in 50 ml PBS) for a minimum of two hours before antibody labeling. To demarcate permeabilized cells, samples are incubated with a rabbit polyclonal primary antibody for human β1-tubulin generated against the C-terminal peptide sequence CKAV-LEEDEEVTEEAEMEPEDKGH (Genemed Synthesis, Inc.) (SEQ ID NO:1). Samples are then treated with a secondary goat anti-rabbit antibody conjugated to an Alexa Fluor 568 nm (Invitrogen; Molecular Probes), with extensive washes with PBS between and after the incubations. Coverslips are mounted (Aqua Polymount; Polysciences) onto microscope slides. As background controls, slides are incubated with the secondary antibody alone and images are adjusted to account for nonspecific binding of antibodies. Samples are examined with a microscope equipped with an oil immersion objective or differential interference contrast objective. Images are obtained using a charged-coupled device camera. Images were analyzed using the MetaMorph image analysis software (Molecular Devices) and ImageJ (National Institutes of Health). Characteristic features of resting platelets are assessed as follows: Differential-interference contrast (DIC) microscopy: Disc-shaped, approximately 2-3 μM in diameter β1-Tubulin staining: A prominent, circumferential band of microtubules with a diameter similar to resting platelets. See FIG. 21.

Platelets (hESC-PLTs and hiPSC-PLTs) are additionally tested to confirm the absence of pluripotent cells (e.g., by PCR, immunofluorescence, and/or FACS to detect pluripotency markers). To enhance sensitivity, detection methods may be coupled with procedures to concentrate potential cellular contaminants by trapping with filters, matrices or gradients coupled with low speed centrifugation to pellet cells and while leaving platelets in the supernatant.

Platelets (hESC-PLTs and hiPSC-PLTs) are additionally tested for the presence of microorganisms according to the immersion method, USP <21>, CFR 610.12.

Platelets (hESC-PLTs and hiPSC-PLTs) are additionally tested for endotoxin. Gram-negative bacterial endotoxins are quantified using the Pyrotell® Gel Clot Endotoxin System (Associates of Cape Cod, Inc.). Appropriate negative, positive, and positive product controls are prepared. Positive product controls are inhibition controls and consist of the specimen or dilution of specimen to which standard endotoxin is added. The samples are added directly to the Pyrotell® reagent and mixed thoroughly. The reaction tubes are incubated at 37° C.±1° C. for 60±2 minutes. A positive test is indicated by the formation of a gel which does not collapse when the tube is inverted. Endotoxin is quantified by finding the endpoint in a series of specimen dilutions. In the absence of the endotoxin series, a positive control of know concentration may be included with the tests. The endotoxin assay will be validated for use with PLT samples and is performed in a manner consistent with the 1987 FDA guidance on endotoxin validation.

Platelets (hESC-PLTs and hiPSC-PLTs) are additionally tested for mycoplasma. After centrifugation of platelets prior to running the HSA gradient, the supernatants (e.g., consisting of conditioned StemSpan ACF medium) are collected and pooled. Samples of purified platelets from the final product batch and the conditioned medium are sent for mycoplasma testing. Mycoplasma detection is performed as per the European Pharmacopoeia and US Pharmacopoeia Guidelines with indirect cultivation on indicator cell cultures and direct inoculation on agar plates and into broth.

Example 6. Assay for Platelet Potency and PAC-1 Binding

Platelets of the disclosure may be assessed for potency and/or PAC-1 binding using the methods described in this example.

Platelet activation in vivo induces conformational changes in αIIbβ3 integrin activating the fibrinogen receptor function of the GPIIb/IIIa complex leading to enhanced ligand binding. Activated platelet bind to substrates including fibrinogen and Von Willebrand Factor and stimulate thrombus formation at the site of vascular injury. To determine the extent of functional αIIbβ3 integrin expression that occurs upon platelet activation, hESC-PLTs, iPSC-PLTs, and purified normal human platelets are activated and assessed for the extent of PAC-1 binding as compared to resting control PLTs. The PAC-1 is a fibrinogen mimetic that binds exclusively to the activated conformation of the αIIbβ3 integrin.

PLTs are counted and a minimum of 100,000 PLTs is removed and diluted with additional medium to a density of approximately 20 PLT/uL. PAC1-FITC (BD, 1:100 dilution) and antibodies (CD41a-APC-conjugated (allophycocyanin) 1:100 and CD42b-PE-conjugated (phycoerythrin) 1:100 (BD Bioscience, San Jose, Calif.) are added to the PLT sample. One half of the sample (250 uL) is dispensed into each of two 5 mL FACS tubes. To one tube, thrombin (Sigma) is added to a final concentration of 1 U/mL. Activated PLTs exposed to thrombin and control samples are incubated at room temperature for 15-20 minutes. Samples undergo FACS analysis with forward versus side scatter gating being determined using human blood platelets as controls. PAC-1 binding (activation) is quantified by comparing the number of CD41a and PAC-1 positive events in the activated to those in the unactivated control.

Example 7. Use of Proteases Such as MMP Inhibitors to Improve Yields and Purity of Platelets Generated Under Shear Force This disclosure also embraces platelet production methods that employ shear force conditions (e.g., the culture medium is in flow during the culture. The culture was performed using a microfluidic device in which flow rates in the range of tens of microliters/min approximate the shear forces in the bone marrow cavity during hemopoiesis. In some instances, the flow rate is in the range of 5-25 microliters/min. Megakaryocytes generated from iPS cells or ES cells according to this disclosure, when cultured under shear force, have been found to shed platelets in a much more efficient way.

The device used to culture the MLPs must be able to immobilize the MLPs without attachment. In some instances, this means that the MLPs are located within a region or chamber of the device from which they are accessible to the moving culture medium but not able to move significantly themselves.

This disclosure recognizes that platelet yield and purity can be improved in these culture systems. In one aspect, the improvement is achieved through use of one or more certain protease inhibitors during shear force culture. This Example demonstrates the benefit of adding a matrix metalloproteinase (MMP) inhibitor during these culture conditions. It is to be understood that the MMP inhibitor is representative of other protease inhibitors that similarly can be used in these methods such as but not limited to plasminogen activator inhibitors.

In another aspect, an improvement in platelet yield and purity is achieved by performing the culture at increased shear force. The shear force may be 1, 1.5, 2, 2.5, 3, 3.5, 4 or 4.5 dynes/cm$^2$.

Matured MKs, derived from HA-iPS and MA09 hES lines, were used. Equal numbers of MKs suspended in MK-specific medium were loaded into a microfluidic device in the presence or absence of 20 µM MMP inhibitor GM6001. Constant shear force was applied to the MKs throughout the culture period. MK-medium downstream of MKs was collected at 30 minute intervals for a period of 6 hours. Platelet number and purity (i.e., percentage of total cells that are CD41a$^+$CD42b$^+$) in the collected media were measured using flow cytometer.

Figure 22:
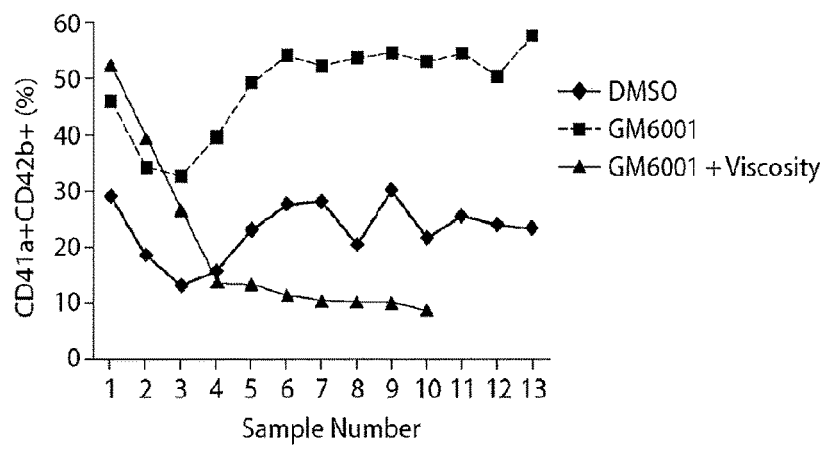
FIG. 22. Platelet purity as a function of time in the presence of DMSO (diamonds), MMP inhibitor GM6001 (squares), and GM6001 and 8% dextran (referred to as "viscosity") (triangles), under constant shear force culture conditions. The x-axis corresponds to sample number, with a sample removed every 30 minutes over a 6+ hour culture.
Figure 23:
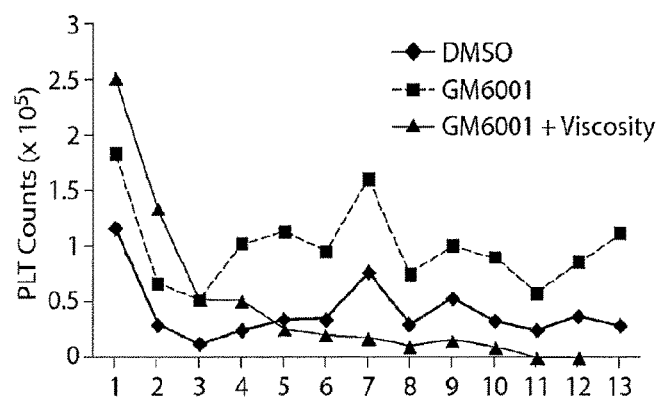
FIG. 23. Platelet numbers as a function of time in the presence of DMSO (diamonds), MMP inhibitor GM6001 (squares), and GM6001 and 8% dextran (referred to as "viscosity") (triangles), under constant shear force culture conditions. GM6001 was added to the culture at day 0.
Figure 24:
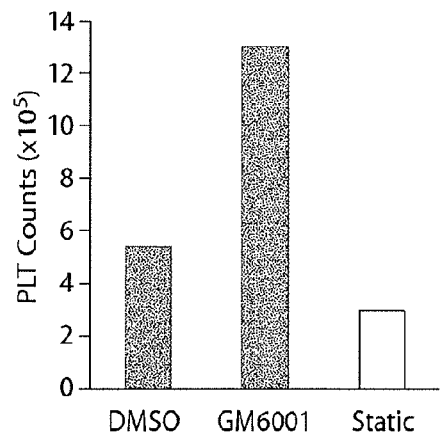
FIG. 24. Platelet numbers in the presence of DMSO (left bar) and MMP inhibitor GM6001 (middle bar) under constant shear force culture conditions, and under static culture conditions (in the absence of MMP inhibitor GM6001) (right bar).

FIGS. 22-24 provide the results of platelet generation from MKs derived from HA-iPS. The platelets were generated under a constant shear force defined by a flow rate of [PLEASE PROVIDE] µl/min. The addition of MMP inhibitor GM6001 at the beginning of the culture significantly improved the purity (FIG. 22) and yield (FIG. 24) of the newly generated platelets. Purity is expressed at the percentage of total harvested cells that are CD41a$^+$ CD42b$^+$. Increasing the viscosity of the culture medium by adding 8% dextran had a negative impact on platelet formation.

FIG. 23 demonstrates that significantly more platelets were generated from MKs under shear force culture when the MMP inhibitor GM6001, is present.

FIG. 24 demonstrates the difference in platelet yields in shear force cultures in the presence of the MMP inhibitor GM6001 or DMSO, or under a static culture.

Figure 25:
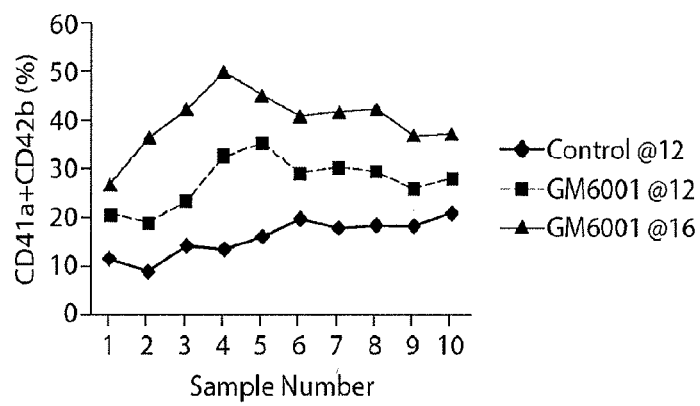
FIG. 25. Platelet purity as a function of time in the presence of MMP inhibitor GM6001 in a microfluidic device at a flow rate of 12 microliters/min (squares) and at a flow rate of 16 microliters/min (triangles). The control (diamonds) is in the presence of DMSO since the MMP inhibitor is dissolved in DMSO.
Figure 26:
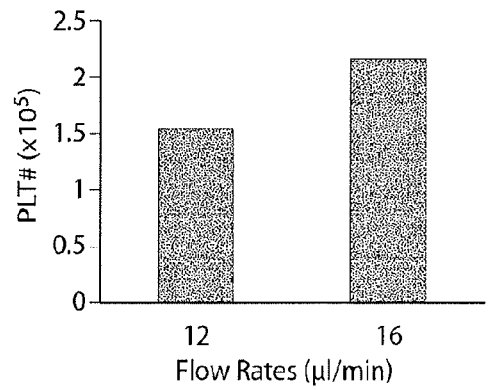
FIG. 26. Platelet numbers as a function of flow rate. Left bar: 12 microliters/min, Right bar: 16 microliters/min.

FIG. 25 demonstrates that similar results are achieved when MA09 (ES) derived MKs were used to generate platelets. FIGS. 25 and 26 also demonstrate that a moderate change of shear force (represented by flow rate change from 12 to 16 µl/min) also improves platelet purity and yield.

Example 8. MMP8 Specific Inhibitor as a Protective Inhibitor Useful in Platelet Formation in Static Culture Proteases such as MMPs are involved in shedding of CD42b, which is also called GPIbα. Platelet CD42b is the receptor for vWF and it mediates initial platelet involvement in wounds healing. Loss of CD42b can therefore result in poor platelet quality. A broad-spectrum MMP inhibitor, GM6001, is reported to inhibit CD42b shedding from platelets.

In a comparative study using several specific MMP inhibitors, an MMP8 inhibitor was identified as having more potency than GM6001 in protecting platelet function. As shown in FIG. 26, the addition of an MMP8 specific inhibitor at the peak of platelet production of MKs significantly improved the purity of iPS-derived platelets from 43.7% to 65.5%, the latter of which is approximately 10% more than was obtained from GM6001-treated cultures. Significantly more CD41a$^+$CD42b$^+$ platelets are produced in the presence of MMP8 specific inhibitor as compared to GM6001. When the MMP8 specific inhibitor and GM6001 are used in combination, purity levels appear unaffected (FIG. 27) while platelet yields are increased (FIG. 28). The peak of platelet production is determined by measuring platelet content in the culture, for example on a daily basis for several days. It is typically 4-7 days after the beginning of the MLP differentiation culture period, although it may be longer or it may be shifted.

Figure 27:
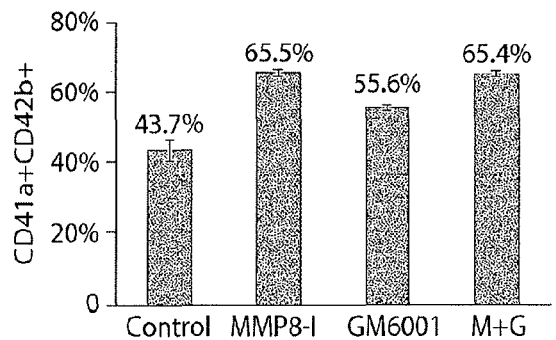
FIG. 27. Platelet purity as a result of static culture in the presence of MMP8 specific inhibitor MMP8-I (second bar), pan-MMP inhibitor GM6001 (third bar), or the combination of MMP8-I and GM6001 (fourth bar). The MMP8-I is (3R)-(+)-[2-(4-Methoxybenzenesulfonyl)-1,2,3,4-tetrahydroisoquinoline-3-hydroxamate], and it is commercially available from Millipore. The first bar is the control.
Figure 28:
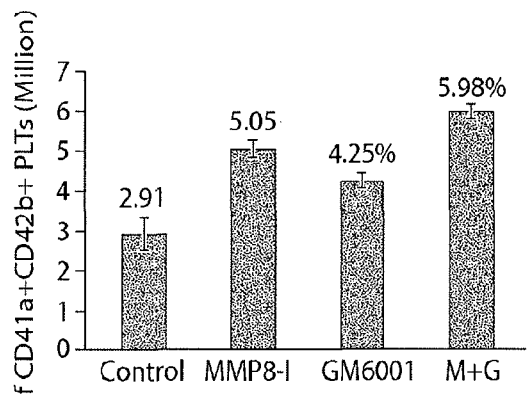
FIG. 28. Platelets numbers as a result of static culture in the presence of MMP8 specific inhibitor MMP8-I (second bar), pan MMP inhibitor GM6001 (third bar), or the combination of MMP8-I and GM6001 (fourth bar). The first bar is the control.

While the data in FIGS. 27 and 28 were generated using iPS derived megakaryocytes, this disclosure provides for the use of an MMP8 specific inhibitor in cultures of naturally occurring sources of platelets such as bone marrow and umbilical cord blood CD34$^+$ progenitor cells.

Example 9. iPS Platelet Generation at Elevated Temperature

Figure 29:
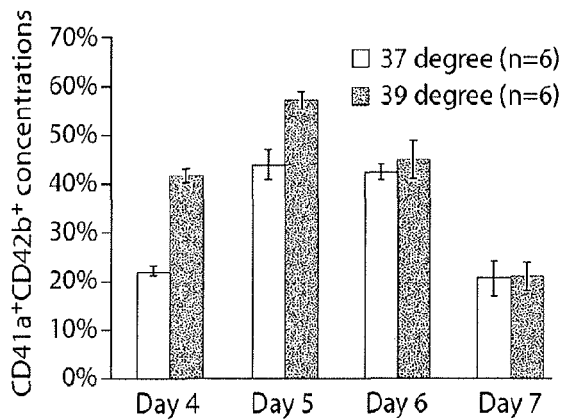
FIG. 29. Platelet purity as a function of time in culture at 37° C. (left bar per pair) and 39° C. (right bar per pair). The temperature was set at the beginning of and maintained throughout the culture.
Figure 30:
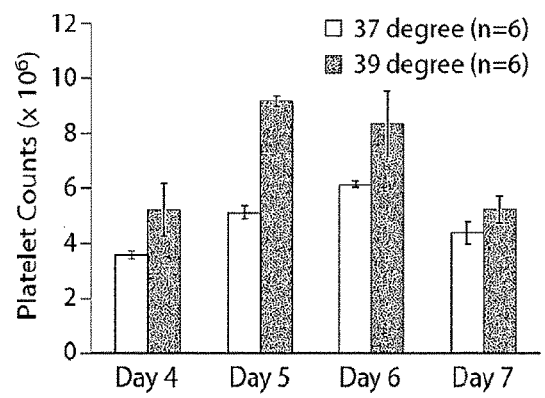
FIG. 30. Platelet number as a function of time in culture at 37° C. (left bar per pair) and 39° C. (right bar per pair).

FIGS. 29 and 30 demonstrate that culturing megakaryocytes under mild hyperthermic conditions significantly improved both platelet purity and yield. The percentage of CD41a$^+$CD42b$^+$ platelets is significantly higher in cultures incubated at 39° C. than at 37° C. The effect is most apparent prior to reaching the platelet production peak. In addition to improving the purity, higher temperature incubation of megakaryocytes also contributed to higher yield of platelet from the same starting number of megakaryocytes, indicating that elevated temperature has no adverse effect on megakaryocytes or platelets in the culture systems provided herein.

Example 10. iBET Promotes Megakaryocyte Commitment and Increases Overall Platelet Yield Via Down-Regulation of c-Myc Gene In our new method of megakaryocyte lineage specific differentiation, the emergence of megakaryocyte progenitors best suited for platelet production can only be harvested in a short period of 3-4 days from the beginning of the PVE-HE cell culture period. The gradual increase of myeloid lineage CD14$^+$ cells appears to be associated with decrease in megakaryocyte quality and platelet yield. In an effort to achieve higher and better yields of megakaryocyte progenitors, the c-myc gene was targeted as an important regulatory gene during early megakaryopoiesis with the aim of identifying novel megakaryocyte-promoting factors.

GSK1210151A (I-BET151) is an orally-available, imidazolonoquinoline-based inhibitor of the BET family of bromodomains. I-BET151 was shown to have profound efficacy against human and murine MLL-fusion leukemic cell lines, through the induction of early cell cycle arrest and apoptosis. The mode of action is partly due to the inhibition of transcription of key genes (BCL2, C-MYC, and CDK6) through the displacement of BRD3/4, PAFc, and SEC components through chromatin.

Figure 31:
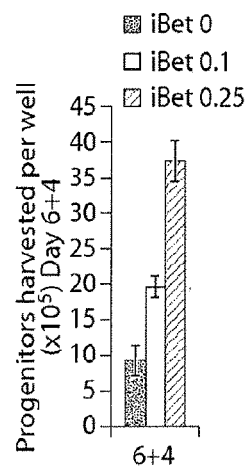
FIG. 31. Megakaryocyte progenitor (MLP) numbers harvested at day 6+4 (i.e., day 10 of differentiation) as a function of increasing dose of iBET-151 (in µM). iBET is added to the culture at the 6+3 day time frame, and MLPs are exposed to iBET for a period of about 24 hours prior to their harvest. iBET concentrations: 0 (left bar), 0.1 microM (middle bar), 0.25 microM (right bar).
Figure 32:
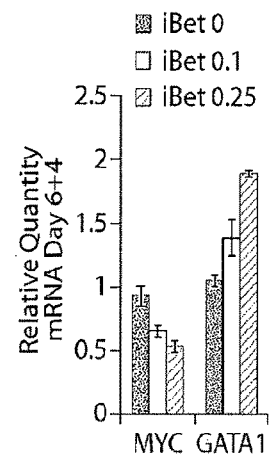
FIG. 32. Relative quantitative analysis of mRNA of c-myc and GATA-1 on day 6+4 as a function of increasing dose of iBET-151. iBET concentrations: 0 (left bar), 0.1 microM (middle bar), 0.25 microM (right bar) for each triplet.
Figure 33:
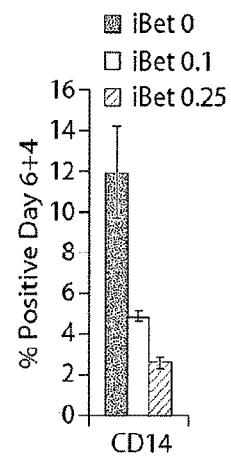
FIG. 33. CD14+ cell purity in cell population harvested at day 6+4 as a function of increasing dose of iBET-151. iBET concentrations: 0 (left bar), 0.1 microM (middle bar), 0.25 microM (right bar).

Although high dose i-BET-151 triggers massive apoptosis, treating cells undergoing in vitro megakaryopoiesis with lower doses in the micromolar range (or submicromolar range) resulted in increased numbers of MK progenitors FIG. 31 demonstrates, through quantitative mRNA analysis, a dose-dependent inhibition of c-myc gene expression by i-BET-151. in contrast, pro-MK gene GATA1 gene was up-regulated (FIG. 32) in response to i-BET-151. Treatment with i-BET-151 also resulted in a dose-dependent decrease in the number of CD14$^+$ myeloid cells.

Thus, using the methods provided herein for in vitro generation of iPS-derived (and ES-derived) megakaryocytes and platelets, it has been further discovered that suppression of endogenous c-myc gene expression in cells undergoing megakaryopoiesis can change the balance of cell differentiation in favor of the MK-lineage.

What is claimed is:

1. A method for producing human megakaryocytes comprising:
   (a) culturing human pluripotent stem cells under an adherent condition in culture medium that comprises bone morphogenetic protein 4, basic fibroblast growth factor, and vascular endothelial growth factor to form human hemogenic endothelial cells;
   (b) culturing the human hemogenic endothelial cells in culture medium that comprises two or more factors selected from thrombopoietin, interleukin-3, and interleukin-6 to form human megakaryocyte progenitors; and
   (c) culturing the human megakaryocyte progenitors under a non-adherent culture condition in culture medium that comprises thrombopoietin and one or more factor(s) selected from stem cell factor, interleukin-6, interleukin-9, and a ROCK inhibitor to form human megakaryocytes.

2. The method of claim 1, wherein the human pluripotent stem cells are human induced pluripotent stem cells.

3. The method of claim 1, wherein the human hemogenic endothelial cells are cultured in the presence of a BET inhibitor.

4. The method of claim 3, wherein the BET inhibitor is IBET151.

5. The method of claim 3, wherein the concentration of BET inhibitor is within a micromolar or submicromolar range.

6. The method of claim 5, wherein the concentration of BET inhibitor is 0.25 µM.

7. The method of claim 1, wherein the culture medium of step (b) comprises thrombopoietin, interleukin-3, and interleukin-6.

8. The method of claim 1, wherein the culture medium of step (c) comprises stem cell factor, thrombopoietin, interleukin-6, interleukin-9, and a ROCK inhibitor.

9. The method of claim 8, wherein the ROCK inhibitor is Y27632.

10. The method of claim 1, wherein the human hemogenic endothelial cells are differentiated from the human pluripotent stem cells under low oxygen conditions comprising 1% to 10% oxygen.

11. The method of claim 10, wherein the human hemogenic endothelial cells are differentiated from the human pluripotent stem cells under low oxygen conditions comprising 4% to 6% oxygen.

12. The method of claim 1, wherein the human megakaryocyte progenitors are cultured to form human megakaryocytes at a temperature between 38-40° C.

13. The method of claim 1, wherein the human hemogenic endothelial cells express CD31.

14. The method of claim 1, wherein the human megakaryocyte progenitors express CD41a.

15. The method of claim 1, wherein the step of culturing human pluripotent stem cells under an adherent condition comprises culturing human pluripotent stem cells on an extracellular matrix.

16. The method of claim 1, wherein the human pluripotent stem cells of step (a) are cultured under a feeder-free culture condition.

17. A method for producing human megakaryocytes comprising:
   (a) culturing human pluripotent stem cells under an adherent condition in culture medium that comprises bone morphogenetic protein 4, basic fibroblast growth factor, and vascular endothelial growth factor to form human hemogenic endothelial cells;
   (b) culturing the human hemogenic endothelial cells in culture medium that comprises stem cell factor, thrombopoietin, Fms-related tyrosine kinase 3 ligand, interleukin-3, and interleukin-6 to form human megakaryocyte progenitors; and
   (c) culturing the human megakaryocyte progenitors under a non-adherent culture condition in culture medium that comprises stem cell factor, thrombopoietin, interleukin-6, and interleukin-9 to form human megakaryocytes.

18. The method of claim 17, wherein the human hemogenic endothelial cells are cultured in the presence of a ROCK inhibitor and/or a BET inhibitor.

19. A method for producing human megakaryocytes comprising:
   (a) culturing human pluripotent stem cells under an adherent condition in culture medium that comprises bone morphogenetic protein 4, basic fibroblast growth factor, and vascular endothelial growth factor to form human hemogenic endothelial cells;
   (b) culturing the human hemogenic endothelial cells in culture medium that comprises two or more factors selected from thrombopoietin, interleukin-3, interleukin-6, and Fms-related tyrosine kinase 3 to form human megakaryocyte progenitors; and
   (c) culturing the human megakaryocyte progenitors under a non-adherent culture condition in culture medium that comprises thrombopoietin and one or more factor(s) selected from stem cell factor, interleukin-6, interleukin-9, and a ROCK inhibitor to form human megakaryocytes.

20. The method of claim 19, wherein the human pluripotent stem cells are human induced pluripotent stem cells.

21. The method of claim 19, wherein the human hemogenic endothelial cells are cultured in the presence of a BET inhibitor.

22. The method of claim 19, wherein the culture medium of step (b) comprises thrombopoietin, Fms-related tyrosine kinase 3 ligand, interleukin-3, and interleukin-6.

23. The method of claim 19, wherein the culture medium of step (c) comprises stem cell factor, thrombopoietin, interleukin-6, interleukin-9, and a ROCK inhibitor.

24. The method of claim 19, wherein the step of culturing human pluripotent stem cells under an adherent condition comprises culturing human pluripotent stem cells on an extracellular matrix.

25. The method of claim 19, wherein the human pluripotent stem cells of step (a) are cultured under a feeder-free culture condition.

26. A method for producing human megakaryocytes comprising:
(a) culturing human pluripotent stem cells under an adherent condition in culture medium that comprises bone morphogenetic protein 4, basic fibroblast growth factor, and vascular endothelial growth factor to form human hemogenic endothelial cells;
(b) culturing the human hemogenic endothelial cells in culture medium that comprises two or more factors selected from thrombopoietin, interleukin-3, interleukin-6, and stem cell factor to form human megakaryocyte progenitors; and
(c) culturing the human megakaryocyte progenitors under a non-adherent culture condition in culture medium that comprises thrombopoietin and one or more factor(s) selected from stem cell factor, interleukin-6, interleukin-9, and a ROCK inhibitor to form human megakaryocytes.

27. The method of claim 26, wherein the human pluripotent stem cells are human induced pluripotent stem cells.

28. The method of claim 26, wherein the human hemogenic endothelial cells are cultured in the presence of a BET inhibitor.

29. The method of claim 26, wherein the culture medium of step (b) comprises thrombopoietin, stem cell factor, interleukin-3, and interleukin-6.

30. The method of claim 26, wherein the culture medium of step (c) comprises stem cell factor, thrombopoietin, interleukin-6, interleukin-9, and a ROCK inhibitor.

31. The method of claim 26, wherein the step of culturing human pluripotent stem cells under an adherent condition comprises culturing human pluripotent stem cells on an extracellular matrix.

32. The method of claim 26, wherein the human pluripotent stem cells of step (a) are cultured under a feeder-free culture condition.

\* \* \* \* \*

UNITED STATES PATENT AND TRADEMARK OFFICE
CERTIFICATE OF CORRECTION

PATENT NO. : 10,426,799 B2
APPLICATION NO. : 14/653969
DATED : October 1, 2019
INVENTOR(S) : Qiang Feng et al.

Page 1 of 1

It is certified that error appears in the above-identified patent and that said Letters Patent is hereby corrected as shown below:

On the Title Page

In item (71) Applicant:
Please replace "Ocata Therapeutics, Inc." with --Astellas Institute for Regenerative Medicine--.

Signed and Sealed this
Tenth Day of December, 2019

Andrei Iancu
*Director of the United States Patent and Trademark Office*